US006887673B2

(12) United States Patent
Kunkel et al.

(10) Patent No.: US 6,887,673 B2
(45) Date of Patent: May 3, 2005

(54) HUMANIZED ANTIBODIES AGAINST HUMAN 4-1BB

(75) Inventors: Maria Jure Kunkel, Plainsboro, NJ (US); Subinay Ganguly, Newtown, PA (US); Ralph Abraham, Lawrenceville, NJ (US); Diane L. Hollenbaugh, Mountain View, CA (US); Jill Rillema, Belmont, CA (US); Barbara Thorne, Sammamish, WA (US); Walter W. Shuford, Redmond, WA (US); Robert S. Mittler, Decatur, GA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 77 days.

(21) Appl. No.: 10/630,406

(22) Filed: Jul. 30, 2003

(65) Prior Publication Data

US 2004/0105855 A1 Jun. 3, 2004

Related U.S. Application Data

(60) Provisional application No. 60/399,646, filed on Jul. 30, 2002.

(51) Int. Cl.$^7$ .......... G01N 33/53

(52) U.S. Cl. .......... 435/7.1; 435/7.91; 435/7.92; 436/514; 436/547; 436/15; 530/387.5; 530/387.1; 530/388.2

(58) Field of Search .......... 435/7.1, 7.91, 435/7.92; 436/514, 547, 15; 530/387.5, 387.1, 388.2

(56) References Cited

U.S. PATENT DOCUMENTS

| | | | |
|---|---|---|---|
| 5,530,101 | A | 6/1996 | Queen et al. |
| 5,928,893 | A | 7/1999 | Kang et al. |
| 6,210,669 | B1 | 4/2001 | Aruffo et al. |
| 6,303,121 | B1 | 10/2001 | Kwon |
| 6,355,779 | B1 | 3/2002 | Goodwin et al. |
| 6,458,934 | B1 | 10/2002 | Hong et al. |

OTHER PUBLICATIONS

Kim, Y. et al., Eur. J. Immunol., "Human 4–1BB Regulates CD28 Co–Stimulation to Promote Th1 Cell Responses", vol. 28, pp. 881–890 (1998).

Ashkenazi, A., Nature, "Targeting Death and Decoy Receptors Of The Tumour–Necrosis Factor Superfamily", vol. 2, pp. 420–430 (2002).

Pollok, K. et al., Eur. J. Immunol., 4–1BB T–Cell Antigen Binds To Mature B Cells and Macrophages, and Costimulates Anti–$\mu$–Primed Splenic B Cells, vol. 24, pp. 367–374 (1994).

Melero, I. et al., Cellular Immunology, "NK1.1 Cells Express 4–1BB (CDw137) Costimulatory Molecule and Are Required for Tumor Immunity Elicited by Anti–4–1BB Monoclonal Antibodies", vol. 190, pp. 167–172 (1998).

Kwon, B. et al., Mol. Cells, "4–1BB: Still in the Midst of Darkness", vol. 10, No. 2, pp. 119–126 (2000).

Rosenberg, S., Nature, "Progress in Human Tumour Immunology and Immunotherapy", vol. 411, pp. 380–384 (2001).

Halapi, E., Medical Oncology, Oligoclonal T Cells in Human Cancer, vol. 15, pp. 203–211 (1998).

Resser, J. et al., Current Opinion in Oncology, "Immunotherapy of Head and Neck Cancer", vol. 10, pp. 226–232 (1998).

Elder, D., Acta Oncologica, "Tumor Progression, Early Diagnosis and Prognosis of Melanoma", vol. 38, pp. 535–547 (1999).

Zhang, L. et al., The New England Journal of Medicine, "Intratumoral T Cells, Recurrence, and Survival in Epithelial Ovarian Cancer", vol. 348, pp. 203–213 (2003).

Rosenberg, S., The Cancer Journal From Scientific American, "Interleukin–2 and the Development of Immunotherapy for the Treatment of Patients With Cancer", vol. 6, pp. S2–S7 (2000).

Bassi, P., Surgical Oncology, "BCG (Bacillus of Calmette Guerin) Therapy of High–Risk Superficial Bladder Cancer", vol. 11, pp. 77–83 (2002).

Fishman, M. et al., Expert Opin. Investig. Drugs, "Novel Therapies For Renal Cell Carcinoma– An Update", vol. 12, No. 4, pp. 593–609 (2003).

Lenschow, D. et al., Annu. Rev. Immunol., "CD28/B7 System of T Cell Costimulation", vol. 14, pp. 233–258 (1996).

Chambers, C. et al., Current Opinion in Immunology, "Co–Stimulation in T–Cell Responses", vol. 19, pp. 396–404 (1997).

Abbas, A. et al., Cellular and Molecular Immunology 3rd ed., "T Lymphocyte Antigen Recognition and Activation", pp. 139–170 (1997).

Hurtado, J. et al., Journal of Immunology, "Potential Role of 4–1BB in T Cell Activation", vol. 155, pp. 3360–3367 (1995).

Futagawa, T. et al., International Immunology, "Expression and Function of 4–1BB and 4–1BB Ligand on Murine Dendritic Cells", vol. 14, No. 3, pp. 275–286 (2002).

Wilcox, R. et al., Journal of Immunology, "Cutting Edge: Expression of Functional CD137 Receptor by Dendritic Cells", vol. 168, pp. 4262–4267 (2002).

(Continued)

*Primary Examiner*—Long V. Le
*Assistant Examiner*—Jacob Cheu
(74) *Attorney, Agent, or Firm*—Paul D. Golian

(57) ABSTRACT

A humanized antibody that binds to human 4-1BB and that allows binding of human 4-1BB to a human 4-1BB ligand. In one aspect, the antibody is an IgG4 antibody. Also provided is a method for treating cancer in a subject comprising administering a therapeutically effective amount of the antibody to said subject.

5 Claims, 25 Drawing Sheets

OTHER PUBLICATIONS

Lindstedt, M. et al., Scandinavian Journal of Immunology, "Expression of CD137 (4–1BB) on Human Follicular Dendritic Cells", vol. 57, pp. 305–310 (2003).

Pollock, K. et al., The Journal of Immunology, "Inducible T Cell Antigen 4–1BB", vol. 150, No. 3, pp. 771–781 (1993).

Vinay, D. et al., Seminars in Immunology, "Role of 4–1BB in Immune Responses", vol. 10, pp. 481–489 (1998).

Hurtado, J. et al., Journal of Immunology, "Signals Through 4–1BB Are Costimulatory to Previously Activated Splenic T Cells and Inhibit Activation–Induced Cell Death", vol. 158, pp. 2600–2609 (1997).

Takahashi, C. et al., Journal of Immunology, "Cutting Edge: 4–1BB Is a Bona Fide CD8 T Cell Survival Signal", vol. 162, pp. 5037–5040 (1999).

Alderson, M. et al., Eur. J. Immunol., "Molecular and Biological Characterization of Human 4–1BB and It's Ligand", vol. 24, pp. 2219–2227 (1994).

DeBenedette, M. et al., Journal of Immunology, "Costimulation of CD28 T Lymphocytes by 4–1BB Ligand", vol. 158, pp. 551–559 (1997).

Salih, H. et al., Journal of Immunology, "Constitutive Expression of Functional 4–1BB (CD137) Ligand on Carcinoma Cells", vol. 165, pp. 2903–2910 (2000).

Melero, I. et al., Nature Medicine, "Monoclonal Antibodies Against the 4–1BB T–Cell Activation Molecule Eradicate Established Tumors", vol. 3, No. 6, pp. 682–685 (1997).

Wilcox, R. et al., The Journal of Clinical Investigation, "Provision of Antigen and CD137 Signalling Breaks Immunological Ignorance, Promoting Regression of Poorly Immunogenic Tumors", vol. 109, No. 5, pp. 651–659 (2002).

Wilcox, R. et al., Cancer Research, "Impaired Infiltration of Tumor Specific Cytolytic T Cells in the Absence of Interferon–γ Despite Their Normal Maturation in Lymphoid Organs During CD137 Monoclonal Antibody Therapy", vol. 62, ogs. 4413–4418 (2002).

Miller, R. et al., The Journal of Immunology, "4–1BB Specific Monoclonal Antibody Promotes the Generation of Tumor–Specific Immune Responses by Direct Aviation of CD8 T Cells in a CD40– Dependent Manner", vol. 19, pp. 1792–1800 (2002).

Wen, T. et al., Journal of Immunology, 4–1BB Ligand Mediated Costimulation of Human T Cells Induces CD4 and CD8 T Cell Expansion, Cytokine Production, and the Development of Cytolytic Effector Function:, vol. 168, pp. 4897–4906 (2002).

Hong, H. et al., Journal of Immunotherapy, "A Humanized Anti–4–1–BB Monoclonal Antibody Suppresses Antigen–Induced Humoral Immune Response in Nonhuman Primates", vol. 23, No. 6, pp. 613–621 (2000).

Jones, P. et al., Nature, "Replacing the Complementarity–Determining Regions in a Human Antibody With Those From a Mouse", vol. 321, pp. 522–525 (1986).

Foote, J. et al., J. Mol. Biol., "Antibody Framework Residues Affecting the Conformation of the Hypervariable Loops", vol. 224, pp. 487–499 (1992).

Kearney, J. et al., Journal of Immunology, "A New Mouse Myeloma Cell Line That Has Lost Immunoglobulin Expression But Permits the Construction of Antibody–Secreting Hybrid Cell Lines" vol. 123, No. 4, pp. 1548–1550 (1979).

Angal, S. et al., Molecular Immunology, "A Single Amino Acid Substitution Abolishes The Heterogeneity of Chimeric Mouse/Human (IgG4) Antibody", vol. 30, No. 1, pp. 105–108 (1993).

Saiki, R. et al., Science, "Primer–Directed Enzymatic Amplifications of DNA With A Thermostable DNA Polymerase", vol. 239, pp. 487–491 (1987).

Loh, E. et al., Science, "Polymerase Chain Reaction With Single–Sided Specificity: Analysis of T Cell Receptor δ Chain", vol. 243, pp. 217–220 (1989).

Chothia, C. et al., J. Mol. Biol., "Canonical Structures for the Hypervariable Regions of Immunoglobulins", vol. 196, pp. 901–917 (1987).

Lesk, A. et al., Antibody Engineering, A Practical Guide, "Antibody Structure and Structural Predictions Useful in Guiding Antibody Engineering", pp. 1–38 (1992).

Lane, R., Journal of Immunological Methods, "A Short–Duration Polyethylene Glycol Fusion Technique for Increasing Production of Monoclonal Antibody–Secreting Hybridomas" vol. 81, pp. 223–228 (1985).

```
  1  CGATGTACGG GCCAGATATA CGCGTTGACA TTGATTATTG ACTAGTTATT
     GCTACATGCC CGGTCTATAT GCGCAACTGT AACTAATAAC TGATCAATAA
 51  AATAGTAATC AATTACGGGG TCATTAGTTC ATAGCCCATA TATGGAGTTC
     TTATCATTAG TTAATGCCCC AGTAATCAAG TATCGGGTAT ATACCTCAAG
101  CGCGTTACAT AACTTACGGT AAATGGCCCG CCTGGCTGAC CGCCCAACGA
     GCGCAATGTA TTGAATGCCA TTTACCGGGC GGACCGACTG GCGGGTTGCT
151  CCCCCGCCCA TTGACGTCAA TAATGACGTA TGTTCCCATA GTAACGCCAA
     GGGGGCGGGT AACTGCAGTT ATTACTGCAT ACAAGGGTAT CATTGCGGTT
201  TAGGGACTTT CCATTGACGT CAATGGGTGG ACTATTTACG GTAAACTGCC
     ATCCCTGAAA GGTAACTGCA GTTACCCACC TGATAAATGC CATTTGACGG
251  CACTTGGCAG TACATCAAGT GTATCATATG CCAAGTACGC CCCCTATTGA
     GTGAACCGTC ATGTAGTTCA CATAGTATAC GGTTCATGCG GGGGATAACT
301  CGTCAATGAC GGTAAATGGC CCGCCTGGCA TTATGCCCAG TACATGACCT
     GCAGTTACTG CCATTTACCG GGCGGACCGT AATACGGGTC ATGTACTGGA
351  TATGGGACTT TCCTACTTGG CAGTACATCT ACGTATTAGT CATCGCTATT
     ATACCCTGAA AGGATGAACC GTCATGTAGA TGCATAATCA GTAGCGATAA
401  ACCATGGTGA TGCGGTTTTG GCAGTACATC AATGGGCGTG GATAGCGGTT
     TGGTACCACT ACGCCAAAAC CGTCATGTAG TTACCCGCAC CTATCGCCAA
451  TGACTCACGG GGATTTCCAA GTCTCCACCC CATTGACGTC AATGGGAGTT
     ACTGAGTGCC CCTAAAGGTT CAGAGGTGGG GTAACTGCAG TTACCCTCAA
501  TGTTTTGGCA CCAAAATCAA CGGGACTTTC CAAAATGTCG TAACAACTCC
     ACAAAACCGT GGTTTTAGTT GCCCTGAAAG GTTTTACAGC ATTGTTGAGG
551  GCCCCATTGA CGCAAATGGG CGGTAGGCGT GTACGGTGGG AGGTCTATAT
     CGGGGTAACT GCGTTTACCC GCCATCCGCA CATGCCACCC TCCAGATATA
601  AAGCAGAGCT CTCTGGCTAA CTAGAGAACC CACTGCTTAC TGGCTTATCG
     TTCGTCTCGA GAGACCGATT GATCTCTTGG GTGACGAATG ACCGAATAGC
                                                 Chi220 Leader
                                                 ~~~~~~~~
                                             KpnI
                                             ~~~~~~~
                                                   M  D  W ·
651  AAATTAATAC GACTCACTAT AGGGAGACCC AAGCTTGGTA CCATGGACTG
     TTTAATTATG CTGAGTGATA TCCCTCTGGG TTCGAACCAT GGTACCTGAC
                         Chi220 Leader
     ~~~~~~~~~~~~~~~~~~~~~~~~~~~~~~~~~~~~~~~~~~~~~~~~~
          BamHI
          ~~~~~~~
     · T  W  R  I  L  F  L  V  A  A  A  T  G  A  H  S  E ·
701  GACCTGGAGG ATCCTCTTCT TGGTGGCAGC AGCAACAGGT GCCCACTCCG
     CTGGACCTCC TAGGAGAAGA ACCACCGTCG TCGTTGTCCA CGGGTGAGGC
     · V  Q  L  V  E  S  G  G  G  L  V  Q  P  G  G  S
751  AAGTACAACT GGTGGAGTCT GGAGGAGGTT TGGTGCAACC TGGGGGTTCT
     TTCATGTTGA CCACCTCAGA CCTCCTCCAA ACCACGTTGG ACCCCCAAGA
                                                 CDR1
                                              ~~~~~~~~~~~~
      L  R  L  S  C  A  A  S  G  F  T  F  S  D  Y  W  M ·
801  CTGCGACTCT CTTGTGCAGC CTCGGGATTC ACTTTCAGTG ACTACTGGAT
     GACGCTGAGA GAACACGTCG GAGCCCTAAG TGAAAGTCAC TGATGACCTA
     CDR1                                              CDR2
     ~~~~                                              ~~~~
     · S  W  V  R  Q  A  P  G  K  G  L  E  W  V  A  D  I ·
851  GAGCTGGGTT CGTCAGGCGC CTGGAAAGGG CCTGGAGTGG GTTGCAGATA
     CTCGACCCAA GCAGTCCGCG GACCTTTCCC GGACCTCACC CAACGTCTAT
```

FIG. 2A

```
                              CDR2
          ~~~~~~~~~~~~~~~~~~~~~~~~~~~~~~~~~~~~~~~~~~~~~~~~~~~
          · K  N  D   G  S  Y   T  N  Y  A   P  S  L   T  N  R
 901      TTAAAAATGA TGGCAGTTAC ACAAACTATG CACCATCCCT AACGAATCGA
          AATTTTTACT ACCGTCAATG TGTTTGATAC GTGGTAGGGA TTGCTTAGCT
                                                   PstI
                                                 ~~~~~~~
           F  T  I  S   R  D  N   A  K  N   S  L  Y  L   Q  M  N ·
 951      TTCACAATCT CCAGAGACAA TGCCAAGAAC TCCCTGTACC TGCAGATGAA
          AAGTGTTAGA GGTCTCTGTT ACGGTTCTTG AGGGACATGG ACGTCTACTT
                                                       CDR3
                                                     ~~~~~~~
          ·S  L  R   A  E  D  T   A  V  Y   Y  C  A   R  E  L  T ·
1001      CTCTCTGAGA GCTGAGGACA CAGCCGTTTA TTACTGTGCT AGAGAACTAA
          GAGAGACTCT CGACTCCTGT GTCGGCAAAT AATGACACGA TCTCTTGATT
            CDR3
          ~~~~~~~~
                                                        NheI
                                                       ~~~~~~
          · G  T  W   G  Q  G   T  M  V  T   V  S  S   A  S  T
1051      CTGGGACTTG GGGCCAAGGA ACCATGGTCA CAGTCTCCTC AGCTAGCACC
          GACCCTGAAC CCCGGTTCCT TGGTACCAGT GTCAGAGGAG TCGATCGTGG
           K  G  P  S   V  F  P   L  A  P   C  S  R  S   T  S  E ·
1101      AAGGGCCCAT CCGTCTTCCC CCTGGCGCCC TGCTCCAGGA GCACCTCCGA
          TTCCCGGGTA GGCAGAAGGG GGACCGCGGG ACGAGGTCCT CGTGGAGGCT
                                                          AgeI
                                                          ~~~~~
          ·S  T  A   A  L  G  C   L  V  K   D  Y  F   P  E  P  V ·
1151      GAGCACAGCC GCCCTGGGCT GCCTGGTCAA GGACTACTTC CCCGAACCGG
          CTCGTGTCGG CGGGACCCGA CGGACCAGTT CCTGATGAAG GGGCTTGGCC
          AgeI ·
          ~
          · T  V  S   W  N  S   G  A  L  T   S  G  V   H  T  F
1201      TGACGGTGTC GTGGAACTCA GGCGCCCTGA CCAGCGGCGT GCACACCTTC
          ACTGCCACAG CACCTTGAGT CCGCGGGACT GGTCGCCGCA CGTGTGGAAG
           P  A  V  L   Q  S  S   G  L  Y   S  L  S  S   V  V  T ·
1251      CCGGCTGTCC TACAGTCCTC AGGACTCTAC TCCCTCAGCA GCGTGGTGAC
          GGCCGACAGG ATGTCAGGAG TCCTGAGATG AGGGAGTCGT CGCACCACTG
          ·V  P  S   S  S  L  G   T  K  T   Y  T  C   N  V  D  H ·
1301      CGTGCCCTCC AGCAGCTTGG GCACGAAGAC CTACACCTGC AACGTAGATC
          GCACGGGAGG TCGTCGAACC CGTGCTTCTG GATGTGGACG TTGCATCTAG
          · K  P  S   N  T  K   V  D  K  R   V  E  S   K  Y  G
1351      ACAAGCCCAG CAACACCAAG GTGGACAAGA GAGTTGAGTC CAAATATGGT
          TGTTCGGGTC GTTGTGGTTC CACCTGTTCT CTCAACTCAG GTTTATACCA
           P  P  C  P   P  C  P   A  P  E   F  L  G  G   P  S  V ·
1401      CCACCTTGCC CACCTTGCCC AGCACCTGAG TTCCTGGGGG GACCATCAGT
          GGTGGAACGG GTGGAACGGG TCGTGGACTC AAGGACCCCC CTGGTAGTCA
          ·F  L  F   P  P  K  P   K  D  T   L  M  I   S  R  T  P ·
1451      CTTCCTGTTC CCCCCAAAAC CCAAGGACAC TCTCATGATC TCCCGGACCC
          GAAGGACAAG GGGGGTTTTG GGTTCCTGTG AGAGTACTAG AGGGCCTGGG
          · E  V  T   C  V  V   V  D  V  S   Q  E  D   P  E  V
1501      CTGAGGTCAC GTGCGTGGTG GTGGACGTGA GCCAGGAAGA CCCCGAGGTC
          GACTCCAGTG CACGCACCAC CACCTGCACT CGGTCCTTCT GGGGCTCCAG
           Q  F  N  W   Y  V  D   G  V  E   V  H  N  A   K  T  K ·
1551      CAGTTCAACT GGTACGTGGA TGGCGTGGAG GTGCATAATG CCAAGACAAA
          GTCAAGTTGA CCATGCACCT ACCGCACCTC CACGTATTAC GGTTCTGTTT
```

FIG. 2B

```
        SacII
        ~~~~~~
        ·P  R  E  E  Q  F  N  S  T  Y  R  V  V  S  V  L  T·
1601    GCCGCGGGAG GAGCAGTTCA ACAGCACGTA CCGTGTGGTC AGCGTCCTCA
        CGGCGCCCTC CTCGTCAAGT TGTCGTGCAT GGCACACCAG TCGCAGGAGT
        · V  L  H  Q  D  W  L  N  G  K  E  Y  K  C  K  V
1651    CCGTCCTGCA CCAGGACTGG CTGAACGGCA AGGAGTACAA GTGCAAGGTC
        GGCAGGACGT GGTCCTGACC GACTTGCCGT TCCTCATGTT CACGTTCCAG
         S  N  K  G  L  P  S  S  I  E  K  T  I  S  K  A  K·
1701    TCCAACAAAG GCCTCCCGTC CTCCATCGAG AAAACCATCT CCAAAGCCAA
        AGGTTGTTTC CGGAGGGCAG GAGGTAGCTC TTTTGGTAGA GGTTTCGGTT
        ·G  Q  P  R  E  P  Q  V  Y  T  L  P  P  S  Q  E  E·
1751    AGGGCAGCCC CGAGAGCCAC AGGTGTACAC CCTGCCCCCA TCCCAGGAGG
        TCCCGTCGGG GCTCTCGGTG TCCACATGTG GGACGGGGGT AGGGTCCTCC
        · M  T  K  N  Q  V  S  L  T  C  L  V  K  G  F  Y
1801    AGATGACCAA GAACCAGGTC AGCCTGACCT GCCTGGTCAA AGGCTTCTAC
        TCTACTGGTT CTTGGTCCAG TCGGACTGGA CGGACCAGTT TCCGAAGATG
         P  S  D  I  A  V  E  W  E  S  N  G  Q  P  E  N  N·
1851    CCCAGCGACA TCGCCGTGGA GTGGGAGAGC AATGGGCAGC CGGAGAACAA
        GGGTCGCTGT AGCGGCACCT CACCCTCTCG TTACCCGTCG GCCTCTTGTT
        ·Y  K  T  T  P  P  V  L  D  S  D  G  S  F  F  L  Y·
1901    CTACAAGACC ACGCCTCCCG TGCTGGACTC CGACGGCTCC TTCTTCCTCT
        GATGTTCTGG TGCGGAGGGC ACGACCTGAG GCTGCCGAGG AAGAAGGAGA
        · S  R  L  T  V  D  K  S  R  W  Q  E  G  N  V  F
1951    ACAGCAGGCT AACCGTGGAC AAGAGCAGGT GGCAGGAGGG GAATGTCTTC
        TGTCGTCCGA TTGGCACCTG TTCTCGTCCA CCGTCCTCCC CTTACAGAAG
         S  C  S  V  M  H  E  A  L  H  N  H  Y  T  Q  K  S·
2001    TCATGCTCCG TGATGCATGA GGCTCTGCAC AACCACTACA CACAGAAGAG
        AGTACGAGGC ACTACGTACT CCGAGACGTG TTGGTGATGT GTGTCTTCTC
                                         XbaI
                                        ~~~~~~~
        ·L  S  L  S  L  G  K
2051    CCTCTCCCTG TCTCTGGGTA AATGATCTAG AGGGCCCTAT TCTATAGTGT
        GGAGAGGGAC AGAGACCCAT TTACTAGATC TCCCGGGATA AGATATCACA
2101    CACCTAAATG CTAGAGCTCG CTGATCAGCC TCGACTGTGC CTTCTAGTTG
        GTGGATTTAC GATCTCGAGC GACTAGTCGG AGCTGACACG GAAGATCAAC
2151    CCAGCCATCT GTTGTTTGCC CCTCCCCCGT GCCTTCCTTG ACCCTGGAAG
        GGTCGGTAGA CAACAAACGG GGAGGGGGCA CGGAAGGAAC TGGGACCTTC
2201    GTGCCACTCC CACTGTCCTT TCCTAATAAA ATGAGGAAAT TGCATCGCAT
        CACGGTGAGG GTGACAGGAA AGGATTATTT TACTCCTTTA ACGTAGCGTA
2251    TGTCTGAGTA GGTGTCATTC TATTCTGGGG GGTGGGGTGG GGCAGGACAG
        ACAGACTCAT CCACAGTAAG ATAAGACCCC CCACCCCACC CCGTCCTGTC
2301    CAAGGGGGAG GATTGGGAAG ACAATAGCAG GCATGCTGGG GATGCGGTGG
        GTTCCCCCTC CTAACCCTTC TGTTATCGTC CGTACGACCC CTACGCCACC
2351    GCTCTATGGC TTCTGAGGCG GAAAGAACCA GCTGGGGCTC TAGGGGGTAT
        CGAGATACCG AAGACTCCGC CTTTCTTGGT CGACCCCGAG ATCCCCCATA
2401    CCCCACGCGC CCTGTAGCGG CGCATTAAGC GCGGCGGGTG TGGTGGTTAC
        GGGGTGCGCG GGACATCGCC GCGTAATTCG CGCCGCCCAC ACCACCAATG
2451    GCGCAGCGTG ACCGCTACAC TTGCCAGCGC CCTAGCGCCC GCTCCTTTCG
        CGCGTCGCAC TGGCGATGTG AACGGTCGCG GGATCGCGGG CGAGGAAAGC
2501    CTTTCTTCCC TTCCTTTCTC GCCACGTTCG CCGGGCCTCT CAAAAAAGGG
        GAAAGAAGGG AAGGAAAGAG CGGTGCAAGC GGCCCGGAGA GTTTTTTCCC
2551    AAAAAAAGCA TGCATCTCAA TTAGTCAGCA ACCATAGTCC CGCCCCTAAC
        TTTTTTTCGT ACGTAGAGTT AATCAGTCGT TGGTATCAGG GCGGGGATTG
2601    TCCGCCCATC CCGCCCCTAA CTCCGCCCAG TTCCGCCCAT TCTCCGCCCC
        AGGCGGGTAG GGCGGGGATT GAGGCGGGTC AAGGCGGGTA AGAGGCGGGG
```

FIG. 2C

```
2651  ATGGCTGACT AATTTTTTTT ATTTATGCAG AGGCCGAGGC CGCCTCGGCC
      TACCGACTGA TTAAAAAAAA TAAATACGTC TCCGGCTCCG GCGGAGCCGG
2701  TCTGAGCTAT TCCAGAAGTA GTGAGGAGGC TTTTTTGGAG GCCTAGGCTT
      AGACTCGATA AGGTCTTCAT CACTCCTCCG AAAAAACCTC CGGATCCGAA
2751  TTGCAAAAAG CTTGGACAGC TCAGGGCTGC GATTTCGCGC CAAACTTGAC
      AACGTTTTTC GAACCTGTCG AGTCCCGACG CTAAAGCGCG GTTTGAACTG
2801  GGCAATCCTA GCGTGAAGGC TGGTAGGATT TTATCCCCGC TGCCATCATG
      CCGTTAGGAT CGCACTTCCG ACCATCCTAA AATAGGGGCG ACGGTAGTAC
2851  GTTCGACCAT TGAACTGCAT CGTCGCCGTG TCCCAAAATA TGGGGATTGG
      CAAGCTGGTA ACTTGACGTA GCAGCGGCAC AGGGTTTTAT ACCCCTAACC
2901  CAAGAACGGA GACCTACCCT GGCCTCCGCT CAGGAACGAG TTCAAGTACT
      GTTCTTGCCT CTGGATGGGA CCGGAGGCGA GTCCTTGCTC AAGTTCATGA
2951  TCCAAAGAAT GACCACAACC TCTTCAGTGG AAGGTAAACA GAATCTGGTG
      AGGTTTCTTA CTGGTGTTGG AGAAGTCACC TTCCATTTGT CTTAGACCAC
3001  ATTATGGGTA GGAAAACCTG GTTCTCCATT CCTGAGAAGA ATCGACCTTT
      TAATACCCAT CCTTTTGGAC CAAGAGGTAA GGACTCTTCT TAGCTGGAAA
3051  AAAGGACAGA ATTAATATAG TTCTCAGTAG AGAACTCAAA GAACCACCAC
      TTTCCTGTCT TAATTATATC AAGAGTCATC TCTTGAGTTT CTTGGTGGTG
3101  GAGGAGCTCA TTTTCTTGCC AAAAGTTTGG ATGATGCCTT AAGACTTATT
      CTCCTCGAGT AAAAGAACGG TTTTCAAACC TACTACGGAA TTCTGAATAA
3151  GAACAACCGG AATTGGCAAG TAAAGTAGAC ATGGTTTGGA TAGTCGGAGG
      CTTGTTGGCC TTAACCGTTC ATTTCATCTG TACCAAACCT ATCAGCCTCC
3201  CAGTTCTGTT TACCAGGAAG CCATGAATCA ACCAGGCCAC CTTAGACTCT
      GTCAAGACAA ATGGTCCTTC GGTACTTAGT TGGTCCGGTG GAATCTGAGA
3251  TTGTGACAAG GATCATGCAG GAATTTGAAA GTGACACGTT TTTCCCAGAA
      AACACTGTTC CTAGTACGTC CTTAAACTTT CACTGTGCAA AAAGGGTCTT
3301  ATTGATTTGG GGAAATATAA ACTTCTCCCA GAATACCCAG GCGTCCTCTC
      TAACTAAACC CCTTTATATT TGAAGAGGGT CTTATGGGTC CGCAGGAGAG
3351  TGAGGTCCAG GAGGAAAAAG GCATCAAGTA TAAGTTTGAA GTCTACGAGA
      ACTCCAGGTC CTCCTTTTTC CGTAGTTCAT ATTCAAACTT CAGATGCTCT
3401  AGAAAGACTA ACAGGAAGAT GCTTTCAAGT TCTCTGCTCC CCTCCTAAAG
      TCTTTCTGAT TGTCCTTCTA CGAAAGTTCA AGAGACGAGG GGAGGATTTC
3451  CTATGCATTT TTATAAGACC ATGGGACTTT TGCTGGCTTT AGATCTCTTT
      GATACGTAAA AATATTCTGG TACCCTGAAA ACGACCGAAA TCTAGAGAAA
3501  GTGAAGGAAC CTTACTTCTG TGGTGTGACA TAATTGGACA AACTACCTAC
      CACTTCCTTG GAATGAAGAC ACCACACTGT ATTAACCTGT TTGATGGATG
3551  AGAGATTTAA AGCTCTAAGG TAAATATAAA ATTTTTAAGT GTATAATGTG
      TCTCTAAATT TCGAGATTCC ATTTATATTT TAAAAATTCA CATATTACAC
3601  TTAAACTACT GATTCTAATT GTTTGTGTAT TTTAGATTCC AACCTATGGA
      AATTTGATGA CTAAGATTAA CAAACACATA AAATCTAAGG TTGGATACCT
3651  ACTGATGAAT GGGAGCAGTG GTGGAATGCC TTTAATGAGG AAAACCTGTT
      TGACTACTTA CCCTCGTCAC CACCTTACGG AAATTACTCC TTTTGGACAA
3701  TTGCTCAGAA GAAATGCCAT CTAGTGATGA TGAGGCTACT GCTGACTCTC
      AACGAGTCTT CTTTACGGTA GATCACTACT ACTCCGATGA CGACTGAGAG
3751  AACATTCTAC TCCTCCAAAA AAGAAGAGAA AGGTAGAAGA CCCCAAGGAC
      TTGTAAGATG AGGAGGTTTT TTCTTCTCTT TCCATCTTCT GGGGTTCCTG
3801  TTTCCTTCAG AATTGCTAAG TTTTTTGAGT CATGCTGTGT TTAGTAATAG
      AAAGGAAGTC TTAACGATTC AAAAAACTCA GTACGACACA AATCATTATC
3851  AACTCTTGCT TGCTTTGCTA TTTACACCAC AAAGGAAAAA GCTGCACTGC
      TTGAGAACGA ACGAAACGAT AAATGTGGTG TTTCCTTTTT CGACGTGACG
3901  TATACAAGAA AATTATGGAA AAATATTCTG TAACCTTTAT AAGTAGGCAT
      ATATGTTCTT TTAATACCTT TTTATAAGAC ATTGGAAATA TTCATCCGTA
3951  AACAGTTATA ATCATAACAT ACTGTTTTTT CTTACTCCAC ACAGGCATAG
      TTGTCAATAT TAGTATTGTA TGACAAAAAA GAATGAGGTG TGTCCGTATC
4001  AGTGTCTGCT ATTAATAACT ATGCTCAAAA ATTGTGTACC TTTAGCTTTT
      TCACAGACGA TAATTATTGA TACGAGTTTT TAACACATGG AAATCGAAAA
```

FIG. 2D

4051 TAATTTGTAA AGGGGTTAAT AAGGAATATT TGATGTATAG TGCCTTGACT
ATTAAACATT TCCCCAATTA TTCCTTATAA ACTACATATC ACGGAACTGA
4101 AGAGATCATA ATCAGCCATA CCACATTTGT AGAGGTTTTA CTTGCTTTAA
TCTCTAGTAT TAGTCGGTAT GGTGTAAACA TCTCCAAAAT GAACGAAATT
4151 AAAACCTCCC ACACCTCCCC CTGAACCTGA AACATAAAAT GAATGCAATT
TTTTGGAGGG TGTGGAGGGG GACTTGGACT TTGTATTTTA CTTACGTTAA
4201 GTTGTTGTTA ACTTGTTTAT TGCAGCTTAT AATGGTTACA AATAAAGCAA
CAACAACAAT TGAACAAATA ACGTCGAATA TTACCAATGT TTATTTCGTT
4251 TAGCATCACA AATTTCACAA ATAAAGCATT TTTTTCACTG CATTCTAGTT
ATCGTAGTGT TTAAAGTGTT TATTTCGTAA AAAAAGTGAC GTAAGATCAA
4301 GTGGTTTGTC CAAACTCATC AATGTATCTT ATCATGTCTG GATCGGCTGG
CACCAAACAG GTTTGAGTAG TTACATAGAA TAGTACAGAC CTAGCCGACC
4351 ATGATCCTCC AGCGCGGGGA TCTCATGCTG GAGTTCTTCG CCCACCCCAA
TACTAGGAGG TCGCGCCCCT AGAGTACGAC CTCAAGAAGC GGGTGGGGTT
4401 CTTGTTTATT GCAGCTTATA ATGGTTACAA ATAAAGCAAT AGCATCACAA
GAACAAATAA CGTCGAATAT TACCAATGTT TATTTCGTTA TCGTAGTGTT
4451 ATTTCACAAA TAAAGCATTT TTTTCACTGC ATTCTAGTTG TGGTTTGTCC
TAAAGTGTTT ATTTCGTAAA AAAAGTGACG TAAGATCAAC ACCAAACAGG
4501 AAACTCATCA ATGTATCTTA TCATGTCTGT ATACCGTCGA CCTCTAGCTA
TTTGAGTAGT TACATAGAAT AGTACAGACA TATGGCAGCT GGAGATCGAT
4551 GAGCTTGGCG TAATCATGGT CATAGCTGTT TCCTGTGTGA AATTGTTATC
CTCGAACCGC ATTAGTACCA GTATCGACAA AGGACACACT TTAACAATAG
4601 CGCTCACAAT TCCACACAAC ATACGAGCCG GAAGCATAAA GTGTAAAGCC
GCGAGTGTTA AGGTGTGTTG TATGCTCGGC CTTCGTATTT CACATTTCGG
4651 TGGGGTGCCT AATGAGTGAG CTAACTCACA TTAATTGCGT TGCGCTCACT
ACCCCACGGA TTACTCACTC GATTGAGTGT AATTAACGCA ACGCGAGTGA
4701 GCCCGCTTTC CAGTCGGGAA ACCTGTCGTG CCAGCTGCAT TAATGAATCG
CGGGCGAAAG GTCAGCCCTT TGGACAGCAC GGTCGACGTA ATTACTTAGC
4751 GCCAACGCGC GGGGAGAGGC GGTTTGCGTA TTGGGCGCTC TTCCGCTTCC
CGGTTGCGCG CCCCTCTCCG CCAAACGCAT AACCCGCGAG AAGGCGAAGG
4801 TCGCTCACTG ACTCGCTGCG CTCGGTCGTT CGGCTGCGGC GAGCGGTATC
AGCGAGTGAC TGAGCGACGC GAGCCAGCAA GCCGACGCCG CTCGCCATAG
4851 AGCTCACTCA AAGGCGGTAA TACGGTTATC CACAGAATCA GGGGATAACG
TCGAGTGAGT TTCCGCCATT ATGCCAATAG GTGTCTTAGT CCCCTATTGC
4901 CAGGAAAGAA CATGTGAGCA AAAGGCCAGC AAAAGGCCAG GAACCGTAAA
GTCCTTTCTT GTACACTCGT TTTCCGGTCG TTTTCCGGTC CTTGGCATTT
4951 AAGGCCGCGT TGCTGGCGTT TTTCCATAGG CTCCGCCCCC CTGACGAGCA
TTCCGGCGCA ACGACCGCAA AAAGGTATCC GAGGCGGGGG GACTGCTCGT
5001 TCACAAAAAT CGACGCTCAA GTCAGAGGTG GCGAAACCCG ACAGGACTAT
AGTGTTTTTA GCTGCGAGTT CAGTCTCCAC CGCTTTGGGC TGTCCTGATA
5051 AAAGATACCA GGCGTTTCCC CCTGGAAGCT CCCTCGTGCG CTCTCCTGTT
TTTCTATGGT CCGCAAAGGG GGACCTTCGA GGGAGCACGC GAGAGGACAA
5101 CCGACCCTGC CGCTTACCGG ATACCTGTCC GCCTTTCTCC CTTCGGGAAG
GGCTGGGACG GCGAATGGCC TATGGACAGG CGGAAAGAGG GAAGCCCTTC
5151 CGTGGCGCTT TCTCAATGCT CACGCTGTAG GTATCTCAGT TCGGTGTAGG
GCACCGCGAA AGAGTTACGA GTGCGACATC CATAGAGTCA AGCCACATCC
5201 TCGTTCGCTC CAAGCTGGGC TGTGTGCACG AACCCCCCGT TCAGCCCGAC
AGCAAGCGAG GTTCGACCCG ACACACGTGC TTGGGGGGCA AGTCGGGCTG
5251 CGCTGCGCCT TATCCGGTAA CTATCGTCTT GAGTCCAACC CGGTAAGACA
GCGACGCGGA ATAGGCCATT GATAGCAGAA CTCAGGTTGG GCCATTCTGT
5301 CGACTTATCG CCACTGGCAG CAGCCACTGG TAACAGGATT AGCAGAGCGA
GCTGAATAGC GGTGACCGTC GTCGGTGACC ATTGTCCTAA TCGTCTCGCT
5351 GGTATGTAGG CGGTGCTACA GAGTTCTTGA AGTGGTGGCC TAACTACGGC
CCATACATCC GCCACGATGT CTCAAGAACT TCACCACCGG ATTGATGCCG
5401 TACACTAGAA GGACAGTATT TGGTATCTGC GCTCTGCTGA AGCCAGTTAC
ATGTGATCTT CCTGTCATAA ACCATAGACG CGAGACGACT TCGGTCAATG

FIG. 2E

```
5451  CTTCGGAAAA AGAGTTGGTA GCTCTTGATC CGGCAAACAA ACCACCGCTG
      GAAGCCTTTT TCTCAACCAT CGAGAACTAG GCCGTTTGTT TGGTGGCGAC
5501  GTAGCGGTGG TTTTTTTGTT TGCAAGCAGC AGATTACGCG CAGAAAAAAA
      CATCGCCACC AAAAAAACAA ACGTTCGTCG TCTAATGCGC GTCTTTTTTT
5551  GGATCTCAAG AAGATCCTTT GATCTTTTCT ACGGGGTCTG ACGCTCAGTG
      CCTAGAGTTC TTCTAGGAAA CTAGAAAAGA TGCCCCAGAC TGCGAGTCAC
5601  GAACGAAAAC TCACGTTAAG GGATTTTGGT CATGAGATTA TCAAAAAGGA
      CTTGCTTTTG AGTGCAATTC CCTAAAACCA GTACTCTAAT AGTTTTTCCT
5651  TCTTCACCTA GATCCTTTTA AATTAAAAAT GAAGTTTTAA ATCAATCTAA
      AGAAGTGGAT CTAGGAAAAT TTAATTTTTA CTTCAAAATT TAGTTAGATT
5701  AGTATATATG AGTAAACTTG GTCTGACAGT TACCAATGCT TAATCAGTGA
      TCATATATAC TCATTTGAAC CAGACTGTCA ATGGTTACGA ATTAGTCACT
5751  GGCACCTATC TCAGCGATCT GTCTATTTCG TTCATCCATA GTTGCCTGAC
      CCGTGGATAG AGTCGCTAGA CAGATAAAGC AAGTAGGTAT CAACGGACTG
5801  TCCCCGTCGT GTAGATAACT ACGATACGGG AGGGCTTACC ATCTGGCCCC
      AGGGGCAGCA CATCTATTGA TGCTATGCCC TCCCGAATGG TAGACCGGGG
5851  AGTGCTGCAA TGATACCGCG AGACCCACGC TCACCGGCTC CAGATTTATC
      TCACGACGTT ACTATGGCGC TCTGGGTGCG AGTGGCCGAG GTCTAAATAG
5901  AGCAATAAAC CAGCCAGCCG GAAGGGCCGA GCGCAGAAGT GGTCCTGCAA
      TCGTTATTTG GTCGGTCGGC CTTCCCGGCT CGCGTCTTCA CCAGGACGTT
5951  CTTTATCCGC CTCCATCCAG TCTATTAATT GTTGCCGGGA AGCTAGAGTA
      GAAATAGGCG GAGGTAGGTC AGATAATTAA CAACGGCCCT TCGATCTCAT
6001  AGTAGTTCGC CAGTTAATAG TTTGCGCAAC GTTGTTGCCA TTGCTACAGG
      TCATCAAGCG GTCAATTATC AAACGCGTTG CAACAACGGT AACGATGTCC
6051  CATCGTGGTG TCACGCTCGT CGTTTGGTAT GGCTTCATTC AGCTCCGGTT
      GTAGCACCAC AGTGCGAGCA GCAAACCATA CCGAAGTAAG TCGAGGCCAA
6101  CCCAACGATC AAGGCGAGTT ACATGATCCC CCATGTTGTG CAAAAAAGCG
      GGGTTGCTAG TTCCGCTCAA TGTACTAGGG GGTACAACAC GTTTTTTCGC
6151  GTTAGCTCCT TCGGTCCTCC GATCGTTGTC AGAAGTAAGT TGGCCGCAGT
      CAATCGAGGA AGCCAGGAGG CTAGCAACAG TCTTCATTCA ACCGGCGTCA
6201  GTTATCACTC ATGGTTATGG CAGCACTGCA TAATTCTCTT ACTGTCATGC
      CAATAGTGAG TACCAATACC GTCGTGACGT ATTAAGAGAA TGACAGTACG
6251  CATCCGTAAG ATGCTTTTCT GTGACTGGTG AGTACTCAAC CAAGTCATTC
      GTAGGCATTC TACGAAAAGA CACTGACCAC TCATGAGTTG GTTCAGTAAG
6301  TGAGAATAGT GTATGCGGCG ACCGAGTTGC TCTTGCCCGG CGTCAATACG
      ACTCTTATCA CATACGCCGC TGGCTCAACG AGAACGGGCC GCAGTTATGC
6351  GGATAATACC GCGCCACATA GCAGAACTTT AAAAGTGCTC ATCATTGGAA
      CCTATTATGG CGCGGTGTAT CGTCTTGAAA TTTTCACGAG TAGTAACCTT
6401  AACGTTCTTC GGGGCGAAAA CTCTCAAGGA TCTTACCGCT GTTGAGATCC
      TTGCAAGAAG CCCCGCTTTT GAGAGTTCCT AGAATGGCGA CAACTCTAGG
6451  AGTTCGATGT AACCCACTCG TGCACCCAAC TGATCTTCAG CATCTTTTAC
      TCAAGCTACA TTGGGTGAGC ACGTGGGTTG ACTAGAAGTC GTAGAAAATG
6501  TTTCACCAGC GTTTCTGGGT GAGCAAAAAC AGGAAGGCAA AATGCCGCAA
      AAAGTGGTCG CAAAGACCCA CTCGTTTTTG TCCTTCCGTT TTACGGCGTT
6551  AAAAGGGAAT AAGGGCGACA CGGAAATGTT GAATACTCAT ACTCTTCCTT
      TTTTCCCTTA TTCCCGCTGT GCCTTTACAA CTTATGAGTA TGAGAAGGAA
6601  TTTCAATATT ATTGAAGCAT TTATCAGGGT TATTGTCTCA TGAGCGGATA
      AAAGTTATAA TAACTTCGTA AATAGTCCCA ATAACAGAGT ACTCGCCTAT
6651  CATATTTGAA TGTATTTAGA AAAATAAACA AATAGGGGTT CCGCGCACAT
      GTATAAACTT ACATAAATCT TTTTATTTGT TTATCCCCAA GGCGCGTGTA
6701  TTCCCCGAAA AGTGCCACCT GACGTCGACG GATCGGGAGA TCTGCTAGGT
      AAGGGGCTTT TCACGGTGGA CTGCAGCTGC CTAGCCCTCT AGACGATCCA
                  AscI
                ~~~~~~~~~
6751  GACCTGAGGC GCGCCGGCTT CGAATAGCCA GAGTAACCTT TTTTTTTAAT
      CTGGACTCCG CGCGGCCGAA GCTTATCGGT CTCATTGGAA AAAAAAATTA
```

FIG. 2F

```
6801  TTTATTTTAT TTTATTTTTG AGATGGAGTT TGGCGCCGAT CTCCCGATCC
      AAATAAAATA AAATAAAAAC TCTACCTCAA ACCGCGGCTA GAGGGCTAGG
6851  CCTATGGTCG ACTCTCAGTA CAATCTGCTC TGATGCCGCA TAGTTAAGCC
      GGATACCAGC TGAGAGTCAT GTTAGACGAG ACTACGGCGT ATCAATTCGG
6901  AGTATCTGCT CCCTGCTTGT GTGTTGGAGG TCGCTGAGTA GTGCGCGAGC
      TCATAGACGA GGGACGAACA CACAACCTCC AGCGACTCAT CACGCGCTCG
6951  AAAATTTAAG CTACAACAAG GCAAGGCTTG ACCGACAATT GCATGAAGAA
      TTTTAAATTC GATGTTGTTC CGTTCCGAAC TGGCTGTTAA CGTACTTCTT
7001  TCTGCTTAGG GTTAGGCGTT TTGCGCTGCT TCG
      AGACGAATCC CAATCCGCAA AACGCGACGA AGC
```

FIG. 2G

```
  1   AATTACGGGG TCATTAGTTC ATAGCCCATA TATGGAGTTC CGCGTTACAT
      TTAATGCCCC AGTAATCAAG TATCGGGTAT ATACCTCAAG GCGCAATGTA
 51   AACTTACGGT AAATGGCCCG CCTGGCTGAC CGCCCAACGA CCCCCGCCCA
      TTGAATGCCA TTTACCGGGC GGACCGACTG GCGGGTTGCT GGGGGCGGGT
101   TTGACGTCAA TAATGACGTA TGTTCCCATA GTAACGCCAA TAGGGACTTT
      AACTGCAGTT ATTACTGCAT ACAAGGGTAT CATTGCGGTT ATCCCTGAAA
151   CCATTGACGT CAATGGGTGG ACTATTTACG GTAAACTGCC CACTTGGCAG
      GGTAACTGCA GTTACCCACC TGATAAATGC CATTTGACGG GTGAACCGTC
201   TACATCAAGT GTATCATATG CCAAGTACGC CCCCTATTGA CGTCAATGAC
      ATGTAGTTCA CATAGTATAC GGTTCATGCG GGGGATAACT GCAGTTACTG
251   GGTAAATGGC CCGCCTGGCA TTATGCCCAG TACATGACCT TATGGGACTT
      CCATTTACCG GGCGGACCGT AATACGGGTC ATGTACTGGA ATACCCTGAA
301   TCCTACTTGG CAGTACATCT ACGTATTAGT CATCGCTATT ACCATGGTGA
      AGGATGAACC GTCATGTAGA TGCATAATCA GTAGCGATAA TGGTACCACT
351   TGCGGTTTTG GCAGTACATC AATGGGCGTG GATAGCGGTT TGACTCACGG
      ACGCCAAAAC CGTCATGTAG TTACCCGCAC CTATCGCCAA ACTGAGTGCC
401   GGATTTCCAA GTCTCCACCC CATTGACGTC AATGGGAGTT TGTTTTGGCA
      CCTAAAGGTT CAGAGGTGGG GTAACTGCAG TTACCCTCAA ACAAAACCGT
451   CCAAAATCAA CGGGACTTTC CAAAATGTCG TAACAACTCC GCCCCATTGA
      GGTTTTAGTT GCCCTGAAAG GTTTTACAGC ATTGTTGAGG CGGGGTAACT
501   CGCAAATGGG CGGTAGGCGT GTACGGTGGG AGGTCTATAT AAGCAGAGCT
      GCGTTTACCC GCCATCCGCA CATGCCACCC TCCAGATATA TTCGTCTCGA
551   CTCTGGCTAA CTAGAGAACC CACTGCTTAC TGGCTTATCG AAATTAATAC
      GAGACCGATT GATCTCTTGG GTGACGAATG ACCGAATAGC TTTAATTATG
                                   KpnI
                                  ~~~~~~~
                                              M  E  A   P  A  Q
601   GACTCACTAT AGGGAGACCC AAGCTTGGTA CCATGGAAGC CCCAGCTCAG
      CTGAGTGATA TCCCTCTGGG TTCGAACCAT GGTACCTTCG GGGTCGAGTC
       L  L  F  L   L  L  L   W  L  P   D  T  T  G   D  I  V
651   CTTCTCTTCC TCCTGCTACT CTGGCTCCCA GATACCACCG GAGACATTGT
      GAAGAGAAGG AGGACGATGA GACCGAGGGT CTATGGTGGC CTCTGTAACA
      ·M  T  Q   S  P  D  S   L  A  V   S  L  G   E  R  A  T
701   AATGACCCAG TCTCCAGACT CCCTGGCTGT GTCACTAGGA GAGCGGGCCA
      TTACTGGGTC AGAGGTCTGA GGGACCGACA CAGTGATCCT CTCGCCCGGT
                                   CDR1
                           ~~~~~~~~~~~~~~~~~~~~~~~~~~~~~~~~~~~~~~~~~~~
      · I  N  C   K  S  S   Q  S  L  L   S  S  G   N  Q  K
751   CTATAAACTG CAAGTCCAGT CAGAGTCTTT TATCCAGTGG AAACCAAAAG
      GATATTTGAC GTTCAGGTCA GTCTCAGAAA ATAGGTCACC TTTGGTTTTC
        CDR1
      ~~~~~~~~~~~~~
       N  Y  L  A   W  Y  Q   Q  K  P   G  Q  P  P   K  L  L ·
801   AACTATTTGG CCTGGTATCA GCAGAAACCA GGCCAGCCTC CTAAACTACT
      TTGATAAACC GGACCATAGT CGTCTTTGGT CCGGTCGGAG GATTTGATGA
                   CDR2
              ~~~~~~~~~~~~~~~~~~~~~~~
      ·I  Y  Y   A  S  T  R   Q  S  G   V  P  D   R  F  S  G ·
851   GATCTACTAT GCATCCACTA GGCAATCAGG GGTCCCTGAT CGCTTCAGTG
      CTAGATGATA CGTAGGTGAT CCGTTAGTCC CCAGGGACTA GCGAAGTCAC
                                                   PstI
                                                  ~~~~~~
      · S  G  S   G  T  D   F  T  L  T   I  S  S   L  Q  A
901   GCAGTGGATC TGGGACGGAC TTCACTCTGA CCATCAGCAG CCTGCAGGCT
      CGTCACCTAG ACCCTGCCTG AAGTGAGACT GGTAGTCGTC GGACGTCCGA
```

FIG. 4A

```
                                                CDR3
                                   ~~~~~~~~~~~~~~~~~~~~~~~~~~~~~
                                    PstI          EcoRV
                                   ~~~~~~~       ~~~~~~~
          E  D  V  A   V  Y  Y   C  L  Q   Y  D  R  Y   P  F  T ·
 951     GAGGACGTGG CAGTCTATTA CTGCCTGCAG TATGACAGAT ATCCATTCAC
         CTCCTGCACC GTCAGATAAT GACGGACGTC ATACTGTCTA TAGGTAAGTG
         CDR3
         ~
                                                      XhoI    XbaI
                                                     ~~~~~~~  ~~~~
         · F  G  Q   G  T  K  L   E  I  K   R
1001     GTTCGGCCAA GGGACGAAGT TGGAAATAAA ACGTAAGTCT CGAGTCTCTA
         CAAGCCGGTT CCCTGCTTCA ACCTTTATTT TGCATTCAGA GCTCAGAGAT
              AgeI
             ~~~~~~~
         XbaI                  EcoRI
         ~~                    ~~~~~~
1051     GATAACCGGT CAATCGATTG GAATTCTAAA CTCTGAGGGG GTCGGATGAC
         CTATTGGCCA GTTAGCTAAC CTTAAGATTT GAGACTCCCC CAGCCTACTG
1101     GTGGCCATTC TTTGCCTAAA GCATTGAGTT TACTGCAAGG TCAGAAAAGC
         CACCGGTAAG AAACGGATTT CGTAACTCAA ATGACGTTCC AGTCTTTTCG
1151     ATGCAAAGCC CTCAGAATGG CTGCAAAGAG CTCCAACAAA ACAATTTAGA
         TACGTTTCGG GAGTCTTACC GACGTTTCTC GAGGTTGTTT TGTTAAATCT
1201     ACTTTATTAA GGAATAGGGG GAAGCTAGGA AGAAACTCAA AACATCAAGA
         TGAAATAATT CCTTATCCCC CTTCGATCCT TCTTTGAGTT TTGTAGTTCT
1251     TTTTAAATAC GCTTCTTGGT CTCCTTGCTA TAATTATCTG GGATAAGCAT
         AAAATTTATG CGAAGAACCA GAGGAACGAT ATTAATAGAC CCTATTCGTA
1301     GCTGTTTTCT GTCTGTCCCT AACATGCCCT GTGATTATCC GCAAACAACA
         CGACAAAAGA CAGACAGGGA TTGTACGGGA CACTAATAGG CGTTTGTTGT
1351     CACCCAAGGG CAGAACTTTG TTACTTAAAC ACCATCCTGT TTGCTTCTTT
         GTGGGTTCCC GTCTTGAAAC AATGAATTTG TGGTAGGACA AACGAAGAAA
                   T  V  A  A   P  S  V  F   I  F  P   P  S  D
1401     CCTCAGGAAC TGTGGCTGCA CCATCTGTCT TCATCTTCCC GCCATCTGAT
         GGAGTCCTTG ACACCGACGT GGTAGACAGA AGTAGAAGGG CGGTAGACTA
          E  Q  L  K   S  G  T   A  S  V   V  C  L  L   N  N  F
1451     GAGCAGTTGA AATCTGGAAC TGCCTCTGTT GTGTGCCTGC TGAATAACTT
         CTCGTCAACT TTAGACCTTG ACGGAGACAA CACACGGACG ACTTATTGAA
         · Y  P  R   E  A  K  V   Q  W  K   V  D  N   A  L  Q  S
1501     CTATCCCAGA GAGGCCAAAG TACAGTGGAA GGTGGATAAC GCCCTCCAAT
         GATAGGGTCT CTCCGGTTTC ATGTCACCTT CCACCTATTG CGGGAGGTTA
         ·  G  N  S   Q  E  S   V  T  E  Q   D  S  K   D  S  T
1551     CGGGTAACTC CCAGGAGAGT GTCACAGAGC AGGACAGCAA GGACAGCACC
         GCCCATTGAG GGTCCTCTCA CAGTGTCTCG TCCTGTCGTT CCTGTCGTGG
          Y  S  L  S   S  T  L   T  L  S   K  A  D  Y   E  K  H
1601     TACAGCCTCA GCAGCACCCT GACGCTGAGC AAAGCAGACT ACGAGAAACA
         ATGTCGGAGT CGTCGTGGGA CTGCGACTCG TTTCGTCTGA TGCTCTTTGT
         · K  V  Y   A  C  E  V   T  H  Q   G  L  S   S  P  V  T
1651     CAAAGTCTAC GCCTGCGAAG TCACCCATCA GGGCCTGAGC TCGCCCGTCA
         GTTTCAGATG CGGACGCTTC AGTGGGTAGT CCCGGACTCG AGCGGGCAGT
         ·  K  S  F   N  R  G   E  C
1701     CAAAGAGCTT CAACAGGGGA GAGTGTTAGA GGGAGAAGTG CCCCCACCTG
         GTTTCTCGAA GTTGTCCCCT CTCACAATCT CCCTCTTCAC GGGGGTGGAC
1751     CTCCTCAGTT CCAGCCTGAC CCCCTCCCAT CCTTTGGCCT CTGACCCTTT
         GAGGAGTCAA GGTCGGACTG GGGGAGGGTA GGAAACCGGA GACTGGGAAA
1801     TTCCACAGGG GACCTACCCC TATTGCGGTC CTCCAGCTCA TCTTTCACCT
         AAGGTGTCCC CTGGATGGGG ATAACGCCAG GAGGTCGAGT AGAAAGTGGA
```

FIG. 4B

```
1851  CACCCCCCTC CTCCTCCTTG GCTTTAATTA TGCTAATGTT GGAGGAGAAT
      GTGGGGGGAG GAGGAGGAAC CGAAATTAAT ACGATTACAA CCTCCTCTTA
1901  GAATAAATAA AGTGAATCTT TGCACCTGTG GTTTCTCTCT TTCCTCATTT
      CTTATTTATT TCACTTAGAA ACGTGGACAC CAAAGAGAGA AAGGAGTAAA
1951  AATAATTATT ATCTGTTGTT TTACCAACTA CTCAATTTCT CTTATAAGGG
      TTATTAATAA TAGACAACAA AATGGTTGAT GAGTTAAAGA GAATATTCCC
2001  ACTAAATATG TAGTCATCCT AAGGCGCATA ACCATTTATA AAAATCATCC
      TGATTTATAC ATCAGTAGGA TTCCGCGTAT TGGTAAATAT TTTTAGTAGG
2051  TTCATTCTAT TTTACCCTAT CATCCTCTGC AAGACAGTCC TCCCTCAAAC
      AAGTAAGATA AAATGGGATA GTAGGAGACG TTCTGTCAGG AGGGAGTTTG
2101  CCACAAGCCT TCTGTCCTCA CAGTCCCCTG GGCCATGGTA GGAGAGACTT
      GGTGTTCGGA AGACAGGAGT GTCAGGGGAC CCGGTACCAT CCTCTCTGAA
2151  GCTTCCTTGT TTTCCCCTCC TCAGCAAGCC CTCATAGTCC TTTTTAAGGG
      CGAAGGAACA AAAGGGGAGG AGTCGTTCGG GAGTATCAGG AAAAATTCCC
2201  TGACAGGTCT TACAGTCATA TATCCTTTGA TTCAATTCCC TGAGAATCAA
      ACTGTCCAGA ATGTCAGTAT ATAGGAAACT AAGTTAAGGG ACTCTTAGTT
2251  CCAAAGCAAA TTTTTCAAAA GAAGAAACCT GCTATAAAGA GAATCATTCA
      GGTTTCGTTT AAAAAGTTTT CTTCTTTGGA CGATATTTCT CTTAGTAAGT
2301  TTGCAACATG ATATAAAATA ACAACACAAT AAAAGCAATT AAATAAACAA
      AACGTTGTAC TATATTTTAT TGTTGTGTTA TTTTCGTTAA TTTATTTGTT
2351  ACAATAGGGA AATGTTTAAG TTCATCATGG TACTTAGACT TAATGGAATG
      TGTTATCCCT TTACAAATTC AAGTAGTACC ATGAATCTGA ATTACCTTAC
2401  TCATGCCTTA TTTACATTTT TAAACAGGTA CTGAGGGACT CCTGTCTGCC
      AGTACGGAAT AAATGTAAAA ATTTGTCCAT GACTCCCTGA GGACAGACGG
2451  AAGGGCCGTA TTGAGTACTT TCCACAACCT AATTTAATCC ACACTATACT
      TTCCCGGCAT AACTCATGAA AGGTGTTGGA TTAAATTAGG TGTGATATGA
2501  GTGAGATTAA AAACATTCAT TAAAATGTTG CAAAGGTTCT ATAAAGCTGA
      CACTCTAATT TTTGTAAGTA ATTTTACAAC GTTTCCAAGA TATTTCGACT
                                             XbaI
                                            ~~~~~~~
2551  GAGACAAATA TATTCTATAA CTCAGCAATC CCACTTCTAG ATGACTGAGT
      CTCTGTTTAT ATAAGATATT GAGTCGTTAG GGTGAAGATC TACTGACTCA
2601  GTCCCCACCC ACCAAAAAAC TATGCAAGAA TGTTCAAAGC AGCTTTATTT
      CAGGGGTGGG TGGTTTTTTG ATACGTTCTT ACAAGTTTCG TCGAAATAAA
2651  ACAAAAGCCA AAAATTGGAA ATAGCCCGAT TGTCCAACAA TAGAATGAGT
      TGTTTTCGGT TTTTAACCTT TATCGGGCTA ACAGGTTGTT ATCTTACTCA
2701  TATTAAACTG TGGTATGTTT ATACATTAGA ATACCCAATG AGGAGAATTA
      ATAATTTGAC ACCATACAAA TATGTAATCT TATGGGTTAC TCCTCTTAAT
2751  ACAAGCTACA ACTATACCTA CTCACACAGA TGAATCTCAT AAAAATAATG
      TGTTCGATGT TGATATGGAT GAGTGTGTCT ACTTAGAGTA TTTTTATTAC
2801  TTACATAAGA GAAACTCAAT GCAAAAGATA TGTTCTGTAT GTTTTCATCC
      AATGTATTCT CTTTGAGTTA CGTTTTCTAT ACAAGACATA CAAAAGTAGG
2851  ATATAAAGTT CAAAACCAGG TAAAAATAAA GTTAGAAATT TGGATGGAAA
      TATATTTCAA GTTTTGGTCC ATTTTTATTT CAATCTTTAA ACCTACCTTT
2901  TTACTCTTAG CTGGGGGTGG GCGAGTTAGT GCCTGGGAGA AGACAAGAAG
      AATGAGAATC GACCCCCACC CGCTCAATCA CGGACCCTCT TCTGTTCTTC
2951  GGGCTTCTGG GGTCTTGGTA ATGTTCTGTT CCTCGTGTGG GGTTGTGCAG
      CCCGAAGACC CCAGAACCAT TACAAGACAA GGAGCACACC CCAACACGTC
3001  TTATGATCTG TGCACTGTTC TGTATACACA TTATGCTTCA AAATAACTTC
      AATACTAGAC ACGTGACAAG ACATATGTGT AATACGAAGT TTTATTGAAG
3051  ACATAAAGAA CATCTTATAC CCAGTTAATA GATAGAAGAG GAATAAGTAA
      TGTATTTCTT GTAGAATATG GGTCAATTAT CTATCTTCTC CTTATTCATT
3101  TAGGTCAAGA CCACGCAGCT GGTAAGTGGG GGGGCCTGGG ATCAAATAGC
      ATCCAGTTCT GGTGCGTCGA CCATTCACCC CCCCGGACCC TAGTTTATCG
3151  TACCTGCCTA ATCCTGCCCT CTTGAGCCCT GAATGAGTCT GCCTTCCAGG
      ATGGACGGAT TAGGACGGGA GAACTCGGGA CTTACTCAGA CGGAAGGTCC
```

FIG. 4C

```
3201  GCTCAAGGTG CTCAACAAAA CAACAGGCCT GCTATTTTCC TGGCATCTGT
      CGAGTTCCAC GAGTTGTTTT GTTGTCCGGA CGATAAAAGG ACCGTAGACA
                  NheI
                 ~~~~~~
3251  GCCCTGTTTG GCTAGCTAGG AGCACACATA CATAGAAATT AAATGAAACA
      CGGGACAAAC CGATCGATCC TCGTGTGTAT GTATCTTTAA TTTACTTTGT
3301  GACCTTCAGC AAGGGGACAG AGGACAGAAT TAACCTTGCC CAGACACTGG
      CTGGAAGTCG TTCCCCTGTC TCCTGTCTTA ATTGGAACGG GTCTGTGACC
3351  AAACCCATGT ATGAACACTC ACATGTTTGG GAAGGGGGAA GGGCACATGT
      TTTGGGTACA TACTTGTGAG TGTACAAACC CTTCCCCCTT CCCGTGTACA
3401  AAATGAGGAC TCTTCCTCAT TCTATGGGGC ACTCTGGCCC TGCCCCTCTC
      TTTACTCCTG AGAAGGAGTA AGATACCCCG TGAGACCGGG ACGGGGAGAG
3451  AGCTACTCAT CCATCCAACA CACCTTTCTA AGTACCTCTC TCTGCCTACA
      TCGATGAGTA GGTAGGTTGT GTGGAAAGAT TCATGGAGAG AGACGGATGT
3501  CTCTGAAGGG GTTCAGGAGT AACTAACACA GCATCCCTTC CCTCAAATGA
      GAGACTTCCC CAAGTCCTCA TTGATTGTGT CGTAGGGAAG GGAGTTTACT
3551  CTGACAATCC CTTTGTCCTG CTTTGTTTTT CTTTCCAGTC AGTACTGGGA
      GACTGTTAGG GAAACAGGAC GAAACAAAAA GAAAGGTCAG TCATGACCCT
3601  AAGTGGGGAA GGACAGTCAT GGAGAAACTA CATAAGGAAG CACCTTGCCC
      TTCACCCCTT CCTGTCAGTA CCTCTTTGAT GTATTCCTTC GTGGAACGGG
3651  TTCTGCCTCT TGAGAATGTT GATGAGTATC AAATCTTTCA AACTTTGGAG
      AAGACGGAGA ACTCTTACAA CTACTCATAG TTTAGAAAGT TTGAAACCTC
3701  GTTTGAGTAG GGGTGAGACT CAGTAATGTC CCTTCCAATG ACATGAACTT
      CAAACTCATC CCCACTCTGA GTCATTACAG GGAAGGTTAC TGTACTTGAA
3751  GCTCACTCAT CCCTGGGGGC CAAATTGAAC AATCAAAGGC AGGCATAATC
      CGAGTGAGTA GGGACCCCCG GTTTAACTTG TTAGTTTCCG TCCGTATTAG
                                                           SacII
                                                           ~
              EcoRI      NotI      NheI            BamHI
             ~~~~~~~  ~~~~~~~~~  ~~~~~~~         ~~~~~~
3801  CAGTTATGAA TTCTTGCGGC CGCTTGCTAG CTTCACGTGT TGGATCCAAC
      GTCAATACTT AAGAACGCCG GCGAACGATC GAAGTGCACA ACCTAGGTTG
      SacII   ApaI
      ~~~~~  ~~~~~~~
3851  CGCGGAAGGG CCCTATTCTA TAGTGTCACC TAAATGCTAG AGCTCGCTGA
      GCGCCTTCCC GGGATAAGAT ATCACAGTGG ATTTACGATC TCGAGCGACT
3901  TCAGCCTCGA CTGTGCCTTC TAGTTGCCAG CCATCTGTTG TTTGCCCCTC
      AGTCGGAGCT GACACGGAAG ATCAACGGTC GGTAGACAAC AAACGGGGAG
3951  CCCCGTGCCT TCCTTGACCC TGGAAGGTGC CACTCCCACT GTCCTTTCCT
      GGGGCACGGA AGGAACTGGG ACCTTCCACG GTGAGGGTGA CAGGAAAGGA
4001  AATAAAATGA GGAAATTGCA TCGCATTGTC TGAGTAGGTG TCATTCTATT
      TTATTTTACT CCTTTAACGT AGCGTAACAG ACTCATCCAC AGTAAGATAA
4051  CTGGGGGGTG GGGTGGGGCA GGACAGCAAG GGGGAGGATT GGGAAGACAA
      GACCCCCCAC CCCACCCCGT CCTGTCGTTC CCCCTCCTAA CCCTTCTGTT
4101  TAGCAGGCAT GCTGGGGATG CGGTGGGCTC TATGGCTTCT GAGGCGGAAA
      ATCGTCCGTA CGACCCCTAC GCCACCCGAG ATACCGAAGA CTCCGCCTTT
4151  GAACCAGCTG GGGCTCTAGG GGGTATCCCC ACGCGCCCTG TAGCGGCGCA
      CTTGGTCGAC CCCGAGATCC CCCATAGGGG TGCGCGGGAC ATCGCCGCGT
4201  TTAAGCGCGG CGGGTGTGGT GGTTACGCGC AGCGTGACCG CTACACTTGC
      AATTCGCGCC GCCCACACCA CCAATGCGCG TCGCACTGGC GATGTGAACG
4251  CAGCGCCCTA GCGCCCGCTC CTTTCGCTTT CTTCCCTTCC TTTCTCGCCA
      GTCGCGGGAT CGCGGGCGAG GAAAGCGAAA GAAGGGAAGG AAAGAGCGGT
4301  CGTTCGCCGG GCCTCTCAAA AAAGGGAAAA AAAGCATGCA TCTCAATTAG
      GCAAGCGGCC CGGAGAGTTT TTTCCCTTTT TTTCGTACGT AGAGTTAATC
4351  TCAGCAACCA TAGTCCCGCC CCTAACTCCG CCCATCCCGC CCCTAACTCC
      AGTCGTTGGT ATCAGGGCGG GGATTGAGGC GGGTAGGGCG GGGATTGAGG
```

FIG. 4D

```
4401  GCCCAGTTCC GCCCATTCTC CGCCCCATGG CTGACTAATT TTTTTTATTT
      CGGGTCAAGG CGGGTAAGAG GCGGGGTACC GACTGATTAA AAAAAATAAA
4451  ATGCAGAGGC CGAGGCCGCC TCGGCCTCTG AGCTATTCCA GAAGTAGTGA
      TACGTCTCCG GCTCCGGCGG AGCCGGAGAC TCGATAAGGT CTTCATCACT
4501  GGAGGCTTTT TTGGAGGCCT AGGCTTTTGC AAAAAGCTTG GACAGCTCAG
      CCTCCGAAAA AACCTCCGGA TCCGAAAACG TTTTTCGAAC CTGTCGAGTC
4551  GGCTGCGATT TCGCGCCAAA CTTGACGGCA ATCCTAGCGT GAAGGCTGGT
      CCGACGCTAA AGCGCGGTTT GAACTGCCGT TAGGATCGCA CTTCCGACCA
4601  AGGATTTTAT CCCCGCTGCC ATCATGGTTC GACCATTGAA CTGCATCGTC
      TCCTAAAATA GGGGCGACGG TAGTACCAAG CTGGTAACTT GACGTAGCAG
4651  GCCGTGTCCC AAAATATGGG GATTGGCAAG AACGGAGACC TACCCTGGCC
      CGGCACAGGG TTTTATACCC CTAACCGTTC TTGCCTCTGG ATGGGACCGG
4701  TCCGCTCAGG AACGAGTTCA AGTACTTCCA AAGAATGACC ACAACCTCTT
      AGGCGAGTCC TTGCTCAAGT TCATGAAGGT TTCTTACTGG TGTTGGAGAA
4751  CAGTGGAAGG TAAACAGAAT CTGGTGATTA TGGGTAGGAA AACCTGGTTC
      GTCACCTTCC ATTTGTCTTA GACCACTAAT ACCCATCCTT TTGGACCAAG
4801  TCCATTCCTG AGAAGAATCG ACCTTTAAAG GACAGAATTA ATATAGTTCT
      AGGTAAGGAC TCTTCTTAGC TGGAAATTTC CTGTCTTAAT TATATCAAGA
4851  CAGTAGAGAA CTCAAAGAAC CACCACGAGG AGCTCATTTT CTTGCCAAAA
      GTCATCTCTT GAGTTTCTTG GTGGTGCTCC TCGAGTAAAA GAACGGTTTT
4901  GTTTGGATGA TGCCTTAAGA CTTATTGAAC AACCGGAATT GGCAAGTAAA
      CAAACCTACT ACGGAATTCT GAATAACTTG TTGGCCTTAA CCGTTCATTT
4951  GTAGACATGG TTTGGATAGT CGGAGGCAGT TCTGTTTACC AGGAAGCCAT
      CATCTGTACC AAACCTATCA GCCTCCGTCA AGACAAATGG TCCTTCGGTA
5001  GAATCAACCA GGCCACCTTA GACTCTTTGT GACAAGGATC ATGCAGGAAT
      CTTAGTTGGT CCGGTGGAAT CTGAGAAACA CTGTTCCTAG TACGTCCTTA
5051  TTGAAAGTGA CACGTTTTTC CCAGAAATTG ATTTGGGGAA ATATAAACTT
      AACTTTCACT GTGCAAAAAG GGTCTTTAAC TAAACCCCTT TATATTTGAA
5101  CTCCCAGAAT ACCCAGGCGT CCTCTCTGAG GTCCAGGAGG AAAAAGGCAT
      GAGGGTCTTA TGGGTCCGCA GGAGAGACTC CAGGTCCTCC TTTTTCCGTA
5151  CAAGTATAAG TTTGAAGTCT ACGAGAAGAA AGACTAACAG GAAGATGCTT
      GTTCATATTC AAACTTCAGA TGCTCTTCTT TCTGATTGTC CTTCTACGAA
5201  TCAAGTTCTC TGCTCCCCTC CTAAAGCTAT GCATTTTTAT AAGACCATGG
      AGTTCAAGAG ACGAGGGGAG GATTTCGATA CGTAAAAATA TTCTGGTACC
5251  GACTTTTGCT GGCTTTAGAT CTCTTTGTGA AGGAACCTTA CTTCTGTGGT
      CTGAAAACGA CCGAAATCTA GAGAAACACT TCCTTGGAAT GAAGACACCA
5301  GTGACATAAT TGGACAAACT ACCTACAGAG ATTTAAAGCT CTAAGGTAAA
      CACTGTATTA ACCTGTTTGA TGGATGTCTC TAAATTTCGA GATTCCATTT
5351  TATAAAATTT TTAAGTGTAT AATGTGTTAA ACTACTGATT CTAATTGTTT
      ATATTTTAAA AATTCACATA TTACACAATT TGATGACTAA GATTAACAAA
5401  GTGTATTTTA GATTCCAACC TATGGAACTG ATGAATGGGA GCAGTGGTGG
      CACATAAAAT CTAAGGTTGG ATACCTTGAC TACTTACCCT CGTCACCACC
5451  AATGCCTTTA ATGAGGAAAA CCTGTTTTGC TCAGAAGAAA TGCCATCTAG
      TTACGGAAAT TACTCCTTTT GGACAAAACG AGTCTTCTTT ACGGTAGATC
5501  TGATGATGAG GCTACTGCTG ACTCTCAACA TTCTACTCCT CCAAAAAAGA
      ACTACTACTC CGATGACGAC TGAGAGTTGT AAGATGAGGA GGTTTTTTCT
5551  AGAGAAAGGT AGAAGACCCC AAGGACTTTC CTTCAGAATT GCTAAGTTTT
      TCTCTTTCCA TCTTCTGGGG TTCCTGAAAG GAAGTCTTAA CGATTCAAAA
5601  TTGAGTCATG CTGTGTTTAG TAATAGAACT CTTGCTTGCT TTGCTATTTA
      AACTCAGTAC GACACAAATC ATTATCTTGA GAACGAACGA AACGATAAAT
5651  CACCACAAAG GAAAAAGCTG CACTGCTATA CAAGAAAATT ATGGAAAAAT
      GTGGTGTTTC CTTTTTCGAC GTGACGATAT GTTCTTTTAA TACCTTTTTA
5701  ATTCTGTAAC CTTTATAAGT AGGCATAACA GTTATAATCA TAACATACTG
      TAAGACATTG GAAATATTCA TCCGTATTGT CAATATTAGT ATTGTATGAC
5751  TTTTTTCTTA CTCCACACAG GCATAGAGTG TCTGCTATTA ATAACTATGC
      AAAAAAGAAT GAGGTGTGTC CGTATCTCAC AGACGATAAT TATTGATACG
```

FIG. 4E

```
5801  TCAAAAATTG TGTACCTTTA GCTTTTTAAT TTGTAAAGGG GTTAATAAGG
      AGTTTTTAAC ACATGGAAAT CGAAAAATTA AACATTTCCC CAATTATTCC
5851  AATATTTGAT GTATAGTGCC TTGACTAGAG ATCATAATCA GCCATACCAC
      TTATAAACTA CATATCACGG AACTGATCTC TAGTATTAGT CGGTATGGTG
5901  ATTTGTAGAG GTTTTACTTG CTTTAAAAAA CCTCCCACAC CTCCCCCTGA
      TAAACATCTC CAAAATGAAC GAAATTTTTT GGAGGGTGTG GAGGGGGACT
5951  ACCTGAAACA TAAAATGAAT GCAATTGTTG TTGTTAACTT GTTTATTGCA
      TGGACTTTGT ATTTTACTTA CGTTAACAAC AACAATTGAA CAAATAACGT
6001  GCTTATAATG GTTACAAATA AAGCAATAGC ATCACAAATT TCACAAATAA
      CGAATATTAC CAATGTTTAT TTCGTTATCG TAGTGTTTAA AGTGTTTATT
6051  AGCATTTTTT TCACTGCATT CTAGTTGTGG TTTGTCCAAA CTCATCAATG
      TCGTAAAAAA AGTGACGTAA GATCAACACC AAACAGGTTT GAGTAGTTAC
6101  TATCTTATCA TGTCTGGATC GGCTGGATGA TCCTCCAGCG CGGGGATCTC
      ATAGAATAGT ACAGACCTAG CCGACCTACT AGGAGGTCGC GCCCCTAGAG
6151  ATGCTGGAGT TCTTCGCCCA CCCCAACTTG TTTATTGCAG CTTATAATGG
      TACGACCTCA AGAAGCGGGT GGGGTTGAAC AAATAACGTC GAATATTACC
6201  TTACAAATAA AGCAATAGCA TCACAAATTT CACAAATAAA GCATTTTTTT
      AATGTTTATT TCGTTATCGT AGTGTTTAAA GTGTTTATTT CGTAAAAAAA
6251  CACTGCATTC TAGTTGTGGT TTGTCCAAAC TCATCAATGT ATCTTATCAT
      GTGACGTAAG ATCAACACCA AACAGGTTTG AGTAGTTACA TAGAATAGTA
6301  GTCTGTATAC CGTCGACCTC TAGCTAGAGC TTGGCGTAAT CATGGTCATA
      CAGACATATG GCAGCTGGAG ATCGATCTCG AACCGCATTA GTACCAGTAT
6351  GCTGTTTCCT GTGTGAAATT GTTATCCGCT CACAATTCCA CACAACATAC
      CGACAAAGGA CACACTTTAA CAATAGGCGA GTGTTAAGGT GTGTTGTATG
6401  GAGCCGGAAG CATAAAGTGT AAAGCCTGGG GTGCCTAATG AGTGAGCTAA
      CTCGGCCTTC GTATTTCACA TTTCGGACCC CACGGATTAC TCACTCGATT
6451  CTCACATTAA TTGCGTTGCG CTCACTGCCC GCTTTCCAGT CGGGAAACCT
      GAGTGTAATT AACGCAACGC GAGTGACGGG CGAAAGGTCA GCCCTTTGGA
6501  GTCGTGCCAG CTGCATTAAT GAATCGGCCA ACGCGCGGGG AGAGGCGGTT
      CAGCACGGTC GACGTAATTA CTTAGCCGGT TGCGCGCCCC TCTCCGCCAA
6551  TGCGTATTGG GCGCTCTTCC GCTTCCTCGC TCACTGACTC GCTGCGCTCG
      ACGCATAACC CGCGAGAAGG CGAAGGAGCG AGTGACTGAG CGACGCGAGC
6601  GTCGTTCGGC TGCGGCGAGC GGTATCAGCT CACTCAAAGG CGGTAATACG
      CAGCAAGCCG ACGCCGCTCG CCATAGTCGA GTGAGTTTCC GCCATTATGC
6651  GTTATCCACA GAATCAGGGG ATAACGCAGG AAAGAACATG TGAGCAAAAG
      CAATAGGTGT CTTAGTCCCC TATTGCGTCC TTTCTTGTAC ACTCGTTTTC
6701  GCCAGCAAAA GGCCAGGAAC CGTAAAAAGG CCGCGTTGCT GGCGTTTTTC
      CGGTCGTTTT CCGGTCCTTG GCATTTTTCC GGCGCAACGA CCGCAAAAAG
6751  CATAGGCTCC GCCCCCCTGA CGAGCATCAC AAAAATCGAC GCTCAAGTCA
      GTATCCGAGG CGGGGGGACT GCTCGTAGTG TTTTTAGCTG CGAGTTCAGT
6801  GAGGTGGCGA AACCCGACAG GACTATAAAG ATACCAGGCG TTTCCCCCTG
      CTCCACCGCT TTGGGCTGTC CTGATATTTC TATGGTCCGC AAAGGGGGAC
6851  GAAGCTCCCT CGTGCGCTCT CCTGTTCCGA CCCTGCCGCT TACCGGATAC
      CTTCGAGGGA GCACGCGAGA GGACAAGGCT GGGACGGCGA ATGGCCTATG
6901  CTGTCCGCCT TTCTCCCTTC GGGAAGCGTG GCGCTTTCTC AATGCTCACG
      GACAGGCGGA AAGAGGGAAG CCCTTCGCAC CGCGAAAGAG TTACGAGTGC
6951  CTGTAGGTAT CTCAGTTCGG TGTAGGTCGT TCGCTCCAAG CTGGGCTGTG
      GACATCCATA GAGTCAAGCC ACATCCAGCA AGCGAGGTTC GACCCGACAC
7001  TGCACGAACC CCCCGTTCAG CCCGACCGCT GCGCCTTATC CGGTAACTAT
      ACGTGCTTGG GGGGCAAGTC GGGCTGGCGA CGCGGAATAG GCCATTGATA
7051  CGTCTTGAGT CCAACCCGGT AAGACACGAC TTATCGCCAC TGGCAGCAGC
      GCAGAACTCA GGTTGGGCCA TTCTGTGCTG AATAGCGGTG ACCGTCGTCG
7101  CACTGGTAAC AGGATTAGCA GAGCGAGGTA TGTAGGCGGT GCTACAGAGT
      GTGACCATTG TCCTAATCGT CTCGCTCCAT ACATCCGCCA CGATGTCTCA
7151  TCTTGAAGTG GTGGCCTAAC TACGGCTACA CTAGAAGGAC AGTATTTGGT
      AGAACTTCAC CACCGGATTG ATGCCGATGT GATCTTCCTG TCATAAACCA
```

FIG. 4F

```
7201  ATCTGCGCTC TGCTGAAGCC AGTTACCTTC GGAAAAAGAG TTGGTAGCTC
      TAGACGCGAG ACGACTTCGG TCAATGGAAG CCTTTTTCTC AACCATCGAG
7251  TTGATCCGGC AAACAAACCA CCGCTGGTAG CGGTGGTTTT TTTGTTTGCA
      AACTAGGCCG TTTGTTTGGT GGCGACCATC GCCACCAAAA AAACAAACGT
7301  AGCAGCAGAT TACGCGCAGA AAAAAAGGAT CTCAAGAAGA TCCTTTGATC
      TCGTCGTCTA ATGCGCGTCT TTTTTTCCTA GAGTTCTTCT AGGAAACTAG
7351  TTTTCTACGG GGTCTGACGC TCAGTGGAAC GAAAACTCAC GTTAAGGGAT
      AAAAGATGCC CCAGACTGCG AGTCACCTTG CTTTTGAGTG CAATTCCCTA
7401  TTTGGTCATG AGATTATCAA AAAGGATCTT CACCTAGATC CTTTTAAATT
      AAACCAGTAC TCTAATAGTT TTTCCTAGAA GTGGATCTAG GAAAATTTAA
7451  AAAAATGAAG TTTTAAATCA ATCTAAAGTA TATATGAGTA AACTTGGTCT
      TTTTTACTTC AAAATTTAGT TAGATTTCAT ATATACTCAT TTGAACCAGA
7501  GACAGTTACC AATGCTTAAT CAGTGAGGCA CCTATCTCAG CGATCTGTCT
      CTGTCAATGG TTACGAATTA GTCACTCCGT GGATAGAGTC GCTAGACAGA
7551  ATTTCGTTCA TCCATAGTTG CCTGACTCCC CGTCGTGTAG ATAACTACGA
      TAAAGCAAGT AGGTATCAAC GGACTGAGGG GCAGCACATC TATTGATGCT
7601  TACGGGAGGG CTTACCATCT GGCCCCAGTG CTGCAATGAT ACCGCGAGAC
      ATGCCCTCCC GAATGGTAGA CCGGGGTCAC GACGTTACTA TGGCGCTCTG
7651  CCACGCTCAC CGGCTCCAGA TTTATCAGCA ATAAACCAGC CAGCCGGAAG
      GGTGCGAGTG GCCGAGGTCT AAATAGTCGT TATTTGGTCG GTCGGCCTTC
7701  GGCCGAGCGC AGAAGTGGTC CTGCAACTTT ATCCGCCTCC ATCCAGTCTA
      CCGGCTCGCG TCTTCACCAG GACGTTGAAA TAGGCGGAGG TAGGTCAGAT
7751  TTAATTGTTG CCGGGAAGCT AGAGTAAGTA GTTCGCCAGT TAATAGTTTG
      AATTAACAAC GGCCCTTCGA TCTCATTCAT CAAGCGGTCA ATTATCAAAC
7801  CGCAACGTTG TTGCCATTGC TACAGGCATC GTGGTGTCAC GCTCGTCGTT
      GCGTTGCAAC AACGGTAACG ATGTCCGTAG CACCACAGTG CGAGCAGCAA
7851  TGGTATGGCT TCATTCAGCT CCGGTTCCCA ACGATCAAGG CGAGTTACAT
      ACCATACCGA AGTAAGTCGA GGCCAAGGGT TGCTAGTTCC GCTCAATGTA
7901  GATCCCCCAT GTTGTGCAAA AAAGCGGTTA GCTCCTTCGG TCCTCCGATC
      CTAGGGGGTA CAACACGTTT TTTCGCCAAT CGAGGAAGCC AGGAGGCTAG
7951  GTTGTCAGAA GTAAGTTGGC CGCAGTGTTA TCACTCATGG TTATGGCAGC
      CAACAGTCTT CATTCAACCG GCGTCACAAT AGTGAGTACC AATACCGTCG
8001  ACTGCATAAT TCTCTTACTG TCATGCCATC CGTAAGATGC TTTTCTGTGA
      TGACGTATTA AGAGAATGAC AGTACGGTAG GCATTCTACG AAAAGACACT
8051  CTGGTGAGTA CTCAACCAAG TCATTCTGAG AATAGTGTAT GCGGCGACCG
      GACCACTCAT GAGTTGGTTC AGTAAGACTC TTATCACATA CGCCGCTGGC
8101  AGTTGCTCTT GCCCGGCGTC AATACGGGAT AATACCGCGC CACATAGCAG
      TCAACGAGAA CGGGCCGCAG TTATGCCCTA TTATGGCGCG GTGTATCGTC
8151  AACTTTAAAA GTGCTCATCA TTGGAAAACG TTCTTCGGGG CGAAAACTCT
      TTGAAATTTT CACGAGTAGT AACCTTTTGC AAGAAGCCCC GCTTTTGAGA
8201  CAAGGATCTT ACCGCTGTTG AGATCCAGTT CGATGTAACC CACTCGTGCA
      GTTCCTAGAA TGGCGACAAC TCTAGGTCAA GCTACATTGG GTGAGCACGT
8251  CCCAACTGAT CTTCAGCATC TTTTACTTTC ACCAGCGTTT CTGGGTGAGC
      GGGTTGACTA GAAGTCGTAG AAAATGAAAG TGGTCGCAAA GACCCACTCG
8301  AAAAACAGGA AGGCAAAATG CCGCAAAAAA GGGAATAAGG GCGACACGGA
      TTTTTGTCCT TCCGTTTTAC GGCGTTTTTT CCCTTATTCC CGCTGTGCCT
8351  AATGTTGAAT ACTCATACTC TTCCTTTTTC AATATTATTG AAGCATTTAT
      TTACAACTTA TGAGTATGAG AAGGAAAAAG TTATAATAAC TTCGTAAATA
8401  CAGGGTTATT GTCTCATGAG CGGATACATA TTTGAATGTA TTTAGAAAAA
      GTCCCAATAA CAGAGTACTC GCCTATGTAT AAACTTACAT AAATCTTTTT
8451  TAAACAAATA GGGGTTCCGC GCACATTTCC CCGAAAAGTG CCACCTGACG
      ATTTGTTTAT CCCCAAGGCG CGTGTAAAGG GGCTTTTCAC GGTGGACTGC
                            NheI                AscI
                            ~~~~~~~             ~~~~~~~~~
8501  TCGACGGATC GGGAGATCTG CTAGCCCGGG TGACCTGAGG CGCGCCGGCT
      AGCTGCCTAG CCCTCTAGAC GATCGGGCCC ACTGGACTCC GCGCGGCCGA
```

FIG. 4G

```
8551    TCGAATAGCC AGAGTAACCT TTTTTTTTAA TTTTATTTTA TTTTATTTTT
        AGCTTATCGG TCTCATTGGA AAAAAAAATT AAAATAAAAT AAAATAAAAA
8601    GAGATGGAGT TTGGCGCCGA TCTCCCGATC CCCTATGGTC GACTCTCAGT
        CTCTACCTCA AACCGCGGCT AGAGGGCTAG GGGATACCAG CTGAGAGTCA
8651    ACAATCTGCT CTGATGCCGC ATAGTTAAGC CAGTATCTGC TCCCTGCTTG
        TGTTAGACGA GACTACGGCG TATCAATTCG GTCATAGACG AGGGACGAAC
8701    TGTGTTGGAG GTCGCTGAGT AGTGCGCGAG CAAAATTTAA GCTACAACAA
        ACACAACCTC CAGCGACTCA TCACGCGCTC GTTTTAAATT CGATGTTGTT
8751    GGCAAGGCTT GACCGACAAT TGCATGAAGA ATCTGCTTAG GGTTAGGCGT
        CCGTTCCGAA CTGGCTGTTA ACGTACTTCT TAGACGAATC CCAATCCGCA
8801    TTTGCGCTGC TTCGCGATGT ACGGGCCAGA TATACGCGTT GACATTGATT
        AAACGCGACG AAGCGCTACA TGCCCGGTCT ATATGCGCAA CTGTAACTAA
8851    ATTGACTAGT TATTAATAGT AATC
        TAACTGATCA ATAATTATCA TTAG
```

FIG. 4H

HUMANIZED ANTIBODIES AGAINST HUMAN 4-1BB

This invention claims the benefit of U.S. Provisional Application No. 60/399,646 filed Jul. 30, 2002, whose contents are hereby incorporated by reference in its entirety.

BACKGROUND OF THE INVENTION

The invention is directed to humanized antibodies and, more specifically, to humanized antibodies to human 4-1BB.

An extensive body of evidence has unequivocally demonstrated that some degree of immune response against cancer exists in humans and animals. In cancer patients, cellular components of the immune system are able to recognize antigens expressed by tumor cells, such as differentiation or oncofetal antigens, or mutated gene products (S. Rosenberg, Nature, 411:380 (2001)). A number of clinical studies have shown that tumor-infiltrating lymphocytes have favorable prognostic significance (E. Halapi, Med. Oncol., 15:203 (1998); J. Resser et al., Curr. Opin. Oncol., 10:226 (1998); D. Elder, Acta Oncol., 38:535 (1999); L. Zhang et al., New Engl. J. Med., 348:203–213(2003)). Furthermore, clinical results with immunomodulators (bacterial products or biological response modifiers such as cytokines) led to tumor regression in a number of patients (S. A. Rosenberg, Cancer J. Sci. Am. 6 (S):2 (2000); P. Bassi, Surg. Oncol.11:77 (2002); Fishman M, and S. Antonia, Expert Opin Investig Drugs. 12:593 (2003). Despite these responses, immunity against cancer frequently fails to effectively eliminate tumor cells. Among the known causes of immune failure against cancer is the lack of co-stimulatory molecules on tumors, which results in the inability of the tumor cells to effectively stimulate T cells. Recent advances in our understanding of the requirements for tumor antigen recognition and immune effector function indicate that a potential successful strategy to enhance an anti-tumor immune response is providing co-stimulation through an auxiliary molecule.

The current model for T cell activation postulates that for an induction of full activation, naive T cells require two signals: a signal provided through the binding of processed antigens presented to the T-cell receptor by major histocompatibility complex (MHC) class I molecules (signal 1); and an additional signal provided by the interaction of co-stimulatory molecules on the surface of T-cells and their ligands on antigen presenting cells (signal 2) (D. Lenschow et al., Annu. Rev. Immunol., 14:233–258, (1996); C. Chambers et al., Curr. Opin. Immunol., 9:396–404 (1997)). Recognition of an antigen by a naive T cell is insufficient in itself to trigger T-cell activation. Without the second co-stimulatory signal, T cells may be eliminated either by promoting its death or by inducing anergy (A. Abbas et al., Cellular and Molecular Immunology, 3rd ed., 139–170, (1997)).

4-1BB, also referred to as CD137, is a member of the tumor necrosis factor receptor (TNFR) gene family which includes proteins involved in regulation of cell proliferation, differentiation, and programmed cell death (A. Ashkenazi, Nature, 2:420–430, (2002)). 4-1BB is expressed predominantly on activated T cells, including both CD4+ and CD8+ cells, NK cells, and NK T cells (B. Kwon et al., Mol. Cell, 10:119–126, (2000); J. Hurtado et al, J. Immunol. 155:3360–3365, (1995); L. Melero et al., Cell. Immunol. 190:167–172, (1998)). In addition, 4-1BB has been detected on dendritic cells (T. Futagawa et al., Int. Immunol. 14:275–286, (2002); R. Wilcox et al., J. Immunol.

168:4262–4267, (2002); M. Lindstedt et al., Scand. J. Immunol. 57:305–310, (2003)), macrophages, activated eosinophils, and intra-epithelial lymphocytes (K. Pollok et al., J. Immunol. 150:771–781 (1993); D. Vinay et al., Semin. Immunol. 10:481–489, (1998)). Naive, resting T-cells do not express the receptor, which is up-regulated upon activation. Signaling through 4-1BB was demonstrated to induce T-cell proliferation, induction of interferon-gamma (IFN-$\gamma$) synthesis, and inhibition of activated cell death in murine and human T-cells (Y. Kim et al., Eur. J. Immunol. 28:881–890, (1998); J. Hurtado et al., J. Immunol., 158:2600–2609, (1997); C. Takahashi et al., J. Immunol., 162:5037, (1999)). The natural ligand for 4-1BB, 4-1BB ligand (4-1BBL), is a member of the TNF superfamily and is detected mainly on activated antigen-presenting cells, such as B cells, macrophages, and dendritic cells (M. Alderson et al., Eur. J. Immunol., 24:2219–2227 (1994); K. Pollok, et al., Eur. J. Immunol. 24:367–374 (1994)) but also in murine B-cell lymphomas, activated T-cells, and human carcinoma lines of epithelial origin (M. DeBenedette et al., J. Immunol. 158:551–559 (1997); H. Salih et al., J. Immunol. 2903–2910 (2000)).

In vivo efficacy studies in mice have demonstrated that treatment with anti-4-1BB antibodies led to tumor regressions in multiple tumor models, indicating the potential use of this therapy for the treatment of cancer. Of note, anti-murine 4-1BB antibodies were shown to induce an immune response against tumors that were poorly or non-immunogenic (I. Melero et al., Nat Med. 3:682–685, (1997); R. Wilcox et al., J. Clin. Invest. 109:651–659, (2002)). Anti-murine 4-1BB antibodies that showed anti-tumor activity were shown to enhance IFN-gamma synthesis in vitro. A number of reports have unequivocally demonstrated that in vivo induction of IFN-gamma by treatment with anti-4-1BB antibodies is critical for the production of an effective anti-tumor immune response (R. Wilcox et al., Cancer Res. 62:4413 (2002); R. Miller et al., J. Immunol. 169:1792 (2002) and studies reported here). Neutralization of IFN-gamma activities significantly reduced the antitumor effects observed with anti-4-1BB antibodies in several tumor models, revealing a correlation between in vitro functional effects, i.e., induction of IFN-gamma, and in vivo anti-tumor efficacy. There is ample in vitro evidence that binding of human 4-BB to its natural ligand or anti-human 4-1BB antibodies produce similar functional effects to that observed with anti-murine 4-1BB antibodies (Y. Kim et al., Eur. J. Immunol. 28:881 (1998); Y. Wen et al., J. Immunol. 168:4897 (2002)). However, most of the anti-human 4-1BB antibodies reported have been raised in rodents which made them unsuitable for human treatment. One report demonstrated that administration of a humanized anti-human 4-1BB antibody in vivo induced suppression of T-cell dependent immunity in nonhuman primates, an effect also observed with anti-murine 4-1BB antibodies (H. Hong et al., J Immunother. 23:613–621 (2000)).

Consequently, based on the roles of 4-1BB in modulating the immune response and the demonstration of efficacy in murine tumor models, it would be desirable to produce anti-human 4-1BB antibodies with agonistic activities that could be used for the treatment or prevention of human diseases like cancer.

BRIEF SUMMARY OF THE INVENTION

The present invention provides humanized antibodies that bind to human 4-1BB (H4-1BB) and that allow binding of H4-1BB to a human 4-1BB ligand (H4-1BBL). Thus, the invention is directed to antibodies that bind to H4-1BB and that do not block the binding of H4-1BB to its H4-1BBL, thereby permitting the binding of both an antibody of the invention and H4-1BBL to H4-1BB. The antibodies of the invention bind to H4-1BB with high affinity and/or induce interferon-gamma synthesis (IFN-γ), i.e., have agonist activity, but do not block the interaction between H4-1BB and H4-1BBL. These antibodies can be used as immunoenhancers of an anti-tumor immune response.

In one aspect, the antibody comprises a light chain and a heavy chain, wherein: said heavy chain includes a CDR1 (complementary determining region 1) comprising amino acids 50 to 54 of SEQ ID NO:5, a CDR2 (complementary determining region 2) comprising amino acids 69 to 85 of SEQ ID NO:5, and a CDR3 (complementary determining region 3) comprising amino acids 118 to 122 of SEQ ID NO:5; and said light chain includes a CDR1 (complementary determining region 1) comprising amino acids 44 to 60 of SEQ ID NO:8, a CDR2 (complementary determining region 2) comprising amino acids 76 to 82 of SEQ ID NO:8, and a CDR3 (complementary determining region 3) comprising amino acids 115 to 123 of SEQ ID NO:8.

In another aspect, the humanized antibody is an IgG4 antibody.

In yet another aspect, the antibody comprises the amino acid sequences of SEQ ID NO:5 and SEQ ID NO:8.

In another aspect, the humanized antibody is hu39E3.G4. This humanized antibody presents high affinity for H4-1BB, i.e., specifically binds H4-1BB, and effectively induces IFN-γ synthesis, but does not affect the binding of H4-1BB to its corresponding ligand, H4-1BBL, and does not fix complement, i.e., is of the IgG4 isotype. Thus, hu39E3.G4 is a non-blocking, agonist anti-4-1BB antibody that is capable of inducing T cell proliferation and cytokine production.

The invention also provides pharmaceutical compositions comprising an antibody of the invention, or an antigen-binding portion thereof, and a pharmaceutically acceptable carrier. The pharmaceutical composition can be administered alone or in combination with an agent, e.g., an agent for treating cancer such as a chemotherapeutic agent or a vaccine.

The antibodies of the invention have wide therapeutic applications as immunomodulators of diseases such as cancer, autoimmune diseases, inflammatory diseases, and infectious diseases. Because of the expression of H4-1BB seen on effector $CD8^+/CD4^+$ T cells and NK cells, the potential oncology applications of anti-H4-1BB antibodies are evident. The invention further provides methods for treating cancer in a subject comprising administering a therapeutically effective amount of the antibody of the invention to said subject. In one aspect, this method further comprises administering a vaccine. Suitable vaccines include, for example, a tumor cell vaccine, a GM-CSF-modified tumor cell vaccine, or an antigen-loaded dendritic cell vaccine. The cancer can be, for example, prostate cancer, melanoma, or epithelial cancer.

The invention also provides isolated polynucleotides comprising a nucleotide sequence selected from the group consisting of: (a) nucleotides 693 to 2072 of SEQ ID NO:3; and (b) nucleotides 633 to 1034 and 1409 to 1726 of SEQ ID NO:6. The invention further provides isolated polynucleotides that comprise the nucleotide sequence of SEQ ID NO:3 or SEQ ID NO:6.

The invention also provides isolated polypeptides comprising an amino acid sequence selected from the group consisting of SEQ ID NO:5 and SEQ ID NO:8.

The invention further provides a humanized immunoglobulin having binding specificity for H4-1BB, said immunoglobulin comprising an antigen binding region of nonhuman origin. In one aspect, the immunoglobulin further comprises a portion of human origin. In another aspect, the immunoglobulin is a Fab fragment (antigen binding fragment) of an antibody of the invention.

The invention also provides a hybridoma cell line that produces an H4-1BB antibody. In one aspect, the hybridoma cell line is rat hybridoma 39E3 deposited with the ATCC and having Accession Number ATCC-PTA-5326. The invention further provides hybridoma cell lines wherein the hybridoma produces an antibody that specifically binds to H4-1BB or binding fragment thereof.

All deposits referred to herein were made with the American Type Culture Collection (ATCC), Manassas, Va. 20110 USA and will be maintained under the terms of the Budapest Treaty on the International Recognition of the Deposit of Micro-Organisms for purposes of Patent Procedure. These deposits are provided merely as convenience to those of skill in the art and are not an admission that such a deposit is required under 35 U.S.C. § 112. The sequences of the polynucleotides contained in the deposited materials, as well as the amino acid sequence of the polypeptides encoded thereby, are incorporated herein by reference and are controlling in the event of any conflict with any description of sequences herein. A license may be required to make, use, or sell the deposited materials, and no such license is hereby granted.

BRIEF DESCRIPTION OF THE DRAWINGS

FIG. 1 shows a plasmid map of pD17-H39E3-2.h4a.

FIGS. 2A–2G show the nucleotide sequence of the plasmid pD17-H39E3-2.h4a (coding strand (SEQ ID NO:3) and complementary strand (SEQ ID NO:4)) and the heavy chain amino acid sequence (SEQ ID NO:5) encoded by nucleotides 693 to 2071 of the coding strand (SEQ ID NO:3). As shown in FIGS. 2A–2G, the heavy chain amino acid sequence includes a CDR1 comprising amino acids 50 to 54 of SEQ ID NO:5, a CDR2 comprising amino acids 69 to 85 of SEQ ID NO:5, and a CDR3 comprising amino acids 118 to 122 of SEQ ID NO:5.

FIGS. 4A–4H show the nucleotide sequence of the plasmid pD16-H39E3.L1 (coding strand (SEQ ID NO:6) and complementary strand (SEQ ID NO:7)) and the light chain amino acid sequence (SEQ ID NO:8) encoded by nucleotides 633 to 1034 and 1409 to 1726 of the coding strand (SEQ ID NO:6). As shown in FIGS. 4A–4H, the light chain amino acid sequence includes a CDR1 comprising amino acids 44 to 60 of SEQ ID NO:8, a CDR2 comprising amino acids 76 to 82 of SEQ ID NO:8, and a CDR3 comprising amino acids 115 to 123 of SEQ ID NO:8.

DETAILED DESCRIPTION OF THE INVENTION

Figure 1:
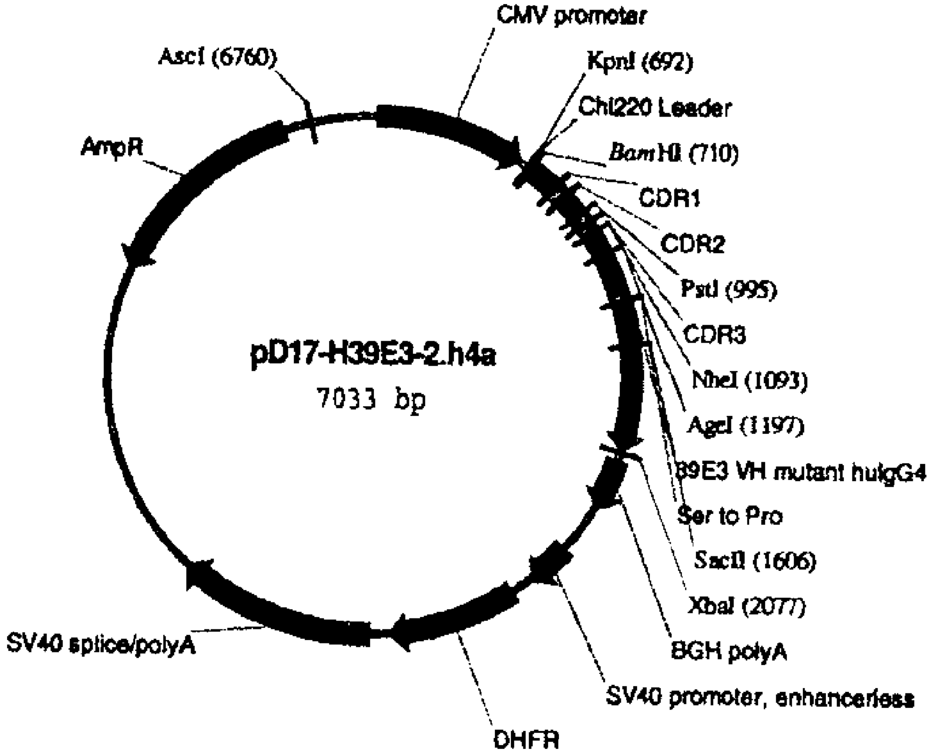

The invention is directed to the preparation and characterization of a humanized immunoglobulin for use in the treatment of cancer, which immunoglobulin is specifically capable of binding to H4-1BB. The humanized antibody, hu39E3.G4, of the present invention, like its parental rat mAb (39E3), presents high affinity for H4-1BB and effectively induces IFN-γ production in co-stimulatory assays, but does not affect the binding of H4-1BB to its corresponding ligand, H4-1BBL and does not fix complement. The antibody comprises two pairs of light chain/heavy chain complexes, at least one chain comprising one or more rat complementary determining regions (CDRs) functionally joined to human framework region segments.

The immunoglobulin, including binding fragments and other derivatives thereof, of the invention may be produced readily by a variety of recombinant DNA techniques, with ultimate expression in transfected cells, preferably immortalized eukaryotic cells, such as myeloma or hybridoma cells. Polynucleotides comprising a first sequence coding for humanized immunoglobulin framework regions and a second sequence set coding for the desired immunoglobulin complementary determining regions can be produced synthetically or by combining appropriate cDNA and genomic DNA segments.

The humanized antibody of the invention may be used alone in substantially pure form, or together with other therapeutic agents such as radiotherapy, hormonal therapy, cytotoxic agents, vaccines, and other immunomodulatory agents, such us cytokines and biological response modifiers. These compounds will be particularly useful in treating cancer or other immune-proliferative disorders. The humanized antibody complexes can be prepared in a pharmaceutically acceptable dosage form, which will vary depending on the mode of administration.

As used herein, "humanized" antibodies comprise antibodies with human framework regions combined with CDRs from a donor mouse or rat immunoglobulin (See, for example, U.S. Pat. No. 5,530,101). Encompassed within the scope of the present invention are humanized antibodies which comprise CDRs derived from the rodent variable chains disclosed herein.

As used herein the term "treating" includes the administration of the compounds or agents of the invention to prevent or delay the onset of symptoms, complications, or biochemical indicia of a disease, alleviating the symptoms or arresting or inhibiting further development of the disease, condition, or disorder (e.g., cancer). Treatment may be prophylactic (to delay the onset of the disease or to prevent the manifestation of clinical or subclinical symptoms thereof) or therapeutic suppression or alleviation of symptoms after the manifestation of the disease.

As used herein the term "specific binding" refers to an antibody binding to a predetermined antigen. When referring to a peptide, the term refers to a peptide molecule which has intermediate or high binding affinity to a target molecule. The phrase "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample.

The term "recombinant humanized antibody" includes all humanized antibodies of the invention that are prepared, expressed, created or isolated by recombinant means, such as antibodies isolate from an animal (e.g. a mouse); antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequence. Such antibodies can, however, be subjected to in vitro mutagenesis (or, when an animal transgenic for human Ig sequences is used, in vivo somatic mutagenesis) and thus the amino acid sequences of the VH (antibody heavy chain variable region) and VL (antibody light chain variable region) of the recombinant antibodies are sequences that, while derived from and related to human germline VH and VL sequences, may not naturally exist within the human antibody germline.

The most straightforward approach to humanizing an antibody consists of grafting the CDRs from the donor mAb onto a human framework (P. Jones et al., Nature 321:522–525 (1986)). However, certain framework residues support CDR structure, and contact antigen grafting rodent CDRs onto human framework templates may diminish the binding activity of the resulting humanized mAb (J. Foote et al., J. Mol. Biol. 224:487–499 (1992)). Because of this, the potential contribution of specific framework residues to antibody structure and affinity can be assessed by structural modeling.

The invention encompasses a humanized antibody with additional conservative amino acid substitutions that have substantially no effect on H4-1BB binding. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine.

Also encompassed within the invention are the disclosed heavy and light chain variable regions and active or functional parts thereof. The immunologically competent or functional form of the protein or part thereof is also referred to herein as a "light/heavy chain variable region or biologically active portion thereof". In the present case, a biologically active portion thereof comprises a portion of said light or heavy chain which, when incorporated into an antibody, still permits the antibody to bind to H4-1BB.

Specifically encompassed within the present invention are nucleic acid sequences encoding the variable heavy chain (SEQ ID NO:3) and the variable light chain (SEQ ID NO:6) of an antibody of the present invention. Also encompassed within the present invention are plasmids comprising the polynucleotides shown in SEQ ID NO:3 and SEQ ID NO:6 and having ATCC Accession Numbers ATCC-PTA-5325 and ATCC-PTA-5324, respectively.

A humanized antibody that binds to H4-1BB and that comprise polypeptides that are substantially homologous to, or that show substantial sequence identity to, the variable light and heavy chain sequences disclosed herein are also contemplated by the present invention. For example, a humanized antibody comprising a light chain region that exhibits at least about 85% sequence identity, more preferably at least about 90% sequence identity, even more preferably at least about 95% sequence identity, and most preferably at least about 98% sequence identity with the light chain region as shown in SEQ ID NO:8 are included within the scope of the present invention. Additionally, a humanized antibody comprising a heavy chain region that exhibits at least about 85% sequence identity, more preferably at least about 90% sequence identity, even more preferably at least about 95% sequence identity, and most preferably at least about 98% sequence identity with the heavy chain region as shown in SEQ ID NO:5 are included within the scope of the present invention.

The DNA segments typically further comprise an expression control DNA sequence operably linked to the humanized antibody coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into an appropriate host, the host is maintained under conditions suitable for high level expression of the nucleotide sequences and, as desired, the collection and purification of the variable light chain, heavy chain, light/heavy chain dimers or intact antibody, binding fragments or other immunoglobulin form may follow. (See, S. Beychok, Cells of Immunoglobulin Synthesis, Academic Press, N.Y. (1979)). Single chain antibodies may also be produced by joining nucleic acid sequences encoding the VL and VH regions disclosed herein with DNA encoding a polypeptide linker.

Prokaryotic hosts, such as *E. coli*, and other microbes, such as yeast, may be used to express an antibody of the present invention. In addition to microorganisms, mammalian tissue cell culture may also be used to express and produce the antibodies of the present invention. Eukaryotic cells may be preferred, because a number of suitable host cell lines capable of secreting intact immunoglobulins have been developed in the art, and include the CHO (chinese hamster ovary) cell lines, various COS (African green monkey fibroblast cell line) cell lines, HeLa cells, myeloma cell lines, and hybridomas. Expression vectors for these cells can include expression control sequences, such as a promoter or enhancer, and necessary processing information sites, such as ribosome binding sites, RNA splice sites, polyadenylation sites, and transcriptional terminator sequences, all known in the art.

The vectors containing the DNA segments of interest (e.g., the heavy and/or light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, e.g., T. Maniatis et al., Molecular Cloning: A Laboratory Manual, Cold Spring Harbor Press (1982)).

Once expressed, the whole antibodies, their dimers, individual light and heavy chains, or other immunoglobulin forms of the present invention, can be purified according to standard procedures in the art, including ammonium sulfate precipitation, affinity columns, column chromatography, gel electrophoresis and the like. Substantially pure immunoglobulins of at least 90 to 95% homogeneity are preferred, and 98 to 99% or more homogeneity are most preferred, for pharmaceutical uses.

The antibodies of the present invention will typically find use in treating antibody mediated and/or T cell mediated disorders. Typical disease states suitable for treatment include cancer, infectious diseases and autoimmune diseases such as multiple sclerosis, rheumatoid arthritis, systemic lupus erythematosus, and myesthenia gravis.

The invention provides pharmaceutical compositions comprising at least one humanized antibody of the present invention formulated with a pharmaceutically acceptable carrier. Some compositions include a combination with other agents used for the treatment of cancer, such as chemotherapeutics, infectious diseases or autoimmune disease as stated above. Alternatively, the pharmaceutical composition can comprise or be co-administered with another agent that can include a second antibody, a co-stimulatory molecule or immunomodulator.

The antibodies and pharmaceutical compositions of the present invention are particularly useful for parenteral administration, i.e., subcutaneously, intramuscularly or intravenously. The pharmaceutical compositions for parenteral administration will commonly comprise a solution of the antibody dissolved in an acceptable carrier, preferably an aqueous carrier. A variety of aqueous carriers can be used, all well known in the art, e.g., water, buffered water, saline, glycine and the like. These solutions are sterile and generally free of particulate matter. These pharmaceutical compositions may be sterilized by conventional well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, human albumin, etc.

The amount of active ingredient which can be combined with a carrier material to produce a single dosage form will generally be that amount of the composition which produces a therapeutic effect. It is especially advantageous to formulate parenteral compositions in dosage unit form for ease of administration and uniformity of dosage. Those skilled in the art would be able to formulate dosage unit forms according to standard known techniques dictated by and directly dependent on the unique characteristics of the active compound and the particular therapeutic effect to be achieved and the limitations inherent in the art of compounds such an active compound for the treatment of sensitivity in individuals.

Effective doses of the compositions of the present invention, for the treatment of cancer, infectious diseases and autoimmune diseases described herein vary depending upon many different factors, including means of administration, target sit, physiological state of the patient, other medications administered and whether the treatment is prophylactic or therapeutic. Notwithstanding these factors, for administration with an antibody of the present invention, the dosage ranges from about 1.0 to 10.0 mg/kg. Antibodies are typically administered on multiple occasions. Intervals between single dosages can be weekly, monthly or bi-monthly depending on the individual needs of the patient. Those skilled in the art would be able using standard pharmacological methodologies to determine the necessary treatment regime depending on the specific disease and severity of the condition to be treated.

The compositions containing antibodies of the present invention can be administered for prophylactic and/or therapeutic treatments. In therapeutic application, compositions are administered to a patient already suffering from a disease, in an amount sufficient to cure or at least partially arrest the disease and its complications. An amount adequate to accomplish this is defined as a "therapeutically effective dose". Amounts effective for this use will depend upon the severity of the disease state and the general state of the patient's own immune system, and can be determined by one skilled in the art.

In prophylactic applications, compositions containing antibodies of the present invention are administered to a patient not already in the disease state to enhance the patient's resistance (enhance an immune response). Such an amount is defined to be a "prophylactically effective dose". In this use, the precise amounts again depend upon the patient's state of health and general level of immunity. A preferred prophylactic use is for the prevention of tumor recurrence.

The following examples are for illustrative purposes only and do not limit the scope of the invention, which is defined only by the claims.

EXAMPLES

I. Immunization and Screening Protocols

A. Immunization

Sprague Dawley rats were immunized with a recombinant fusion protein consisting of the extracellular domain of H4-1BB fused to the constant domains of a human IgG1 antibody. The hu4-1BBIg fusion protein contained a site for cleavage by the protease thrombin which was situated between the 4-1BB and the Ig portion of the molecule. Animals were immunized with 40 $\mu$g of H4-1BB intraperitonally (i.p.) in RIBI adjuvant (RIBI Immunochemical) and subsequently boosted i.p. with 20–40 $\mu$g of hu4-1BB-Ig or H4-1BB in which the Ig portion of the molecule was cleaved by thrombin digestion. Three days prior to the fusion, animals were boosted i.p. and intravenous (i.v.) with 20 $\mu$g of hu4-1BB. For the fusion, spleen and lymph nodes were harvested from an immunized animal and fused with X63-Ag8.653 mouse myeloma cell line using standard protocols (J. Kearney et al., J. Immunol. 123:1548–1550 (1979); J. Lane, Immunol. 81:223–228 (1985)). Cell suspensions from each fusion were seeded into 96-well cell culture plates at 100,000 cells per well.

B. Screening and Cloning

To determine specificity of the mAbs to human 4-1BB, cell culture supernatants were screened by an ELISA (enzyme-linked immunosorbent assay) method. Cell culture supernatants were tested on plates coated with purified hu4-1BBIg fusion protein (0.2 $\mu$g/ml), or against a similarly constructed irrelevant fusion protein, CTLA4-Ig (0.2 $\mu$g/ml). Soluble human Ig (50 $\mu$g/ml) was added to block anti-human Ig reactivity. Cell culture supernatants were incubated for two hours at ambient temperature, wells were washed and a peroxidase-conjugated goat anti-rat IgG antibody detected the binding of the antibodies. Reactivity of the supernatants with H4-1BB and not with CTLA4-Ig revealed the presence of an antibody specific for human 4-1BB. Positive master wells were cloned by a limiting dilution method.

Monoclonal antibodies were further characterized to determine their ability to block 4-1BB-4-1BBL interaction and for their capacity to induce IFN-γ synthesis in vitro. These studies led to the selection of mAb 39E3, an IgG1, non-blocking mAb that induced IFN-γ synthesis in co-stimulation assays. The invention also includes the hybridoma cells producing the mAb 39E3 (ATCC Accession Number ATCC-PTA-5326). The 39E3 mAb was affinity purified on protein G by standard methods (Gammabind Plus, Pharmacia, Mich.), and eluted with Immunopure Ig Elution buffer. The eluted antibody was dialyzed against PBS (phosphate buffered saline) before use. The endotoxin concentration of the purified material used in in vitro co-stimulatory assays was<than 0.5 EU/mg.

II. Construction of a Humanized 39E3 Antibody

To minimize the immunogenicity of the rat anti-human 4-1BB antibody when administered to humans, a humanized form of the antibody was generated in which the rat hypervariable regions of the antibody (CDR) were grafted onto human framework sequences. In addition, the antibody was made of the IgG4 isotype because of the reduced effector functions of this isotype. A mutation in the hinge region of the IgG4 was introduced to reduce the heterogeneity of disulfide formation (S. Angal et al., Molec. Immunol.vol.30, 105–108, 1993).

A. Humanization of Variable Regions of anti-H4-1BB mAb 39E3

1. Isolation of RNA cDNA Synthesis and PCR (Polymerase Chain Reaction) Amplification RNA was isolated from 39E3 hybridoma cells using an mRNA isolation kit (Stratagene, LaJolla, Calif.). The cDNA was generated from the RNA using the SuperScript RT-PCR kit (Gibco, BRL, Rockville, Md.). The cDNA was generated using an IgG1-specific or a C[kappa]-specific anti-sense primer to obtain the VH and VL regions, respectively. The primers were designed from published sequences for mouse and rat immunoglobulins. The cDNAs were purified using GENECLEAN. (Bio101, LaJolla, Calif.) and subsequently polyG-tailed with 10 mM dGTP and terminal deoxynucleotidyl transferase (Stratagene, Lajolla, Calif.) for 1 hour at 37° C. Poly G-tailed cDNAs were purified using GENECLEAN. Two $\mu$l of each cDNA were amplified by anchor-PCR (Saiki et al., 1988. Science 239:487–491) in a total volume of 100 $\mu$l using 20 $\mu$mol of each dNTP, 100 pmol of sense and antisense primers, and 2U Taq polymerase. The sense primer contained a region complementary to the polyG tail (Loh et al., 1989. Science 243:217–220). Reactions were carried out in a Perkin-Elmer Cetus thermal cycler (Norwalk, Conn.) with a 33 cycle program of 30 sec. denaturation at 94° C., 90 sec. annealing at 45° C., and 90 sec. extension at 72° C.

PCR-amplified VL and VH fragments were digested with EcoR I and Xba I, ligated into the pUC18 vector and transformed in DH5α *E. coli* (Gibco, BRL, Rockville, Md.).

2. Parental Antibody Variable Light and Heavy Sequences

Clones containing the VL or VH were identified by standard DNA sequencing techniques. The deduced amino acid sequence for clone 39E3 VL and VH, respectively, are provided in SEQ ID NOS:1 and 2.

B. Determination of Human Templates for 39E3 VL and VH

The rat 39E3 VL (kappa) and VH sequences were used to search the IgGe (germline) data set for rat germline nucleotide sequences with the closest homology to 39E3 VL with a FASTA search using only nucleotides encoding the mature peptide. This search produced two rat sequences with high homology, the best match designated "RNIGKY3" (GenBank Accession Number X16129).

The human germline amino acid sequence with closest homology to 39E3 VL was determined by performing a FASTA search on the IgP (protein) data set. This data set contained both germline and rearranged sequences. After discarding the rearranged sequences, the best homology match was found with the germline sequence designated "HKV4-1" (GenBank Accession Number Z00023).

The rat nucleotide sequence with the closest homology to 39E3 VH was also determined by performing a BLAST search of the rat cDNA data set using only nucleotides encoding the mature peptide as the query sequence. The search resulted in the rat immunoglobulin variable region sequence (GenBank Accession Number M87785) which showed significantly better homology than the other rat sequences.

The human germline amino acid sequence with the closest homology to 39E3 VH was determined by performing a FASTA search on the IgP data set. The best match was found with the "hhv3–7" germline sequence (GenBank Accession Number Z12354).

C. Refinement of 39E3 VL and VH Humanization Templates.

The canonical loop structures for the antigen binding loops L1, L2, and L3 of the VL domain and H1 and H2 of the VH domain were identified, and conserved residues that were defined as structural determinants (C. Chothia et al., J. Mol. Biol. 196:901 (1987); A. Lesk et al., In Antibody Engineering, A Practical Guide, W. H. Freeman and Co., pp 1–38 (1992)) were retained as rat residues.

The refined VL and VH humanization templates were used to search the Brookhaven databank for homologous sequences in which the crystal structure had been solved.

D. Determination of the J-region Templates

The best human J kappa sequence was selected by homology to the rat J kappa sequence in E. Kabat et al., Sequences of Proteins of Immunological Interest, 4th Edition, U.S. Health and Human Services, Washington, D.C. (1987). Similarly, the best human JH sequence was selected by homology to the rat JH sequence in E. Kabat et al., supra. The proposed sequences were then used to identify antibodies for which three-dimensional structures were available with the closest possible sequence match. This information was used to explore possible incompatible contact places (domain-domain interactions and framework-loop interactions) but none were found.

E. Humanization of the 39E3 VL

The oligonucleotide primers used to humanize the 39E3 VL are listed in Table 1.

TABLE 1

| Oligonucleotide Primer | Sequence |
|---|---|
| 39E3 VL-for1 | SEQ ID NO: 9 |
| 39E3 VL-for2 | SEQ ID NO: 10 |
| 39E3 VL-for3 | SEQ ID NO: 11 |
| 39E3 VL-Rev1 | SEQ ID NO: 12 |
| 39E3 VL-Rev2 | SEQ ID NO: 13 |

The amplified humanized 39E3 VL DNA was then ligated into pUC19 and was used to transform *E. coli* (strain DH50 alpha) per standard techniques. Plasmid DNA from individual clones was sequenced to verify proper fragment assembly of the humanized 39E3 VL.

F. Humanization of the 39E3 VH

The oligonucleotide primers used to humanize the 39E3 VH are listed in Table 2.

TABLE 2

| Oligonucleotide Primer | Sequence |
|---|---|
| 39E3 VH-for1 | SEQ ID NO: 14 |
| 39E3 VH-for2 | SEQ ID NO: 15 |
| 39E3 VH-for3 | SEQ ID NO: 16 |

TABLE 2-continued

| Oligonucleotide Primer | Sequence |
|---|---|
| 39E3 VH-for4 | SEQ ID NO: 17 |
| 39E3 VH-rev1 | SEQ ID NO: 18 |
| 39E3 VH-rev2 | SEQ ID NO: 19 |
| 39E3 VH-rev3 | SEQ ID NO: 20 |

The amplified humanized 39E3 VH DNA was then ligated into pUC19 and was used to transform *E. coli* (strain DH5 α) per standard techniques. Plasmid DNA from individual clones was sequenced to verify proper fragment assembly of the humanized 39E3 VH.

G. Generation of a Cell Line Producing Humanized 39E3.G4 Antibody

A Chinese hamster ovary cell line (CHO DG-44) was transfected with the plasmid expression vectors coding the heavy and light chain of 39E3. The heavy and light chains of 39E3 were cloned into pD17 and pD16 expression vectors, respectively. Both vectors are derived from the pcDNA3, and contain the murine dihydrofolate reductase (DHFR) gene under the control of the enhancerless SV40 promoter. Transfectants were grown up and selected using increasing concentrations of methotrexate (MTX). In vitro assays were performed to confirm that the humanization procedure did not alter the characteristics of the 39E3 antibody.

FIG. 1 shows a plasmid map of pD17-H39E3-2.h4a which contains a nucleotide sequence of 7033 nucleotides (SEQ ID NO:3) that encodes a heavy chain amino acid sequence of 460 amino acids (SEQ ID NO:5). FIGS. 2A–2G show the nucleotide sequence of the plasmid pD17-H39E3-2.h4a (coding strand (SEQ ID NO:3) and complementary strand (SEQ ID NO:4)) and the heavy chain amino acid sequence (SEQ ID NO:5) encoded by nucleotides 693 to 2071 of the coding strand (SEQ ID NO:3). As shown in FIGS. 2A–2G, the heavy chain amino acid sequence includes a CDR1 comprising amino acids 50 to 54 of SEQ ID NO:5, a CDR2 comprising amino acids 69 to 85 of SEQ ID NO:5, and a CDR3 comprising amino acids 118 to 122 of SEQ ID NO:5.

Figure 3:
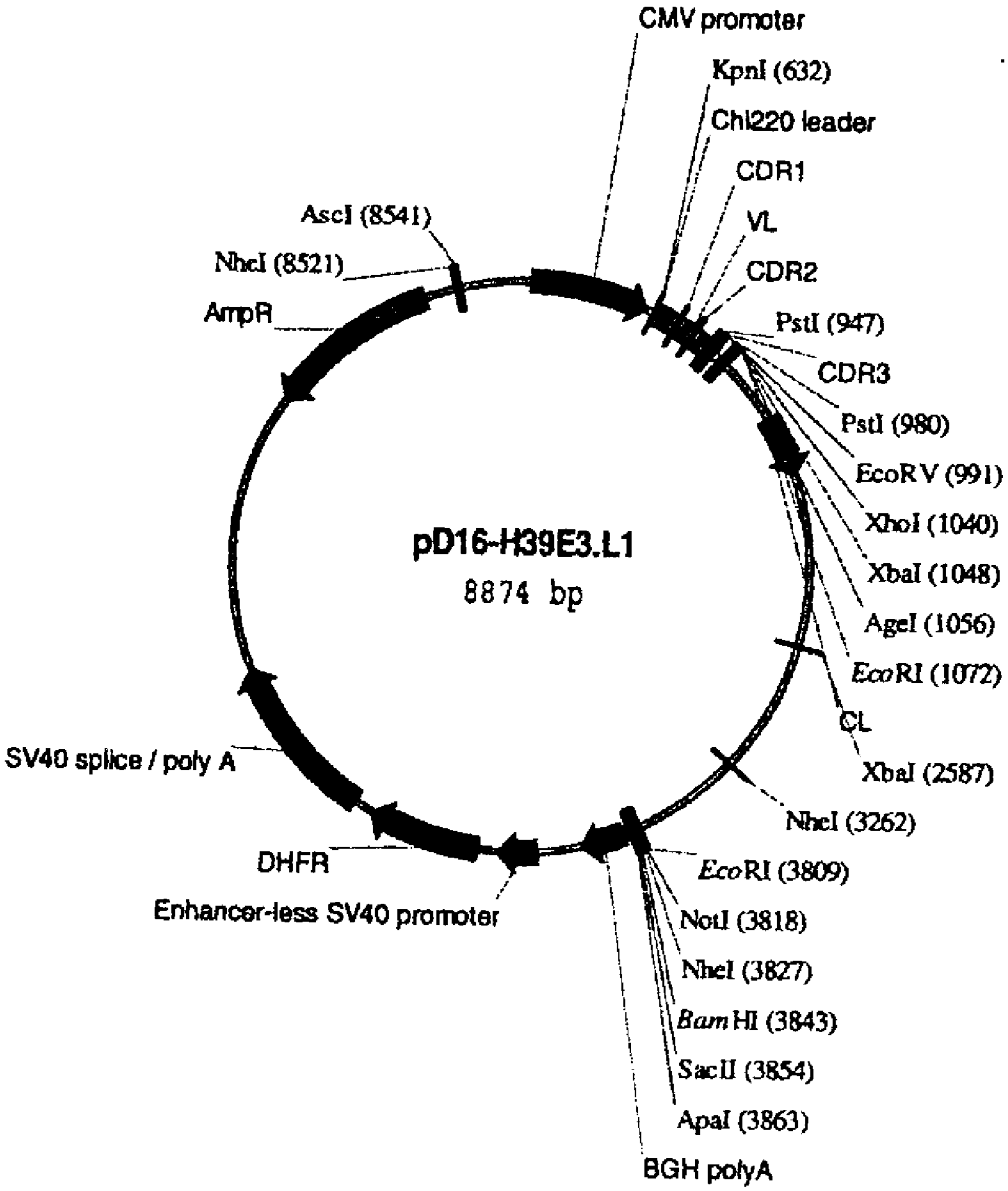
FIG. 3 shows a plasmid map of pD16-H39E3.L1.

FIG. 3 shows a plasmid map of pD16-H39E3.L1 which contains a nucleotide sequence of 8874 nucleotides (SEQ ID NO:6) that encodes a light chain amino acid sequence of 240 amino acids (SEQ ID NO:8). FIGS. 4A–4H show the nucleotide sequence of the plasmid pD16-H39E3.L1 (coding strand (SEQ ID NO:6) and complementary strand (SEQ ID NO:7)) and the light chain amino acid sequence (SEQ ID NO:8) encoded by nucleotides 633 to 1034 and 1409 to 1726 of the coding strand (SEQ ID NO:6). As shown in FIGS. 4A–4H, the light chain amino acid sequence includes a CDR1 comprising amino acids 44 to 60 of SEQ ID NO:8, a CDR2 comprising amino acids 76 to 82 of SEQ ID NO:8, and a CDR3 comprising amino acids 115 to 123 of SEQ ID NO:8.

Single-stranded DNA isolated and the H and L chain variable region genes of the humanized antibodies of the invention was sequenced by the fluorescent dideoxynucleotide termination method (Perkin-Elmer, Foster City, Calif.).

III. In Vitro Characterization of hu39E3.G4

In vitro studies were conducted with the humanized form of 39E3, hu39E3.G4 to compare its activities to the parent mAb, 39E3.

A. Kinetic Analysis of Anti-4-1BB Antibodies

Kinetic binding studies to show the binding affinity of hu39E3.G4 to 4-1BB were performed using surface plasmon resonance to investigate the kinetic properties of mAb 39E3 and hu39E3.G4. These studies were carried out on a BIAcore 3000 instrument (BIAcore Inc., Piscataway, N.J.). Dilutions of the antibodies were injected under identical conditions over sensorchip surfaces of immobilized H4-1BB.

Human 4-1BB receptor was immobilized covalently to a low density on a carboxy-methylated dextran surface of a BIAcore sensorchip (BIAcore Inc., Piscataway, N.J.). Through primary amino groups the fusion protein, injected at 2 μg/mL in 10 mM acetate buffer, pH 5.0, bind to an EDC/NHS-activated surface. Unoccupied active esters were subsequently blocked by injection of an excess of ethanolamine. After regenerating with 10 mM glycine, pH 2.0 the surface was ready for binding studies. Antibodies 39E3 and hu39E3.G4 were diluted to concentrations between 10 nM and 100 nM using HBS-EP buffer. All mAb dilutions were injected over two flow cells (FC) at a flow rate of 25 μl/minute. FC1 served as a negative control, FC2 had low density of human 4-1BB (557 RU). Bound anti-human 4-1BB mAbs were removed by regeneration with 10 mM Glycine pH 1.75.

Figure 5:
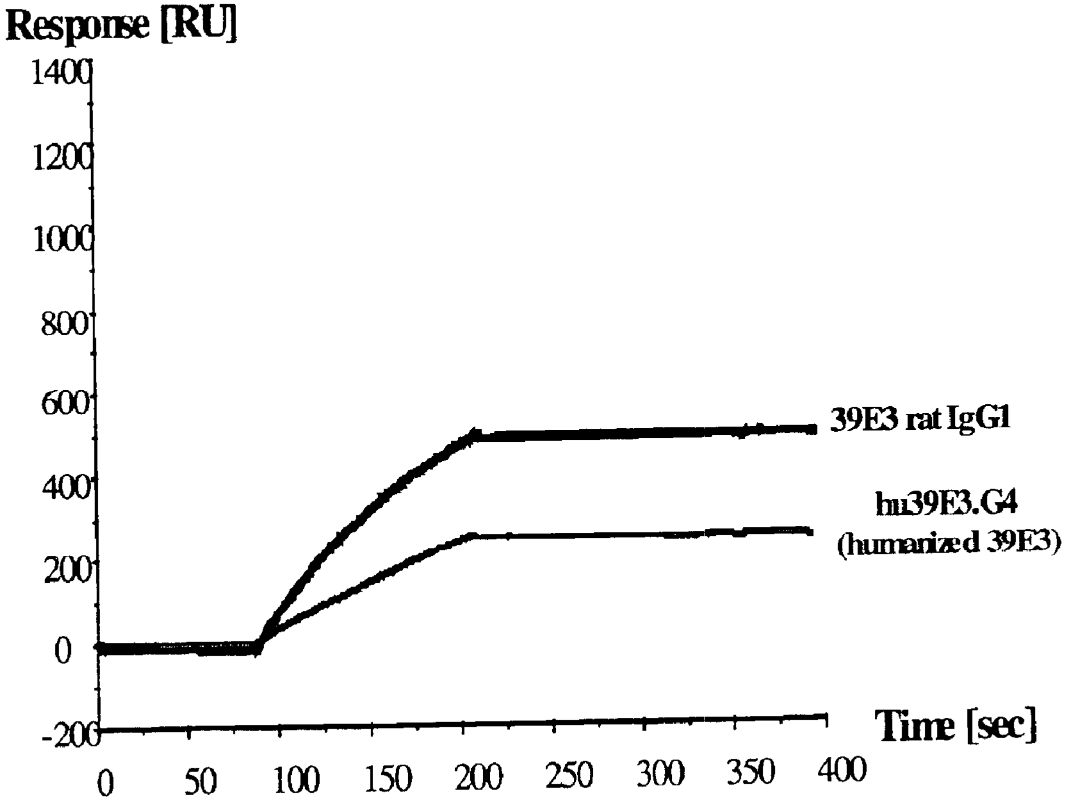
FIG. 5 shows the binding affinities of anti-human-4-1BB antibodies at 100 nM concentration to immobilized H4-1BB.

Kinetic parameters were calculated with BIAevaluation program (version 3.1) (BIAcore Inc., Piscataway, N.J.). A global curve fit analysis was performed using a Bivalent Analyte Model (BIAcore Inc. Piscataway, N.J.). As shown in FIG. 5, the global fit analysis algorithm of the BIAevaluation software finds the single set of kinetic constants $k_a$ and $k_d$ that best fit all the association and dissociation data at the same time. The binding affinities for the parental mAb, 39E3, and the humanized anti-H4-1BB mAb are shown below in Table 3.

TABLE 3

| Antibody | Type | $K_{a1}$ (1/Ms) | $K_{d1}$ (1/s) | $K_{A1}$ [1/M] | $K_{D1}$ [nM] |
|---|---|---|---|---|---|
| 39E3 | rat $IgG_1$ | $7.07 \times 10^3$ | $4.77 \times 10^{-5}$ | $1.48 \times 10^8$ | 6.7 |
| hu39E3.G4 | humanized $IgG_4$ | $4.74 \times 10^3$ | $2.53 \times 10^{-5}$ | $1.87 \times 10^8$ | 5.3 |

Taken together, the studies showed that hu39E3.G4 binds to H4-1BB with an on- and off-rate similar to its parental antibody,39E3, with affinities of 5.3 nM for hu39E3.G4 and 6.7 nM for the parental form.

B. Flow Cytometric Analyses

Figure 6A:
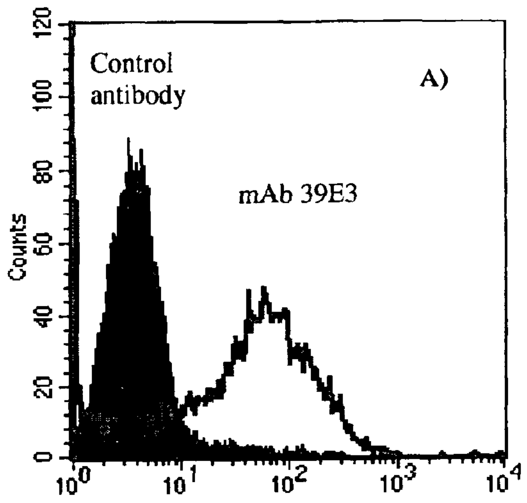
FIG. 6 shows that mAb 39E3 (parental antibody) (A) and hu39E3.G4 antibody (B) bind to PMA and ionomycin-stimulated CEM cells.
Figure 6B:
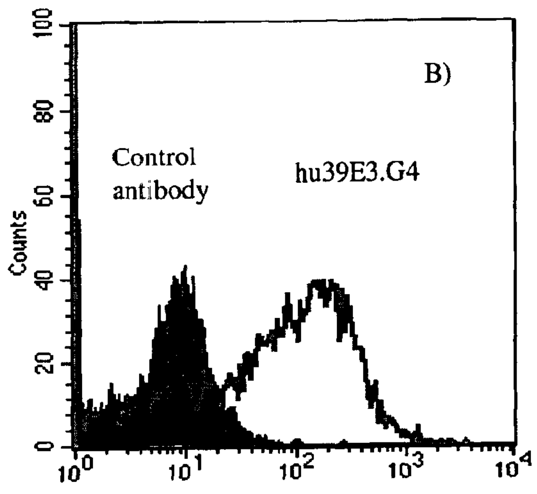

Flow cytometric analyses were conducted to determine binding of hu39E3.G4 and 39E3 to 4-1BB expressed on activated CEM cells (ATCC-CRL2265). Upregulation of 4-1BB on CEM cells was obtained by activation with PMA (10 ng/ml) and ionomycin (1 μM) for 18 hours. Activated cells, but not unstimulated cells, bound to 4-1BBL but not a protein control. For these studies, $1\times10^6$ activated CEM cells were stained with 1 to 10 μg of the anti-4-1BB antibodies hu39E3.G4 and 39E3. Following incubation for 45 minutes on ice, cells were washed and incubated with a fluorescein-conjugated goat anti-rat IgG antibody or fluorescein conjugated goat anti-human IgG to detect binding of mAb 39E3 or hu39E3.G4, respectively. As shown in FIG. 6, the results from these analyses indicated that these antibodies did not show binding to unstimulated cells and their binding to PMA-ionomycin activated CEM was similar.

C. Hu39E3.G4 Does Not Block 4-1BB-4-1BBL Interaction

The antibodies were further characterized for their ability to affect 4-1BB receptor-ligand interaction. All experiments were carried out on a BIAcore 3000 instrument (BIAcore Inc., Piscataway, N.J.). H4-1BB was immobilized covalently to a high density on a carboxy-methylated dextran surface of a BIAcore sensorchip (BIAcore Inc., Piscataway, N.J.). Injections were conducted at 2 μg/mL in 10 mM acetate buffer, pH 5.0. Unoccupied active esters were subsequently blocked by injection of an excess of ethanolamine. Regeneration of the surface was done with 10 mM glycine, pH 2.0.

Purified samples of anti-4-1BB antibodies were diluted to concentrations between 200 and 1000 nM using HEPES buffered saline, pH 7.4, supplemented with 0.15 M NaCl and 0.005% surfactant P20 (HBS-EP). H4-1BB Ligand-CD8 fusion proteins (H4-1BBL) were used as source of H4-1BBL. To investigate whether hu39E3.G4 or mAb 39E3 have any effect on the binding of H4-1BBL to H4-1BB, experiments were conducted in which H4-1BBL was injected prior to anti-4-1BB antibodies, or vice versa wherein antibodies were injected before addition of H4-1BBL. Injections were performed at a flow rate of 5 μL/min. Bound ligand and antibodies were removed by regeneration with 10 mM glycine buffer, pH 2.0. As shown below in Table 4 neither hu39E3.G4 nor mAb 39E3 affected the binding of H4-1BBL to H4-1BB.

TABLE 4

| Analyte | Isotype | Bound At First Injection | Antibody Bound After Ligand Injection | Ligand Bound After Antibody Injection |
|---|---|---|---|---|
| Ligand | | 619 | 81 | 81 |
| 39E3 | rat IgG1 | 1010 | 908 | 540 |
| hu39E3.G4 | human. IgG4 | 880 | 767 | 552 |

D. In Vitro Co-stimulation Assays

To demonstrate that hu39E3.G4 was an agonistic antibody, in vitro co-stimulation assays were carried out to show that when the antibody was added to human T cells, the T cells were stimulated with a sub-optimal concentration of CD3 and they enhanced IFN-γ synthesis.

Figure 7:
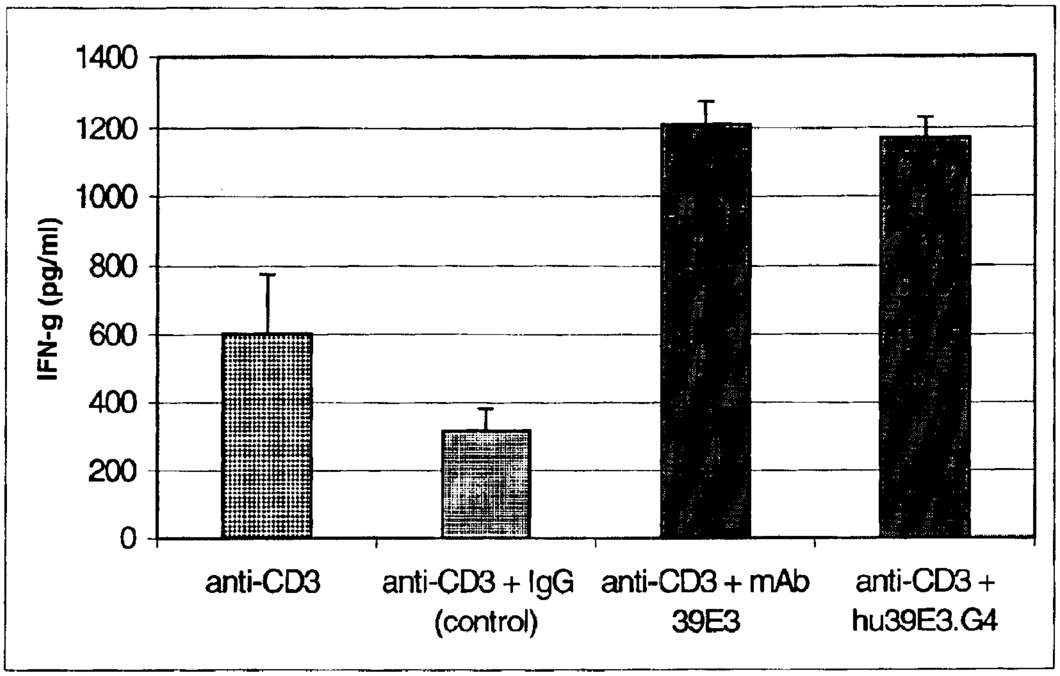
FIG. 7 shows the induction of IFN-γ by co-stimulation of human T-cells with anti-CD3 and anti-4-1BB mAb 39E3 and hu39E3.G4.

This was demonstrated by assessing the ability of the anti-human 4-1BB hu39E3.G4 and mAb 39E3 to induce cytokine synthesis in vitro. Human PBMC were isolated from healthy volunteers by Histopaque-1077 (Sigma, St Louis, Mo.) density-gradient centrifugation, and T-cells were further purified by rosetting with sheep red blood cells. T-cells ($1\times10^6$ cells/ml) were cultured in the presence of anti-CD3 antibody (HIT3a, Pharmingen, San Diego, Calif.) at 0.1 μg/ml and co-stimulated with the anti-human 4-1BB mAbs hu39E3.G4 or 39E3 (20 μg/ml) or a control antibody. Supernatants were harvested 72 hours later and assayed for IFN-γ by an ELISA kit available commercially (Pharmingen, San Diego, Calif.). As shown in FIG. 7, this study revealed that production of IFN-γ was enhanced in the presence of the anti-4-1BB antibodies hu39E3.G4 and 39E3 in the presence of sub-optimal concentrations of anti-CD3. Cytokine concentrations in supernatants are expressed as mean±SD of triplicate wells.

IV. Anti-Tumor Efficacy Studies with Anti-Murine 4-1BB Antibody, mAb 1D8

In that hu39E3.G4 did not recognize murine 4-1BB, the anti-tumor effect of this antibody could not be evaluated in murine tumor models. Therefore, a monoclonal antibody to murine 4-1BB, mAb 1D8, which closely matched the properties of hu39E3.G4, was used to assess the suitability of this antibody as an anti-cancer agent. Monoclonal antibody 1D8 is a rat IgG2*a* antibody that binds to murine 4-1BB, but does not cross-react with H4-1BB. Monoclonal antibody 1D8, similar to hu39E3.G4, is not immunogenic in mice, does not block the 4-1BB-4-1BB ligand interaction, induces IFN-γ synthesis in co-stimulation assays, and does not fix complement.

In vivo anti-tumor efficacy was evaluated in two different settings: as monotherapy and following implantation of irradiated tumor cells (cell-based vaccine). These effects were tested in two tumor models, M109 lung carcinoma and Lewis Lung/LM carcinoma.

A. M109 Lung Carcinoma Model

Balb/c mice (8–10 weeks old) were implanted s.c. (subcutaneous) with a 1% brie of M109 tumors. Three days later the mice were randomized and separated into three groups, each of 10 mice. The treatment groups consisted of a control group, which received phosphate buffered saline (PBS, control vehicle), a group receiving an isotype matched immunoglobulin at the same dose as mAb 1D8, and a third group which received mAb 1D8 at 200 μg/mouse, every 7 days for three doses. For the vaccination protocol, mice received a s.c. vaccination of irradiated M109 cells (2% brie, 30 Gy, 23 minutes) two weeks prior to implantation of viable tumor cells on the opposite flank (1% brie). Treatments were administered one day following implantation of tumor cells.

Figure 8A:
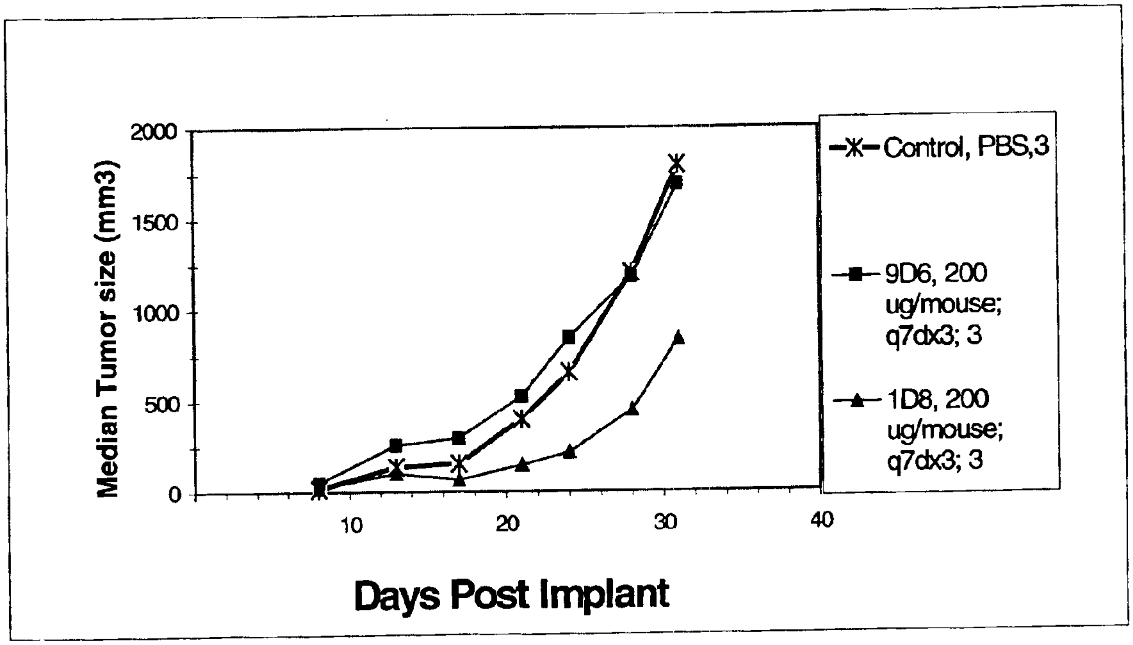
FIGS. 8A and 8B show the anti-tumor effect of antibody 1D8 against the M109 lung carcinoma model as a single agent (FIG. 8A) or in mice previously immunized with irradiated M109 tumor cells (FIG. 8B).
Figure 8B:
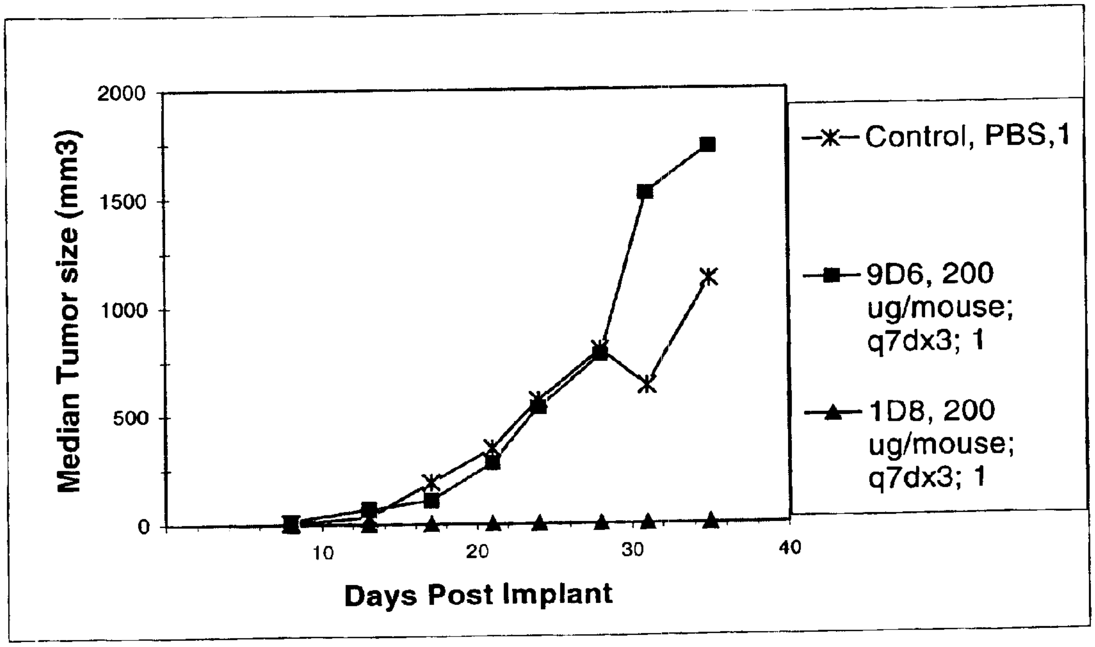

As shown in FIG. 8A, the mAb 1D8 induced a modest, but significant, inhibitory effect on tumor growth when used as monotherapy. However, when combined with a cell based vaccine mAb 1D8 produced a significant reduction of tumor incidence in that M109 tumors did not grow in the majority of 1D8 treated mice, as shown in FIG. 8B.

B. Lewis Lung/LM Carcinoma

Figure 9A:
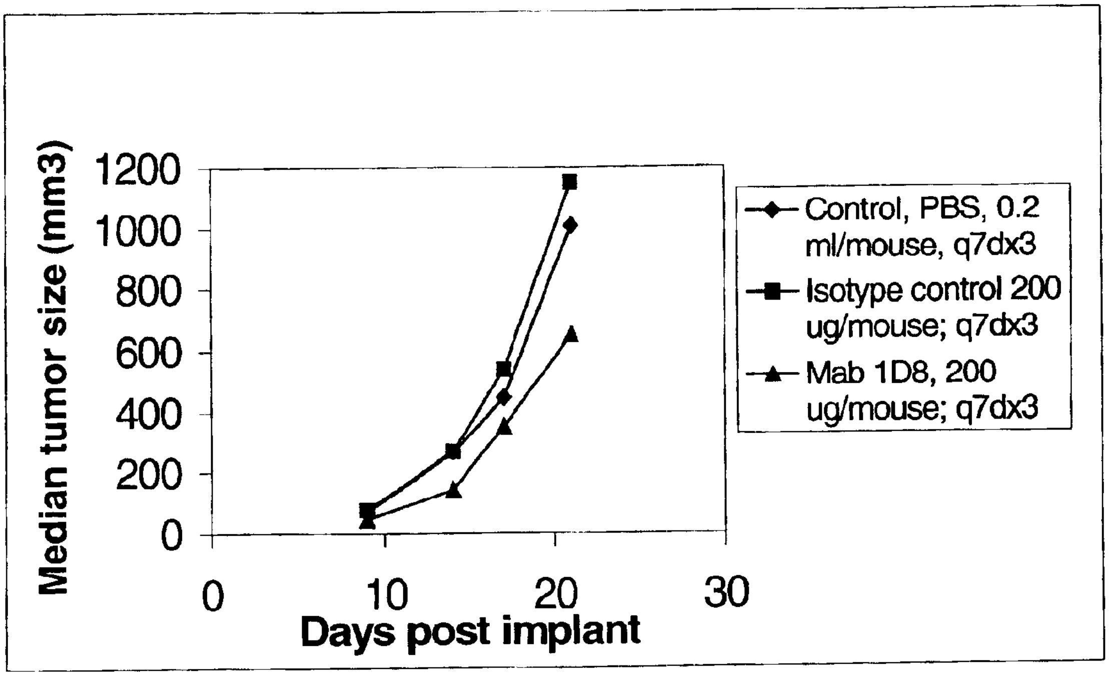
FIGS. 9A and 9B show the anti-tumor effect of antibody 1D8 against the Lewis Lung/LM lung carcinoma model as a single agent (FIG. 9A) or in mice previously immunized with irradiated Lewis Lung/LM tumor cells (FIG. 9B).
Figure 9B:
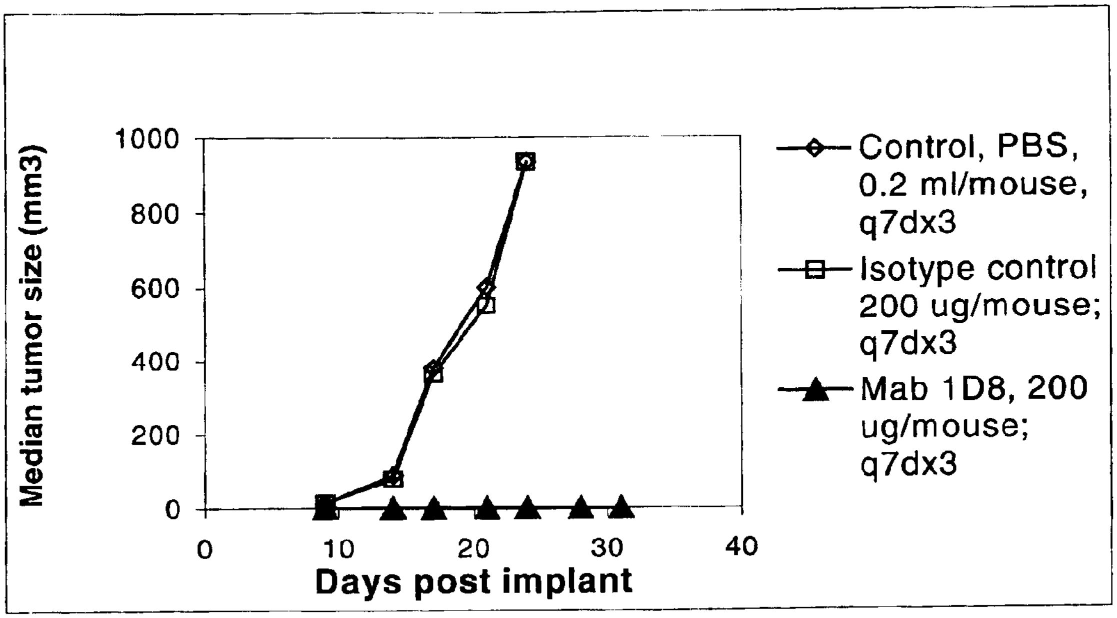

Similar experiments were conducted with the Lewis Lung/LM carcinoma tumor. C57/BL6 mice were implanted s.c. with $1\times10^5$ Lewis Lung/LM cells. For the vaccination protocol, mice received a s.c. injection of irradiated Lewis Lung/LM cells ($1\times10^5$ Lewis Lung/LM cells, 30 Gy, 23 min). Antibody treatments (200 μg/mouse) were administered i.v. weekly for three doses. When mAb 1D8 was administered as a single agent, mAb 1D8 had no effect on tumor growth (FIG. 9A). However, in mice previously implanted with irradiated tumor cells two weeks earlier, mAb 1D8 significantly inhibited tumor growth (FIG. 9B).

C. Anti-Tumor Activity of Anti-4-1BB Antibody Is Dependent on Production of IFN-γ

Since anti-4-1BB antibodies induced IFN-γ synthesis in in vitro co-stimulatory assays, studies were conducted to determine whether IFN-γ played a role in the anti-tumor activity of anti-4-1BB mAbs.

Figure 10:
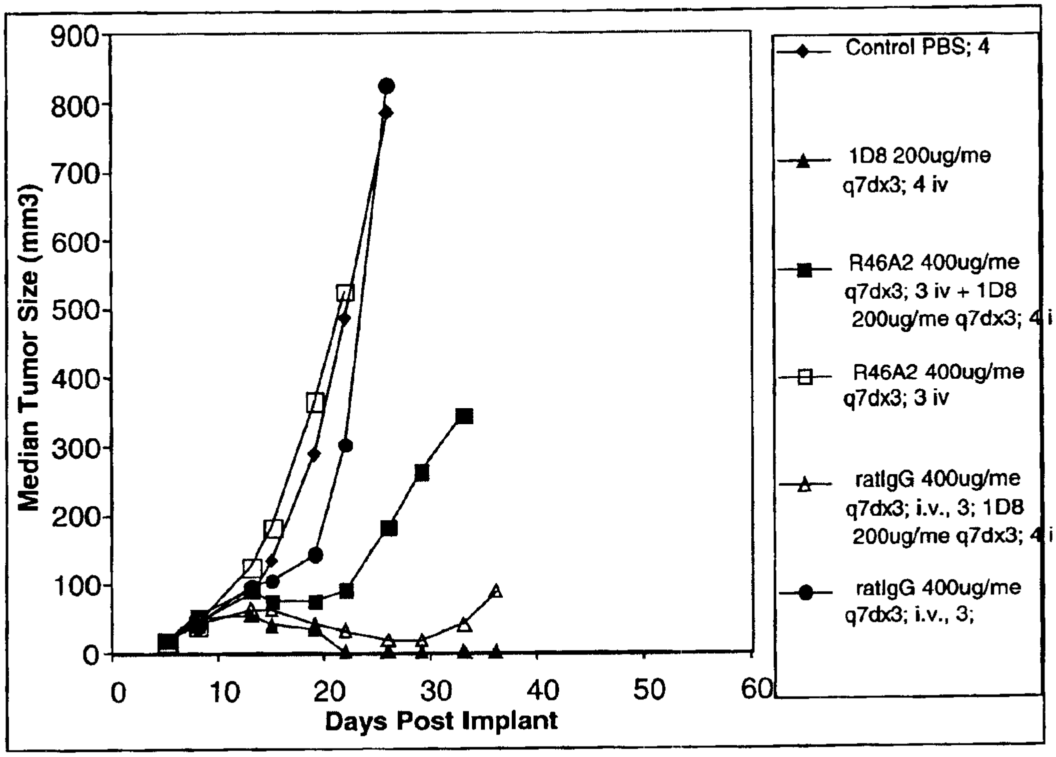
FIG. 10 shows that the anti-tumor effect of mAb 1D8 is reduced in the presence of an IFN-γ neutralizing antibody.

DBA mice were implanted with P815 cells ($1\times10^5$ cells) s.c., on day 0. Three days later, the mice received 100 or 400 μg/mouse of a neutralizing anti-IFN-γ antibody (RA46A2) alone or in combination with an efficacious dose of anti-4-1BB antibody, mAb 1D8 (200 μg/mouse). Control groups consisted of mice treated with vehicle (PBS), isotype control antibody (200 μg/mouse), mAb 1D8 alone (200 μg/mouse), and mAb 1D8 (200 μg/mouse) plus the isotype control antibody (200 μg/mouse). The results of this study (FIG. 10) indicate that addition of an IFN-γ neutralizing antibody partially reduced the anti-tumor effects of mAb 1D8, suggesting that induction of IFN-γ is one of the mechanisms by which the anti-4-1BB mAb exerts its anti-tumor effects. It is expected that hu39E3.G4 will have the anti-tumor activities observed with mAb 1D8.

Although the invention has been described in some detail by way of illustration and example for purposes of clarity and understanding, it will be apparent that certain changes and modifications may be practiced within the scope of the appended claims.

What is claimed is:

1. An isolated antibody that comprises a light chain and a heavy chain, wherein:

said heavy chain includes a CDR1 comprising amino acids 50 to 54 of SEQ ID NO:5, a CDR2 comprising amino acids 69 to 85 of SEQ ID NO:5, and a CDR3 comprising amino acids 118 to 122 of SEQ ID NO:5; and said light chain includes a CDR1 comprising amino acids 44 to 60 of SEQ ID NO:8, a CDR2 comprising amino acids 76 to 82 of SEQ ID NO:8, and a CDR3 comprising amino acids 115 to 123 of SEQ ID NO:8.

2. The antibody of claim 1 that is an IgG4 antibody.

3. An isolated antibody that comprises the amino acid sequence of SEQ ID NO:5 and SEQ ID NO:8.

4. A pharmaceutical composition comprising the antibody of claim 1 and a pharmaceutically acceptable carrier.

5. A pharmaceutical composition comprising the antibody of claim 3 and a pharmaceutically acceptable carrier.

* * * * *

SEQUENCE LISTING

```
<160> NUMBER OF SEQ ID NOS: 20

<210> SEQ ID NO 1
<211> LENGTH: 104
<212> TYPE: PRT
<213> ORGANISM: Rattus norvegicus

<400> SEQUENCE: 1

Asp Ile Ile Met Thr Gln Ser Pro Phe Ser Leu Ala Val Ser Glu Gly
1               5                   10                  15

Glu Met Val Thr Met Asn Cys Lys Ser Ser Gln Ser Leu Leu Ser Ser
            20                  25                  30

Gly Asn Gln Lys Asn Tyr Leu Ala Trp Tyr Gln Gln Lys Pro Gly Gln
        35                  40                  45

Pro Pro Glu Leu Leu Ile Tyr Tyr Ala Ser Thr Arg Gln Ser Gly Val
    50                  55                  60

Pro Asp Arg Phe Ile Gly Ser Gly Ser Gly Thr Asp Phe Leu Thr Leu
65                  70                  75                  80

Thr Ile Ser Asp Val Gln Ala Glu Asp Leu Ala Asp Tyr Tyr Cys Leu
                85                  90                  95

Gln Tyr Asp Arg Tyr Pro Phe Thr
            100
```

-continued

<210> SEQ ID NO 2
<211> LENGTH: 103
<212> TYPE: PRT
<213> ORGANISM: Rattus norvegicus

<400> SEQUENCE: 2

```
Glu Val Gln Leu Val Glu Ser Gly Gly Gly Leu Val Lys Pro Gly Ala
1               5                   10                  15

Ser Leu Lys Leu Ser Cys Val Ala Ser Gly Phe Thr Phe Ser Asp Tyr
            20                  25                  30

Trp Met Ser Trp Val Arg Gln Thr Pro Gly Lys Thr Met Glu Trp Ile
        35                  40                  45

Gly Asp Ile Lys Asn Asp Gly Ser Tyr Thr Asn Tyr Ala Pro Ser Leu
    50                  55                  60

Thr Asn Arg Phe Thr Ile Ser Arg Asp Asn Ala Arg Ser Thr Leu Tyr
65                  70                  75                  80

Leu Gln Met Asn Asn Val Arg Ser Glu Asp Thr Ala Thr Tyr Tyr Cys
                85                  90                  95

Thr Arg Glu Leu Thr Gly Thr
            100
```

<210> SEQ ID NO 3
<211> LENGTH: 7033
<212> TYPE: DNA
<213> ORGANISM: Artificial
<220> FEATURE:
<223> OTHER INFORMATION: Synthetic

<400> SEQUENCE: 3

```
cgatgtacgg gccagatata cgcgttgaca ttgattattg actagttatt aatagtaatc      60

aattacgggg tcattagttc atagcccata tatggagttc cgcgttacat aacttacggt     120

aaatggcccg cctggctgac cgcccaacga cccccgccca ttgacgtcaa taatgacgta     180

tgttcccata gtaacgccaa tagggacttt ccattgacgt caatgggtgg actatttacg     240

gtaaactgcc cacttggcag tacatcaagt gtatcatatg ccaagtacgc cccctattga     300

cgtcaatgac ggtaaatggc ccgcctggca ttatgcccag tacatgacct tatgggactt     360

tcctacttgg cagtacatct acgtattagt catcgctatt accatggtga tgcggttttg     420

gcagtacatc aatgggcgtg gatagcggtt tgactcacgg ggatttccaa gtctccaccc     480

cattgacgtc aatgggagtt tgttttggca ccaaaatcaa cgggactttc caaaatgtcg     540

taacaactcc gccccattga cgcaaatggg cggtaggcgt gtacggtggg aggtctatat     600

aagcagagct ctctggctaa ctagagaacc cactgcttac tggcttatcg aaattaatac     660

gactcactat agggagaccc aagcttggta ccatggactg gacctggagg atcctcttct     720

tggtggcagc agcaacaggt gcccactccg aagtacaact ggtggagtct ggaggaggtt     780

tggtgcaacc tggggggttct ctgcgactct cttgtgcagc ctcgggattc actttcagtg     840

actactggat gagctgggtt cgtcaggcgc ctggaaaggg cctggagtgg gttgcagata     900

ttaaaaatga tggcagttac acaaactatg caccatccct aacgaatcga ttcacaatct     960

ccagagacaa tgccaagaac tccctgtacc tgcagatgaa ctctctgaga gctgaggaca    1020

cagccgttta ttactgtgct agagaactaa ctgggacttg gggccaagga accatggtca    1080

cagtctcctc agctagcacc aagggcccat ccgtcttccc cctggcgccc tgctccagga    1140

gcacctccga gagcacagcc gccctgggct gcctggtcaa ggactacttc cccgaaccgg    1200

tgacggtgtc gtggaactca ggcgccctga ccagcggcgt gcacaccttc ccggctgtcc    1260
```

-continued

```
tacagtcctc aggactctac tccctcagca gcgtggtgac cgtgccctcc agcagcttgg   1320
gcacgaagac ctacacctgc aacgtagatc acaagcccag caacaccaag gtggacaaga   1380
gagttgagtc caaatatggt ccaccttgcc caccttgccc agcacctgag ttcctggggg   1440
gaccatcagt cttcctgttc ccccaaaac ccaaggacac tctcatgatc tcccggaccc   1500
ctgaggtcac gtgcgtggtg gtggacgtga gccaggaaga ccccgaggtc cagttcaact   1560
ggtacgtgga tggcgtggag gtgcataatg ccaagacaaa gccgcgggag gagcagttca   1620
acagcacgta ccgtgtggtc agcgtcctca ccgtcctgca ccaggactgg ctgaacggca   1680
aggagtacaa gtgcaaggtc tccaacaaag gcctcccgtc ctccatcgag aaaaccatct   1740
ccaaagccaa agggcagccc cgagagccac aggtgtacac cctgccccca tcccaggagg   1800
agatgaccaa gaaccaggtc agcctgacct gcctggtcaa aggcttctac cccagcgaca   1860
tcgccgtgga gtgggagagc aatgggcagc cggagaacaa ctacaagacc acgcctcccg   1920
tgctggactc cgacggctcc ttcttcctct acagcaggct aaccgtggac aagagcaggt   1980
ggcaggaggg gaatgtcttc tcatgctccg tgatgcatga ggctctgcac aaccactaca   2040
cacagaagag cctctccctg tctctgggta aatgatctag agggccctat tctatagtgt   2100
cacctaaatg ctagagctcg ctgatcagcc tcgactgtgc cttctagttg ccagccatct   2160
gttgtttgcc cctcccccgt gccttccttg accctggaag gtgccactcc cactgtcctt   2220
tcctaataaa atgaggaaat tgcatcgcat tgtctgagta ggtgtcattc tattctgggg   2280
ggtggggtgg ggcaggacag caagggggag gattgggaag acaatagcag gcatgctggg   2340
gatgcggtgg gctctatggc ttctgaggcg gaaagaacca gctggggctc tagggggtat   2400
ccccacgcgc cctgtagcgg cgcattaagc gcggcgggtg tggtggttac gcgcagcgtg   2460
accgctacac ttgccagcgc cctagcgccc gctcctttcg ctttcttccc ttcctttctc   2520
gccacgttcg ccgggcctct caaaaaaggg aaaaaaagca tgcatctcaa ttagtcagca   2580
accatagtcc cgcccctaac tccgcccatc ccgcccctaa ctccgcccag ttccgcccat   2640
tctccgcccc atggctgact aatttttttt atttatgcag aggccgaggc cgcctcggcc   2700
tctgagctat tccagaagta gtgaggaggc ttttttggag gcctaggctt ttgcaaaaag   2760
cttggacagc tcagggctgc gatttcgcgc caaacttgac ggcaatccta gcgtgaaggc   2820
tggtaggatt ttatccccgc tgccatcatg gttcgaccat tgaactgcat cgtcgccgtg   2880
tcccaaaata tggggattgg caagaacgga gacctaccct ggcctccgct caggaacgag   2940
ttcaagtact tccaaagaat gaccacaacc tcttcagtgg aaggtaaaca gaatctggtg   3000
attatgggta ggaaaacctg gttctccatt cctgagaaga atcgaccttt aaaggacaga   3060
attaatatag ttctcagtag agaactcaaa gaaccaccac gaggagctca ttttcttgcc   3120
aaaagtttgg atgatgcctt aagacttatt gaacaaccgg aattggcaag taaagtagac   3180
atggtttgga tagtcggagg cagttctgtt taccaggaag ccatgaatca accaggccac   3240
cttagactct ttgtgacaag gatcatgcag gaatttgaaa gtgacacgtt tttcccagaa   3300
attgatttgg ggaaatataa acttctccca gaatacccag gcgtcctctc tgaggtccag   3360
gaggaaaaag gcatcaagta taagtttgaa gtctacgaga agaaagacta acaggaagat   3420
gctttcaagt tctctgctcc cctcctaaag ctatgcattt ttataagacc atgggacttt   3480
tgctggcttt agatctcttt gtgaaggaac cttacttctg tggtgtgaca taattggaca   3540
aactacctac agagatttaa agctctaagg taaatataaa atttttaagt gtataatgtg   3600
ttaaactact gattctaatt gtttgtgtat tttagattcc aacctatgga actgatgaat   3660
```

-continued

```
gggagcagtg gtggaatgcc tttaatgagg aaaacctgtt ttgctcagaa gaaatgccat   3720
ctagtgatga tgaggctact gctgactctc aacattctac tcctccaaaa aagaagagaa   3780
aggtagaaga ccccaaggac tttccttcag aattgctaag ttttttgagt catgctgtgt   3840
ttagtaatag aactcttgct tgctttgcta tttacaccac aaaggaaaaa gctgcactgc   3900
tatacaagaa aattatggaa aaatattctg taacctttat aagtaggcat aacagttata   3960
atcataacat actgtttttt cttactccac acaggcatag agtgtctgct attaataact   4020
atgctcaaaa attgtgtacc tttagctttt taatttgtaa aggggttaat aaggaatatt   4080
tgatgtatag tgccttgact agagatcata atcagccata ccacatttgt agaggtttta   4140
cttgctttaa aaaacctccc acacctcccc ctgaacctga aacataaaat gaatgcaatt   4200
gttgttgtta acttgtttat tgcagcttat aatggttaca aataaagcaa tagcatcaca   4260
aatttcacaa ataaagcatt tttttcactg cattctagtt gtggtttgtc caaactcatc   4320
aatgtatctt atcatgtctg gatcggctgg atgatcctcc agcgcgggga tctcatgctg   4380
gagttcttcg cccaccccaa cttgtttatt gcagcttata atggttacaa ataaagcaat   4440
agcatcacaa atttcacaaa taaagcattt ttttcactgc attctagttg tggtttgtcc   4500
aaactcatca atgtatctta tcatgtctgt ataccgtcga cctctagcta gagcttggcg   4560
taatcatggt catagctgtt tcctgtgtga aattgttatc cgctcacaat tccacacaac   4620
atacgagccg gaagcataaa gtgtaaagcc tggggtgcct aatgagtgag ctaactcaca   4680
ttaattgcgt tgcgctcact gcccgctttc cagtcgggaa acctgtcgtg ccagctgcat   4740
taatgaatcg gccaacgcgc ggggagaggc ggtttgcgta ttgggcgctc ttccgcttcc   4800
tcgctcactg actcgctgcg ctcggtcgtt cggctgcggc gagcggtatc agctcactca   4860
aaggcggtaa tacggttatc cacagaatca ggggataacg caggaaagaa catgtgagca   4920
aaaggccagc aaaaggccag gaaccgtaaa aaggccgcgt tgctggcgtt tttccatagg   4980
ctccgccccc ctgacgagca tcacaaaaat cgacgctcaa gtcagaggtg gcgaaacccg   5040
acaggactat aaagatacca ggcgtttccc cctggaagct ccctcgtgcg ctctcctgtt   5100
ccgaccctgc cgcttaccgg atacctgtcc gcctttctcc cttcgggaag cgtggcgctt   5160
tctcaatgct cacgctgtag gtatctcagt tcggtgtagg tcgttcgctc caagctgggc   5220
tgtgtgcacg aaccccccgt tcagcccgac cgctgcgcct tatccggtaa ctatcgtctt   5280
gagtccaacc cggtaagaca cgacttatcg ccactggcag cagccactgg taacaggatt   5340
agcagagcga ggtatgtagg cggtgctaca gagttcttga agtggtggcc taactacggc   5400
tacactagaa ggacagtatt tggtatctgc gctctgctga agccagttac cttcggaaaa   5460
agagttggta gctcttgatc cggcaaacaa accaccgctg gtagcggtgg tttttttgtt   5520
tgcaagcagc agattacgcg cagaaaaaaa ggatctcaag aagatccttt gatcttttct   5580
acggggtctg acgctcagtg gaacgaaaac tcacgttaag ggattttggt catgagatta   5640
tcaaaaagga tcttcaccta gatcctttta aattaaaaat gaagttttaa atcaatctaa   5700
agtatatatg agtaaacttg gtctgacagt taccaatgct taatcagtga ggcacctatc   5760
tcagcgatct gtctatttcg ttcatccata gttgcctgac tccccgtcgt gtagataact   5820
acgatacggg agggcttacc atctggcccc agtgctgcaa tgataccgcg agacccacgc   5880
tcaccggctc cagatttatc agcaataaac cagccagccg gaagggccga gcgcagaagt   5940
ggtcctgcaa ctttatccgc ctccatccag tctattaatt gttgccggga agctagagta   6000
agtagttcgc cagttaatag tttgcgcaac gttgttgcca ttgctacagg catcgtggtg   6060
```

-continued

```
tcacgctcgt cgtttggtat ggcttcattc agctccggtt cccaacgatc aaggcgagtt   6120

acatgatccc ccatgttgtg caaaaaagcg gttagctcct tcggtcctcc gatcgttgtc   6180

agaagtaagt tggccgcagt gttatcactc atggttatgg cagcactgca taattctctt   6240

actgtcatgc catccgtaag atgcttttct gtgactggtg agtactcaac caagtcattc   6300

tgagaatagt gtatgcggcg accgagttgc tcttgcccgg cgtcaatacg ggataatacc   6360

gcgccacata gcagaacttt aaaagtgctc atcattggaa aacgttcttc ggggcgaaaa   6420

ctctcaagga tcttaccgct gttgagatcc agttcgatgt aacccactcg tgcacccaac   6480

tgatcttcag catcttttac tttcaccagc gtttctgggt gagcaaaaac aggaaggcaa   6540

aatgccgcaa aaaagggaat aagggcgaca cggaaatgtt gaatactcat actcttcctt   6600

tttcaatatt attgaagcat ttatcagggt tattgtctca tgagcggata catatttgaa   6660

tgtatttaga aaaataaaca aataggggtt ccgcgcacat ttccccgaaa agtgccacct   6720

gacgtcgacg gatcgggaga tctgctaggt gacctgaggc gcgccggctt cgaatagcca   6780

gagtaacctt ttttttaat tttattttat tttatttttg agatggagtt tggcgccgat   6840

ctcccgatcc cctatggtcg actctcagta caatctgctc tgatgccgca tagttaagcc   6900

agtatctgct ccctgcttgt gtgttggagg tcgctgagta gtgcgcgagc aaaatttaag   6960

ctacaacaag gcaaggcttg accgacaatt gcatgaagaa tctgcttagg gttaggcgtt   7020

ttgcgctgct tcg                                                      7033
```

<210> SEQ ID NO 4
<211> LENGTH: 7033
<212> TYPE: DNA
<213> ORGANISM: Artificial
<220> FEATURE:
<223> OTHER INFORMATION: Synthetic

<400> SEQUENCE: 4

```
gctacatgcc cggtctatat gcgcaactgt aactaataac tgatcaataa ttatcattag     60

ttaatgcccc agtaatcaag tatcgggtat atacctcaag gcgcaatgta ttgaatgcca    120

tttaccgggc ggaccgactg gcgggttgct gggggcgggt aactgcagtt attactgcat    180

acaagggtat cattgcggtt atccctgaaa ggtaactgca gttacccacc tgataaatgc    240

catttgacgg gtgaaccgtc atgtagttca catagtatac ggttcatgcg gggataact     300

gcagttactg ccatttaccg ggcggaccgt aatacgggtc atgtactgga ataccctgaa    360

aggatgaacc gtcatgtaga tgcataatca gtagcgataa tggtaccact acgccaaaac    420

cgtcatgtag ttacccgcac ctatcgccaa actgagtgcc cctaaaggtt cagaggtggg    480

gtaactgcag ttaccctcaa acaaaaccgt ggttttagtt gccctgaaag gttttacagc    540

attgttgagg cggggtaact gcgtttaccc gccatccgca catgccaccc tccagatata    600

ttcgtctcga gagaccgatt gatctcttgg gtgacgaatg accgaatagc tttaattatg    660

ctgagtgata tccctctggg ttcgaaccat ggtacctgac ctggacctcc taggagaaga    720

accaccgtcg tcgttgtcca cgggtgaggc ttcatgttga ccacctcaga cctcctccaa    780

accacgttgg acccccaaga gacgctgaga gaacacgtcg gagccctaag tgaaagtcac    840

tgatgaccta ctcgacccaa gcagtccgcg gacctttccc ggacctcacc caacgtctat    900

aatttttact accgtcaatg tgtttgatac gtggtaggga ttgcttagct aagtgttaga    960

ggtctctgtt acggttcttg agggacatgg acgtctactt gagagactct cgactcctgt   1020

gtcggcaaat aatgacacga tctcttgatt gaccctgaac cccggttcct tggtaccagt   1080
```

-continued

```
gtcagaggag tcgatcgtgg ttcccgggta ggcagaaggg ggaccgcggg acgaggtcct   1140
cgtggaggct ctcgtgtcgg cgggacccga cggaccagtt cctgatgaag gggcttggcc   1200
actgccacag caccttgagt ccgcgggact ggtcgccgca cgtgtggaag ggccgacagg   1260
atgtcaggag tcctgagatg agggagtcgt cgcaccactg gcacgggagg tcgtcgaacc   1320
cgtgcttctg gatgtggacg ttgcatctag tgttcgggtc gttgtggttc cacctgttct   1380
ctcaactcag gtttatacca ggtggaacgg gtggaacggg tcgtggactc aaggaccccc   1440
ctggtagtca gaaggacaag gggggttttg ggttcctgtg agagtactag agggcctggg   1500
gactccagtg cacgcaccac cacctgcact cggtccttct ggggctccag gtcaagttga   1560
ccatgcacct accgcacctc cacgtattac ggttctgttt cggcgccctc ctcgtcaagt   1620
tgtcgtgcat ggcacaccag tcgcaggagt ggcaggacgt ggtcctgacc gacttgccgt   1680
tcctcatgtt cacgttccag aggttgtttc cggagggcag gaggtagctc ttttggtaga   1740
ggtttcggtt tcccgtcggg gctctcggtg tccacatgtg ggacgggggt agggtcctcc   1800
tctactggtt cttggtccag tcggactgga cggaccagtt tccgaagatg ggtcgctgt    1860
agcggcacct caccctctcg ttacccgtcg gcctcttgtt gatgttctgg tgcggagggc   1920
acgacctgag gctgccgagg aagaaggaga tgtcgtccga ttggcacctg ttctcgtcca   1980
ccgtcctccc cttacagaag agtacgaggc actacgtact ccgagacgtg ttggtgatgt   2040
gtgtcttctc ggagagggac agagacccat ttactagatc tcccgggata agatatcaca   2100
gtggatttac gatctcgagc gactagtcgg agctgacacg gaagatcaac ggtcggtaga   2160
caacaaacgg ggagggggca cggaaggaac tgggaccttc cacggtgagg gtgacaggaa   2220
aggattattt tactccttta acgtagcgta acagactcat ccacagtaag ataagacccc   2280
ccaccccacc ccgtcctgtc gttccccctc ctaacccttc tgttatcgtc cgtacgaccc   2340
ctacgccacc cgagataccg aagactccgc ctttcttggt cgacccccgag atcccccata   2400
ggggtgcgcg ggacatcgcc gcgtaattcg cgccgcccac accaccaatg cgcgtcgcac   2460
tggcgatgtg aacggtcgcg ggatcgcggg cgaggaaagc gaaagaaggg aaggaaagag   2520
cggtgcaagc ggcccggaga gtttttttccc ttttttttcgt acgtagagtt aatcagtcgt   2580
tggtatcagg gcggggattg aggcgggtag ggcggggatt gaggcgggtc aaggcgggta   2640
agaggcgggg taccgactga ttaaaaaaaa taaatacgtc tccggctccg gcggagccgg   2700
agactcgata aggtcttcat cactcctccg aaaaaacctc cggatccgaa aacgtttttc   2760
gaacctgtcg agtcccgacg ctaaagcgcg gtttgaactg ccgttaggat cgcacttccg   2820
accatcctaa aataggggcg acggtagtac caagctggta acttgacgta gcagcggcac   2880
agggttttat accccctaacc gttcttgcct ctggatggga ccggaggcga gtccttgctc   2940
aagttcatga aggtttctta ctggtgttgg agaagtcacc ttccatttgt cttagaccac   3000
taatacccat ccttttggac caagaggtaa ggactcttct tagctggaaa tttcctgtct   3060
taattatatc aagagtcatc tcttgagttt cttggtggtg ctcctcgagt aaaagaacgg   3120
ttttcaaacc tactacggaa ttctgaataa cttgttggcc ttaaccgttc atttcatctg   3180
taccaaacct atcagcctcc gtcaagacaa atggtccttc ggtacttagt tggtccggtg   3240
gaatctgaga aacactgttc ctagtacgtc cttaaacttt cactgtgcaa aaagggtctt   3300
taactaaacc cctttatatt tgaagagggt cttatgggtc cgcaggagag actccaggtc   3360
ctccttttttc cgtagttcat attcaaactt cagatgctct tctttctgat tgtccttcta   3420
cgaaagttca agagacgagg ggaggatttc gatacgtaaa aatattctgg taccctgaaa   3480
```

-continued

```
acgaccgaaa tctagagaaa cacttccttg gaatgaagac accacactgt attaacctgt   3540
ttgatggatg tctctaaatt tcgagattcc atttatattt taaaaattca catattacac   3600
aatttgatga ctaagattaa caaacacata aaatctaagg ttggatacct tgactactta   3660
ccctcgtcac caccttacgg aaattactcc ttttggacaa aacgagtctt ctttacggta   3720
gatcactact actccgatga cgactgagag ttgtaagatg aggaggtttt ttcttctctt   3780
tccatcttct ggggttcctg aaaggaagtc ttaacgattc aaaaaactca gtacgacaca   3840
aatcattatc ttgagaacga acgaaacgat aaatgtggtg tttccttttt cgacgtgacg   3900
atatgttctt ttaatacctt tttataagac attggaaata ttcatccgta ttgtcaatat   3960
tagtattgta tgacaaaaaa gaatgaggtg tgtccgtatc tcacagacga taattattga   4020
tacgagtttt taacacatgg aaatcgaaaa attaaacatt tccccaatta ttccttataa   4080
actacatatc acggaactga tctctagtat tagtcggtat ggtgtaaaca tctccaaaat   4140
gaacgaaatt ttttggaggg tgtggagggg gacttggact ttgtatttta cttacgttaa   4200
caacaacaat tgaacaaata acgtcgaata ttaccaatgt ttatttcgtt atcgtagtgt   4260
ttaaagtgtt tatttcgtaa aaaaagtgac gtaagatcaa caccaaacag gtttgagtag   4320
ttacatagaa tagtacagac ctagccgacc tactaggagg tcgcgcccct agagtacgac   4380
ctcaagaagc gggtggggtt gaacaaataa cgtcgaatat taccaatgtt tatttcgtta   4440
tcgtagtgtt taaagtgttt atttcgtaaa aaaagtgacg taagatcaac accaaacagg   4500
tttgagtagt tacatagaat agtacagaca tatggcagct ggagatcgat ctcgaaccgc   4560
attagtacca gtatcgacaa aggacacact ttaacaatag gcgagtgtta aggtgtgttg   4620
tatgctcggc cttcgtattt cacatttcgg accccacgga ttactcactc gattgagtgt   4680
aattaacgca acgcgagtga cgggcgaaag gtcagccctt tggacagcac ggtcgacgta   4740
attacttagc cggttgcgcg cccctctccg ccaaacgcat aacccgcgag aaggcgaagg   4800
agcgagtgac tgagcgacgc gagccagcaa gccgacgccg ctcgccatag tcgagtgagt   4860
ttccgccatt atgccaatag gtgtcttagt cccctattgc gtcctttctt gtacactcgt   4920
tttccggtcg ttttccggtc cttggcattt ttccggcgca acgaccgcaa aaaggtatcc   4980
gaggcggggg gactgctcgt agtgttttta gctgcgagtt cagtctccac cgctttgggc   5040
tgtcctgata tttctatggt ccgcaaaggg ggaccttcga gggagcacgc gagaggacaa   5100
ggctgggacg gcgaatggcc tatggacagg cggaaagagg gaagcccttc gcaccgcgaa   5160
agagttacga gtgcgacatc catagagtca agccacatcc agcaagcgag gttcgacccg   5220
acacacgtgc ttgggggggca agtcgggctg gcgacgcgga ataggccatt gatagcagaa   5280
ctcaggttgg gccattctgt gctgaatagc ggtgaccgtc gtcggtgacc attgtcctaa   5340
tcgtctcgct ccatacatcc gccacgatgt ctcaagaact tcaccaccgg attgatgccg   5400
atgtgatctt cctgtcataa accatagacg cgagacgact tcggtcaatg gaagcctttt   5460
tctcaaccat cgagaactag gccgtttgtt tggtggcgac catcgccacc aaaaaaacaa   5520
acgttcgtcg tctaatgcgc gtcttttttt cctagagttc ttctaggaaa ctagaaaaga   5580
tgccccagac tgcgagtcac cttgcttttg agtgcaattc cctaaaacca gtactctaat   5640
agtttttcct agaagtggat ctaggaaaat ttaattttta cttcaaaatt tagttagatt   5700
tcatatatac tcatttgaac cagactgtca atggttacga attagtcact ccgtggatag   5760
agtcgctaga cagataaagc aagtaggtat caacggactg aggggcagca catctattga   5820
tgctatgccc tcccgaatgg tagaccgggg tcacgacgtt actatggcgc tctgggtgcg   5880
```

-continued

```
agtggccgag gtctaaatag tcgttatttg gtcggtcggc cttcccggct cgcgtcttca   5940

ccaggacgtt gaaataggcg gaggtaggtc agataattaa caacggccct tcgatctcat   6000

tcatcaagcg gtcaattatc aaacgcgttg caacaacggt aacgatgtcc gtagcaccac   6060

agtgcgagca gcaaaccata ccgaagtaag tcgaggccaa gggttgctag ttccgctcaa   6120

tgtactaggg ggtacaacac gttttttcgc caatcgagga agccaggagg ctagcaacag   6180

tcttcattca accggcgtca caatagtgag taccaatacc gtcgtgacgt attaagagaa   6240

tgacagtacg gtaggcattc tacgaaaaga cactgaccac tcatgagttg gttcagtaag   6300

actcttatca catacgccgc tggctcaacg agaacgggcc gcagttatgc cctattatgg   6360

cgcggtgtat cgtcttgaaa ttttcacgag tagtaacctt ttgcaagaag ccccgctttt   6420

gagagttcct agaatggcga caactctagg tcaagctaca ttgggtgagc acgtgggttg   6480

actagaagtc gtagaaaatg aaagtggtcg caaagaccca ctcgtttttg tccttccgtt   6540

ttacggcgtt ttttccctta ttcccgctgt gcctttacaa cttatgagta tgagaaggaa   6600

aaagttataa taacttcgta aatagtccca ataacagagt actcgcctat gtataaactt   6660

acataaatct ttttatttgt ttatccccaa ggcgcgtgta aagggggcttt tcacggtgga   6720

ctgcagctgc ctagccctct agacgatcca ctggactccg cgcggccgaa gcttatcggt   6780

ctcattggaa aaaaaaatta aaataaaata aaataaaaac tctacctcaa accgcggcta   6840

gagggctagg ggataccagc tgagagtcat gttagacgag actacggcgt atcaattcgg   6900

tcatagacga gggacgaaca cacaacctcc agcgactcat cacgcgctcg ttttaaattc   6960

gatgttgttc cgttccgaac tggctgttaa cgtacttctt agacgaatcc caatccgcaa   7020

aacgcgacga agc                                                      7033
```

<210> SEQ ID NO 5
<211> LENGTH: 460
<212> TYPE: PRT
<213> ORGANISM: Artificial
<220> FEATURE:
<223> OTHER INFORMATION: Synthetic

<400> SEQUENCE: 5

```
Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Trp Met Ser Trp Val Arg Gln Ala Pro Gly Lys Gly Leu
    50                  55                  60

Glu Trp Val Ala Asp Ile Lys Asn Asp Gly Ser Tyr Thr Asn Tyr Ala
65                  70                  75                  80

Pro Ser Leu Thr Asn Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Leu Thr Gly Thr Trp Gly Gln Gly Thr Met
        115                 120                 125

Val Thr Val Ser Ser Ala Ser Thr Lys Gly Pro Ser Val Phe Pro Leu
    130                 135                 140

Ala Pro Cys Ser Arg Ser Thr Ser Glu Ser Thr Ala Ala Leu Gly Cys
145                 150                 155                 160
```

-continued

```
Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Lys Thr Tyr Thr Cys Asn Val Asp His Lys Pro Ser Asn
    210                 215                 220

Thr Lys Val Asp Lys Arg Val Glu Ser Lys Tyr Gly Pro Pro Cys Pro
225                 230                 235                 240

Pro Cys Pro Ala Pro Glu Phe Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Ser Gln
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
            420                 425                 430

Gly Asn Val Phe Ser Cys Ser Val Met His Glu Ala Leu His Asn His
        435                 440                 445

Tyr Thr Gln Lys Ser Leu Ser Leu Ser Leu Gly Lys
    450                 455                 460
```

```
<210> SEQ ID NO 6
<211> LENGTH: 8874
<212> TYPE: DNA
<213> ORGANISM: Artificial
<220> FEATURE:
<223> OTHER INFORMATION: Synthetic

<400> SEQUENCE: 6

aattacgggg tcattagttc atagcccata tatggagttc cgcgttacat aacttacggt     60

aaatggcccg cctggctgac cgcccaacga cccccgccca ttgacgtcaa taatgacgta    120

tgttcccata gtaacgccaa tagggacttt ccattgacgt caatgggtgg actatttacg    180

gtaaactgcc cacttggcag tacatcaagt gtatcatatg ccaagtacgc cccctattga    240

cgtcaatgac ggtaaatggc ccgcctggca ttatgcccag tacatgacct tatgggactt    300

tcctacttgg cagtacatct acgtattagt catcgctatt accatggtga tgcggttttg    360
```

-continued

```
gcagtacatc aatgggcgtg gatagcggtt tgactcacgg ggatttccaa gtctccaccc    420

cattgacgtc aatgggagtt tgttttggca ccaaaatcaa cgggactttc caaaatgtcg    480

taacaactcc gccccattga cgcaaatggg cggtaggcgt gtacggtggg aggtctatat    540

aagcagagct ctctggctaa ctagagaacc cactgcttac tggcttatcg aaattaatac    600

gactcactat agggagaccc aagcttggta ccatggaagc cccagctcag cttctcttcc    660

tcctgctact ctggctccca gataccaccg gagacattgt aatgacccag tctccagact    720

ccctggctgt gtcactagga gagcgggcca ctataaactg caagtccagt cagagtcttt    780

tatccagtgg aaaccaaaag aactatttgg cctggtatca gcagaaacca ggccagcctc    840

ctaaactact gatctactat gcatccacta ggcaatcagg ggtccctgat cgcttcagtg    900

gcagtggatc tgggacggac ttcactctga ccatcagcag cctgcaggct gaggacgtgg    960

cagtctatta ctgcctgcag tatgacagat atccattcac gttcggccaa gggacgaagt   1020

tggaaataaa acgtaagtct cgagtctcta gataaccggt caatcgattg gaattctaaa   1080

ctctgagggg gtcggatgac gtggccattc tttgcctaaa gcattgagtt tactgcaagg   1140

tcagaaaagc atgcaaagcc ctcagaatgg ctgcaaagag ctccaacaaa acaatttaga   1200

actttattaa ggaatagggg gaagctagga agaaactcaa aacatcaaga ttttaaatac   1260

gcttcttggt ctccttgcta taattatctg ggataagcat gctgttttct gtctgtccct   1320

aacatgccct gtgattatcc gcaaacaaca cacccaaggg cagaactttg ttacttaaac   1380

accatcctgt ttgcttcttt cctcaggaac tgtggctgca ccatctgtct tcatcttccc   1440

gccatctgat gagcagttga aatctggaac tgcctctgtt gtgtgcctgc tgaataactt   1500

ctatcccaga gaggccaaag tacagtggaa ggtggataac gccctccaat cgggtaactc   1560

ccaggagagt gtcacagagc aggacagcaa ggacagcacc tacagcctca gcagcaccct   1620

gacgctgagc aaagcagact acgagaaaca caaagtctac gcctgcgaag tcacccatca   1680

gggcctgagc tcgcccgtca caaagagctt caacagggga gagtgttaga gggagaagtg   1740

cccccacctg ctcctcagtt ccagcctgac cccctcccat cctttggcct ctgacccttt   1800

ttccacaggg gacctacccc tattgcggtc ctccagctca tctttcacct caccccccctc   1860

ctcctccttg gctttaatta tgctaatgtt ggaggagaat gaataaataa agtgaatctt   1920

tgcacctgtg gtttctctct ttcctcattt aataattatt atctgttgtt ttaccaacta   1980

ctcaatttct cttataaggg actaaatatg tagtcatcct aaggcgcata accatttata   2040

aaaatcatcc ttcattctat tttaccctat catcctctgc aagacagtcc tccctcaaac   2100

ccacaagcct tctgtcctca cagtcccctg ggccatggta ggagagactt gcttccttgt   2160

tttcccctcc tcagcaagcc ctcatagtcc tttttaaggg tgacaggtct tacagtcata   2220

tatcctttga ttcaattccc tgagaatcaa ccaaagcaaa tttttcaaaa gaagaaacct   2280

gctataaaga gaatcattca ttgcaacatg atataaaata acaacacaat aaaagcaatt   2340

aaataaacaa acaataggga aatgtttaag ttcatcatgg tacttagact taatggaatg   2400

tcatgcctta tttacatttt taaacaggta ctgagggact cctgtctgcc aagggccgta   2460

ttgagtactt tccacaacct aatttaatcc acactatact gtgagattaa aaacattcat   2520

taaaatgttg caaaggttct ataaagctga gagacaaata tattctataa ctcagcaatc   2580

ccacttctag atgactgagt gtccccaccc accaaaaaac tatgcaagaa tgttcaaagc   2640

agctttattt acaaaagcca aaaattggaa atagcccgat tgtccaacaa tagaatgagt   2700

tattaaactg tggtatgttt atacattaga atacccaatg aggagaatta acaagctaca   2760
```

-continued

```
actataccta ctcacacaga tgaatctcat aaaaataatg ttacataaga gaaactcaat   2820
gcaaaagata tgttctgtat gttttcatcc atataaagtt caaaaccagg taaaaataaa   2880
gttagaaatt tggatggaaa ttactcttag ctggggggtgg gcgagttagt gcctgggaga   2940
agacaagaag gggcttctgg ggtcttggta atgttctgtt cctcgtgtgg ggttgtgcag   3000
ttatgatctg tgcactgttc tgtatacaca ttatgcttca aaataacttc acataaagaa   3060
catcttatac ccagttaata gatagaagag gaataagtaa taggtcaaga ccacgcagct   3120
ggtaagtggg ggggcctggg atcaaatagc tacctgccta atcctgccct cttgagccct   3180
gaatgagtct gccttccagg gctcaaggtg ctcaacaaaa caacaggcct gctattttcc   3240
tggcatctgt gccctgtttg gctagctagg agcacacata catagaaatt aaatgaaaca   3300
gaccttcagc aaggggacag aggacagaat taaccttgcc cagacactgg aaacccatgt   3360
atgaacactc acatgtttgg gaagggggaa gggcacatgt aaatgaggac tcttcctcat   3420
tctatggggc actctggccc tgcccctctc agctactcat ccatccaaca cacctttcta   3480
agtacctctc tctgcctaca ctctgaaggg gttcaggagt aactaacaca gcatcccttc   3540
cctcaaatga ctgacaatcc ctttgtcctg ctttgttttt ctttccagtc agtactggga   3600
aagtggggaa ggacagtcat ggagaaacta cataaggaag caccttgccc ttctgcctct   3660
tgagaatgtt gatgagtatc aaatctttca aactttggag gtttgagtag ggtgagact   3720
cagtaatgtc ccttccaatg acatgaactt gctcactcat ccctgggggc caaattgaac   3780
aatcaaaggc aggcataatc cagttatgaa ttcttgcggc cgcttgctag cttcacgtgt   3840
tggatccaac cgcggaaggg ccctattcta tagtgtcacc taaatgctag agctcgctga   3900
tcagcctcga ctgtgccttc tagttgccag ccatctgttg tttgcccctc ccccgtgcct   3960
tccttgaccc tggaaggtgc cactcccact gtcctttcct aataaaatga ggaaattgca   4020
tcgcattgtc tgagtaggtg tcattctatt ctggggggtg gggtggggca ggacagcaag   4080
ggggaggatt gggaagacaa tagcaggcat gctggggatg cggtgggctc tatggcttct   4140
gaggcggaaa gaaccagctg gggctctagg gggtatcccc acgcgccctg tagcggcgca   4200
ttaagcgcgg cgggtgtggt ggttacgcgc agcgtgaccg ctacacttgc cagcgcccta   4260
gcgcccgctc ctttcgcttt cttcccttcc tttctcgcca cgttcgccgg gcctctcaaa   4320
aaagggaaaa aaagcatgca tctcaattag tcagcaacca tagtcccgcc cctaactccg   4380
cccatcccgc ccctaactcc gcccagttcc gcccattctc cgccccatgg ctgactaatt   4440
ttttttattt atgcagaggc cgaggccgcc tcggcctctg agctattcca gaagtagtga   4500
ggaggctttt ttggaggcct aggcttttgc aaaaagcttg gacagctcag ggctgcgatt   4560
tcgcgccaaa cttgacggca atcctagcgt gaaggctggt aggattttat ccccgctgcc   4620
atcatggttc gaccattgaa ctgcatcgtc gccgtgtccc aaaatatggg gattggcaag   4680
aacggagacc taccctggcc tccgctcagg aacgagttca agtacttcca aagaatgacc   4740
acaacctctt cagtggaagg taaacagaat ctggtgatta tgggtaggaa aacctggttc   4800
tccattcctg agaagaatcg acctttaaag gacagaatta atatagttct cagtagagaa   4860
ctcaaagaac caccacgagg agctcatttt cttgccaaaa gtttggatga tgccttaaga   4920
cttattgaac aaccggaatt ggcaagtaaa gtagacatgg tttggatagt cggaggcagt   4980
tctgtttacc aggaagccat gaatcaacca ggccacctta gactctttgt gacaaggatc   5040
atgcaggaat ttgaaagtga cacgtttttc ccagaaattg atttggggaa atataaactt   5100
ctcccagaat acccaggcgt cctctctgag gtccaggagg aaaaaggcat caagtataag   5160
```

-continued

```
tttgaagtct acgagaagaa agactaacag gaagatgctt tcaagttctc tgctcccctc   5220
ctaaagctat gcatttttat aagaccatgg gacttttgct ggctttagat ctctttgtga   5280
aggaacctta cttctgtggt gtgacataat tggacaaact acctacagag atttaaagct   5340
ctaaggtaaa tataaaattt ttaagtgtat aatgtgttaa actactgatt ctaattgttt   5400
gtgtatttta gattccaacc tatggaactg atgaatggga gcagtggtgg aatgccttta   5460
atgaggaaaa cctgttttgc tcagaagaaa tgccatctag tgatgatgag gctactgctg   5520
actctcaaca ttctactcct ccaaaaaaga agagaaaggt agaagacccc aaggactttc   5580
cttcagaatt gctaagtttt ttgagtcatg ctgtgtttag taatagaact cttgcttgct   5640
ttgctattta caccacaaag gaaaaagctg cactgctata caagaaaatt atggaaaaat   5700
attctgtaac ctttataagt aggcataaca gttataatca taacatactg ttttttctta   5760
ctccacacag gcatagagtg tctgctatta ataactatgc tcaaaaattg tgtaccttta   5820
gctttttaat ttgtaaaggg gttaataagg aatatttgat gtatagtgcc ttgactagag   5880
atcataatca gccataccac atttgtagag gttttacttg ctttaaaaaa cctcccacac   5940
ctccccctga acctgaaaca taaaatgaat gcaattgttg ttgttaactt gtttattgca   6000
gcttataatg gttacaaata aagcaatagc atcacaaatt tcacaaataa agcatttttt   6060
tcactgcatt ctagttgtgg tttgtccaaa ctcatcaatg tatcttatca tgtctggatc   6120
ggctggatga tcctccagcg cggggatctc atgctggagt tcttcgccca ccccaacttg   6180
tttattgcag cttataatgg ttacaaataa agcaatagca tcacaaattt cacaaataaa   6240
gcattttttt cactgcattc tagttgtggt ttgtccaaac tcatcaatgt atcttatcat   6300
gtctgtatac cgtcgacctc tagctagagc ttggcgtaat catggtcata gctgtttcct   6360
gtgtgaaatt gttatccgct cacaattcca cacaacatac gagccggaag cataaagtgt   6420
aaagcctggg gtgcctaatg agtgagctaa ctcacattaa ttgcgttgcg ctcactgccc   6480
gctttccagt cgggaaacct gtcgtgccag ctgcattaat gaatcggcca acgcgcgggg   6540
agaggcggtt tgcgtattgg gcgctcttcc gcttcctcgc tcactgactc gctgcgctcg   6600
gtcgttcggc tgcggcgagc ggtatcagct cactcaaagg cggtaatacg gttatccaca   6660
gaatcagggg ataacgcagg aaagaacatg tgagcaaaag gccagcaaaa ggccaggaac   6720
cgtaaaaagg ccgcgttgct ggcgtttttc cataggctcc gcccccctga cgagcatcac   6780
aaaaatcgac gctcaagtca gaggtggcga aacccgacag gactataaag ataccaggcg   6840
tttccccctg gaagctccct cgtgcgctct cctgttccga ccctgccgct taccggatac   6900
ctgtccgcct ttctcccttc gggaagcgtg gcgctttctc aatgctcacg ctgtaggtat   6960
ctcagttcgg tgtaggtcgt tcgctccaag ctgggctgtg tgcacgaacc ccccgttcag   7020
cccgaccgct gcgccttatc cggtaactat cgtcttgagt ccaacccggt aagacacgac   7080
ttatcgccac tggcagcagc cactggtaac aggattagca gagcgaggta tgtaggcggt   7140
gctacagagt tcttgaagtg gtggcctaac tacggctaca ctagaaggac agtatttggt   7200
atctgcgctc tgctgaagcc agttaccttc ggaaaaagag ttggtagctc ttgatccggc   7260
aaacaaacca ccgctggtag cggtggtttt tttgtttgca agcagcagat tacgcgcaga   7320
aaaaaaggat ctcaagaaga tcctttgatc ttttctacgg ggtctgacgc tcagtggaac   7380
gaaaactcac gttaagggat tttggtcatg agattatcaa aaaggatctt cacctagatc   7440
cttttaaatt aaaaatgaag ttttaaatca atctaaagta tatatgagta aacttggtct   7500
gacagttacc aatgcttaat cagtgaggca cctatctcag cgatctgtct atttcgttca   7560
```

-continued

```
tccatagttg cctgactccc cgtcgtgtag ataactacga tacgggaggg cttaccatct   7620

ggccccagtg ctgcaatgat accgcgagac ccacgctcac cggctccaga tttatcagca   7680

ataaaccagc cagccggaag ggccgagcgc agaagtggtc ctgcaacttt atccgcctcc   7740

atccagtcta ttaattgttg ccgggaagct agagtaagta gttcgccagt taatagtttg   7800

cgcaacgttg ttgccattgc tacaggcatc gtggtgtcac gctcgtcgtt tggtatggct   7860

tcattcagct ccggttccca acgatcaagg cgagttacat gatcccccat gttgtgcaaa   7920

aaagcggtta gctccttcgg tcctccgatc gttgtcagaa gtaagttggc cgcagtgtta   7980

tcactcatgg ttatggcagc actgcataat tctcttactg tcatgccatc cgtaagatgc   8040

ttttctgtga ctggtgagta ctcaaccaag tcattctgag aatagtgtat gcggcgaccg   8100

agttgctctt gcccggcgtc aatacgggat aataccgcgc cacatagcag aactttaaaa   8160

gtgctcatca ttggaaaacg ttcttcgggg cgaaaactct caaggatctt accgctgttg   8220

agatccagtt cgatgtaacc cactcgtgca cccaactgat cttcagcatc ttttactttc   8280

accagcgttt ctgggtgagc aaaaacagga aggcaaaatg ccgcaaaaaa gggaataagg   8340

gcgacacgga aatgttgaat actcatactc ttcctttttc aatattattg aagcatttat   8400

cagggttatt gtctcatgag cggatacata tttgaatgta tttagaaaaa taaacaaata   8460

ggggttccgc gcacatttcc ccgaaaagtg ccacctgacg tcgacggatc gggagatctg   8520

ctagcccggg tgacctgagg cgcgccggct tcgaatagcc agagtaacct tttttttaa   8580

ttttatttta ttttattttt gagatggagt ttggcgccga tctcccgatc ccctatggtc   8640

gactctcagt acaatctgct ctgatgccgc atagttaagc cagtatctgc tccctgcttg   8700

tgtgttggag gtcgctgagt agtgcgcgag caaaatttaa gctacaacaa ggcaaggctt   8760

gaccgacaat tgcatgaaga atctgcttag ggttaggcgt tttgcgctgc ttcgcgatgt   8820

acgggccaga tatacgcgtt gacattgatt attgactagt tattaatagt aatc         8874
```

<210> SEQ ID NO 7
<211> LENGTH: 8874
<212> TYPE: DNA
<213> ORGANISM: Artificial
<220> FEATURE:
<223> OTHER INFORMATION: Synthetic

<400> SEQUENCE: 7

```
ttaatgcccc agtaatcaag tatcgggtat atacctcaag gcgcaatgta ttgaatgcca     60

tttaccgggc ggaccgactg gcgggttgct gggggcgggt aactgcagtt attactgcat    120

acaagggtat cattgcggtt atccctgaaa ggtaactgca gttacccacc tgataaatgc    180

catttgacgg gtgaaccgtc atgtagttca catagtatac ggttcatgcg gggataact    240

gcagttactg ccatttaccg ggcggaccgt aatacgggtc atgtactgga ataccctgaa    300

aggatgaacc gtcatgtaga tgcataatca gtagcgataa tggtaccact acgccaaaac    360

cgtcatgtag ttacccgcac ctatcgccaa actgagtgcc cctaaaggtt cagaggtggg    420

gtaactgcag ttaccctcaa acaaaaccgt ggttttagtt gccctgaaag gttttacagc    480

attgttgagg cggggtaact gcgtttaccc gccatccgca catgccaccc tccagatata    540

ttcgtctcga gagaccgatt gatctcttgg gtgacgaatg accgaatagc tttaattatg    600

ctgagtgata tccctctggg ttcgaaccat ggtaccttcg ggtcgagtc gaagagaagg    660

aggacgatga gaccgagggt ctatggtggc ctctgtaaca ttactgggtc agaggtctga    720

gggaccgaca cagtgatcct ctcgcccggt gatatttgac gttcaggtca gtctcagaaa    780
```

-continued

```
ataggtcacc tttggttttc ttgataaacc ggaccatagt cgtctttggt ccggtcggag    840
gatttgatga ctagatgata cgtaggtgat ccgttagtcc ccagggacta gcgaagtcac    900
cgtcacctag accctgcctg aagtgagact ggtagtcgtc ggacgtccga ctcctgcacc    960
gtcagataat gacggacgtc atactgtcta taggtaagtg caagccggtt ccctgcttca   1020
acctttattt tgcattcaga gctcagagat ctattggcca gttagctaac cttaagattt   1080
gagactcccc cagcctactg caccggtaag aaacggattt cgtaactcaa atgacgttcc   1140
agtcttttcg tacgtttcgg gagtcttacc gacgtttctc gaggttgttt tgttaaatct   1200
tgaaataatt ccttatcccc cttcgatcct tctttgagtt ttgtagttct aaaatttatg   1260
cgaagaacca gaggaacgat attaatagac cctattcgta cgacaaaaga cagacaggga   1320
ttgtacggga cactaatagg cgtttgttgt gtgggttccc gtcttgaaac aatgaatttg   1380
tggtaggaca aacgaagaaa ggagtccttg acaccgacgt ggtagacaga agtagaaggg   1440
cggtagacta ctcgtcaact ttagaccttg acggagacaa cacacggacg acttattgaa   1500
gatagggtct ctccggtttc atgtcacctt ccacctattg cgggaggtta gcccattgag   1560
ggtcctctca cagtgtctcg tcctgtcgtt cctgtcgtgg atgtcggagt cgtcgtggga   1620
ctgcgactcg tttcgtctga tgctctttgt gtttcagatg cggacgcttc agtgggtagt   1680
cccggactcg agcgggcagt gtttctcgaa gttgtcccct ctcacaatct ccctcttcac   1740
gggggtggac gaggagtcaa ggtcggactg ggggagggta ggaaaccgga gactgggaaa   1800
aaggtgtccc ctggatgggg ataacgccag gaggtcgagt agaaagtgga gtgggggag    1860
gaggaggaac cgaaattaat acgattacaa cctcctctta cttatttatt tcacttagaa   1920
acgtggacac caaagagaga aaggagtaaa ttattaataa tagacaacaa aatggttgat   1980
gagttaaaga gaatattccc tgatttatac atcagtagga ttccgcgtat tggtaaatat   2040
ttttagtagg aagtaagata aaatgggata gtaggagacg ttctgtcagg agggagtttg   2100
ggtgttcgga agacaggagt gtcaggggac ccggtaccat cctctctgaa cgaaggaaca   2160
aaaggggagg agtcgttcgg gagtatcagg aaaaattccc actgtccaga atgtcagtat   2220
ataggaaact aagttaaggg actcttagtt ggtttcgttt aaaaagtttt cttctttgga   2280
cgatatttct cttagtaagt aacgttgtac tatattttat tgttgtgtta ttttcgttaa   2340
tttatttgtt tgttatccct ttacaaattc aagtagtacc atgaatctga attaccttac   2400
agtacggaat aaatgtaaaa atttgtccat gactccctga ggacagacgg ttcccggcat   2460
aactcatgaa aggtgttgga ttaaattagg tgtgatatga cactctaatt tttgtaagta   2520
attttacaac gtttccaaga tatttcgact ctctgtttat ataagatatt gagtcgttag   2580
ggtgaagatc tactgactca caggggtggg tggttttttg atacgttctt acaagtttcg   2640
tcgaaataaa tgttttcggt ttttaacctt tatcgggcta acaggttgtt atcttactca   2700
ataatttgac accatacaaa tatgtaatct tatgggttac tcctcttaat tgttcgatgt   2760
tgatatggat gagtgtgtct acttagagta tttttattac aatgtattct ctttgagtta   2820
cgttttctat acaagacata caaaagtagg tatatttcaa gttttggtcc atttttattt   2880
caatctttaa acctaccttt aatgagaatc gacccccacc cgctcaatca cggaccctct   2940
tctgttcttc cccgaagacc ccagaaccat tacaagacaa ggagcacacc ccaacacgtc   3000
aatactagac acgtgacaag acatatgtgt aatacgaagt tttattgaag tgtatttctt   3060
gtagaatatg ggtcaattat ctatcttctc cttattcatt atccagttct ggtgcgtcga   3120
ccattcaccc ccccggaccc tagtttatcg atggacggat taggacggga gaactcggga   3180
```

-continued

```
cttactcaga cggaaggtcc cgagttccac gagttgtttt gttgtccgga cgataaaagg   3240
accgtagaca cgggacaaac cgatcgatcc tcgtgtgtat gtatctttaa tttactttgt   3300
ctggaagtcg ttcccctgtc tcctgtctta attggaacgg gtctgtgacc tttgggtaca   3360
tacttgtgag tgtacaaacc cttccccctt cccgtgtaca tttactcctg agaaggagta   3420
agataccccg tgagaccggg acggggagag tcgatgagta ggtaggttgt gtggaaagat   3480
tcatggagag agacggatgt gagacttccc caagtcctca ttgattgtgt cgtagggaag   3540
ggagtttact gactgttagg gaaacaggac gaaacaaaaa gaaaggtcag tcatgaccct   3600
ttcacccctt cctgtcagta cctctttgat gtattccttc gtggaacggg aagacggaga   3660
actcttacaa ctactcatag tttagaaagt ttgaaacctc caaactcatc cccactctga   3720
gtcattacag ggaaggttac tgtacttgaa cgagtgagta gggacccccg gtttaacttg   3780
ttagtttccg tccgtattag gtcaatactt aagaacgccg gcgaacgatc gaagtgcaca   3840
acctaggttg gcgccttccc gggataagat atcacagtgg atttacgatc tcgagcgact   3900
agtcggagct gacacggaag atcaacggtc ggtagacaac aaacggggag ggggcacgga   3960
aggaactggg accttccacg gtgagggtga caggaaagga ttattttact cctttaacgt   4020
agcgtaacag actcatccac agtaagataa gacccccccac cccaccccgt cctgtcgttc   4080
cccctcctaa cccttctgtt atcgtccgta cgacccctac gccacccgag ataccgaaga   4140
ctccgccttt cttggtcgac cccgagatcc cccatagggg tgcgcgggac atcgccgcgt   4200
aattcgcgcc gcccacacca ccaatgcgcg tcgcactggc gatgtgaacg gtcgcgggat   4260
cgcgggcgag gaaagcgaaa gaagggaagg aaagagcggt gcaagcggcc cggagagttt   4320
tttccctttt tttcgtacgt agagttaatc agtcgttggt atcagggcgg ggattgaggc   4380
gggtagggcg gggattgagg cgggtcaagg cgggtaagag gcggggtacc gactgattaa   4440
aaaaaataaa tacgtctccg gctccggcgg agccggagac tcgataaggt cttcatcact   4500
cctccgaaaa aacctccgga tccgaaaacg tttttcgaac ctgtcgagtc ccgacgctaa   4560
agcgcggttt gaactgccgt taggatcgca cttccgacca tcctaaaata ggggcgacgg   4620
tagtaccaag ctggtaactt gacgtagcag cggcacaggg ttttataccc ctaaccgttc   4680
ttgcctctgg atgggaccgg aggcgagtcc ttgctcaagt tcatgaaggt ttcttactgg   4740
tgttggagaa gtcaccttcc atttgtctta gaccactaat acccatcctt ttggaccaag   4800
aggtaaggac tcttcttagc tggaaatttc ctgtcttaat tatatcaaga gtcatctctt   4860
gagtttcttg gtggtgctcc tcgagtaaaa gaacggtttt caaacctact acggaattct   4920
gaataacttg ttggccttaa ccgttcattt catctgtacc aaacctatca gcctccgtca   4980
agacaaatgg tccttcggta cttagttggt ccggtggaat ctgagaaaca ctgttcctag   5040
tacgtcctta aactttcact gtgcaaaaag ggtctttaac taaacccctt tatatttgaa   5100
gagggtctta tgggtccgca ggagagactc caggtcctcc tttttccgta gttcatattc   5160
aaacttcaga tgctcttctt tctgattgtc cttctacgaa agttcaagag acgaggggag   5220
gatttcgata cgtaaaaata ttctggtacc ctgaaaacga ccgaaatcta gagaaacact   5280
tccttggaat gaagacacca cactgtatta acctgtttga tggatgtctc taaatttcga   5340
gattccattt atattttaaa aattcacata ttacacaatt tgatgactaa gattaacaaa   5400
cacataaaat ctaaggttgg ataccttgac tacttaccct cgtcaccacc ttacggaaat   5460
tactcctttt ggacaaaacg agtcttcttt acggtagatc actactactc cgatgacgac   5520
tgagagttgt aagatgagga ggttttttct tctctttcca tcttctgggg ttcctgaaag   5580
```

-continued

```
gaagtcttaa cgattcaaaa aactcagtac gacacaaatc attatcttga gaacgaacga   5640
aacgataaat gtggtgtttc ctttttcgac gtgacgatat gttcttttaa taccttttta   5700
taagacattg gaaatattca tccgtattgt caatattagt attgtatgac aaaaaagaat   5760
gaggtgtgtc cgtatctcac agacgataat tattgatacg agtttttaac acatggaaat   5820
cgaaaaatta aacatttccc caattattcc ttataaacta catatcacgg aactgatctc   5880
tagtattagt cggtatggtg taaacatctc caaaatgaac gaaatttttt ggagggtgtg   5940
gagggggact tggactttgt attttactta cgttaacaac aacaattgaa caaataacgt   6000
cgaatattac caatgtttat ttcgttatcg tagtgtttaa agtgtttatt tcgtaaaaaa   6060
agtgacgtaa gatcaacacc aaacaggttt gagtagttac atagaatagt acagacctag   6120
ccgacctact aggaggtcgc gcccctagag tacgacctca agaagcgggt ggggttgaac   6180
aaataacgtc gaatattacc aatgtttatt tcgttatcgt agtgtttaaa gtgtttattt   6240
cgtaaaaaaa gtgacgtaag atcaacacca aacaggtttg agtagttaca tagaatagta   6300
cagacatatg gcagctggag atcgatctcg aaccgcatta gtaccagtat cgacaaagga   6360
cacactttaa caataggcga gtgttaaggt gtgttgtatg ctcggccttc gtatttcaca   6420
tttcggaccc cacggattac tcactcgatt gagtgtaatt aacgcaacgc gagtgacggg   6480
cgaaaggtca gccctttgga cagcacggtc gacgtaatta cttagccggt tgcgcgcccc   6540
tctccgccaa acgcataacc cgcgagaagg cgaaggagcg agtgactgag cgacgcgagc   6600
cagcaagccg acgccgctcg ccatagtcga gtgagtttcc gccattatgc caataggtgt   6660
cttagtcccc tattgcgtcc tttcttgtac actcgttttc cggtcgtttt ccggtccttg   6720
gcatttttcc ggcgcaacga ccgcaaaaag gtatccgagg cggggggact gctcgtagtg   6780
tttttagctg cgagttcagt ctccaccgct ttgggctgtc ctgatatttc tatggtccgc   6840
aaagggggac cttcgaggga gcacgcgaga ggacaaggct gggacggcga atggcctatg   6900
gacaggcgga aagagggaag cccttcgcac cgcgaaagag ttacgagtgc gacatccata   6960
gagtcaagcc acatccagca agcgaggttc gacccgacac acgtgcttgg ggggcaagtc   7020
gggctggcga cgcggaatag gccattgata gcagaactca ggttgggcca ttctgtgctg   7080
aatagcggtg accgtcgtcg gtgaccattg tcctaatcgt ctcgctccat acatccgcca   7140
cgatgtctca agaacttcac caccggattg atgccgatgt gatcttcctg tcataaacca   7200
tagacgcgag acgacttcgg tcaatggaag cctttttctc aaccatcgag aactaggccg   7260
tttgtttggt ggcgaccatc gccaccaaaa aaacaaacgt tcgtcgtcta atgcgcgtct   7320
ttttttccta gagttcttct aggaaactag aaaagatgcc ccagactgcg agtcaccttg   7380
cttttgagtg caattcccta aaaccagtac tctaatagtt tttcctagaa gtggatctag   7440
gaaaatttaa tttttacttc aaaatttagt tagatttcat atatactcat ttgaaccaga   7500
ctgtcaatgg ttacgaatta gtcactccgt ggatagagtc gctagacaga taaagcaagt   7560
aggtatcaac ggactgaggg gcagcacatc tattgatgct atgccctccc gaatggtaga   7620
ccggggtcac gacgttacta tggcgctctg ggtgcgagtg gccgaggtct aaatagtcgt   7680
tatttggtcg gtcggccttc ccggctcgcg tcttcaccag gacgttgaaa taggcggagg   7740
taggtcagat aattaacaac ggcccttcga tctcattcat caagcggtca attatcaaac   7800
gcgttgcaac aacggtaacg atgtccgtag caccacagtg cgagcagcaa accataccga   7860
agtaagtcga ggccaagggt tgctagttcc gctcaatgta ctagggggta caacacgttt   7920
tttcgccaat cgaggaagcc aggaggctag caacagtctt cattcaaccg gcgtcacaat   7980
```

-continued

```
agtgagtacc aataccgtcg tgacgtatta agagaatgac agtacggtag gcattctacg   8040

aaaagacact gaccactcat gagttggttc agtaagactc ttatcacata cgccgctggc   8100

tcaacgagaa cgggccgcag ttatgcccta ttatggcgcg gtgtatcgtc ttgaaatttt   8160

cacgagtagt aaccttttgc aagaagcccc gcttttgaga gttcctagaa tggcgacaac   8220

tctaggtcaa gctacattgg gtgagcacgt gggttgacta gaagtcgtag aaaatgaaag   8280

tggtcgcaaa gacccactcg tttttgtcct tccgttttac ggcgtttttt cccttattcc   8340

cgctgtgcct ttacaactta tgagtatgag aaggaaaaag ttataataac ttcgtaaata   8400

gtcccaataa cagagtactc gcctatgtat aaacttacat aaatcttttt atttgtttat   8460

ccccaaggcg cgtgtaaagg ggcttttcac ggtggactgc agctgcctag ccctctagac   8520

gatcgggccc actggactcc gcgcggccga agcttatcgg tctcattgga aaaaaaaatt   8580

aaaataaaat aaaataaaaa ctctacctca aaccgcggct agagggctag gggataccag   8640

ctgagagtca tgttagacga gactacggcg tatcaattcg gtcatagacg agggacgaac   8700

acacaacctc cagcgactca tcacgcgctc gttttaaatt cgatgttgtt ccgttccgaa   8760

ctggctgtta acgtacttct tagacgaatc ccaatccgca aaacgcgacg aagcgctaca   8820

tgcccggtct atatgcgcaa ctgtaactaa taactgatca ataattatca ttag         8874
```

<210> SEQ ID NO 8
<211> LENGTH: 240
<212> TYPE: PRT
<213> ORGANISM: Artificial
<220> FEATURE:
<223> OTHER INFORMATION: Synthetic

<400> SEQUENCE: 8

```
Met Glu Ala Pro Ala Gln Leu Leu Phe Leu Leu Leu Leu Trp Leu Pro
1               5                   10                  15

Asp Thr Thr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Ser Ser Gly Asn Gln Lys Asn Tyr Leu Ala Trp Tyr Gln Gln
    50                  55                  60

Lys Pro Gly Gln Pro Pro Lys Leu Leu Ile Tyr Tyr Ala Ser Thr Arg
65                  70                  75                  80

Gln Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Leu Gln Tyr Asp Arg Tyr Pro Phe Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205
```

-continued

```
Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 9
<211> LENGTH: 82
<212> TYPE: DNA
<213> ORGANISM: Artificial
<220> FEATURE:
<223> OTHER INFORMATION: Synthetic

<400> SEQUENCE: 9

agataccacc ggagacattg taatgaccca gtctccagac tccctggctg tgtcactagg     60

agagcgggcc actataaact gc                                              82


<210> SEQ ID NO 10
<211> LENGTH: 86
<212> TYPE: DNA
<213> ORGANISM: Artificial
<220> FEATURE:
<223> OTHER INFORMATION: Synthetic

<400> SEQUENCE: 10

tccctgatcg cttcagtggc agtggatctg ggacggactt cactctgacc atcagcagcc     60

tgcaggctga ggacgtggca gtctat                                          86


<210> SEQ ID NO 11
<211> LENGTH: 81
<212> TYPE: DNA
<213> ORGANISM: Artificial
<220> FEATURE:
<223> OTHER INFORMATION: Synthetic

<400> SEQUENCE: 11

ctcagaggta ccatggaagc cccagctcag cttctcttcc tcctgctact ctggctccca     60

gataccaccg gagacattgt a                                               81


<210> SEQ ID NO 12
<211> LENGTH: 90
<212> TYPE: DNA
<213> ORGANISM: Artificial
<220> FEATURE:
<223> OTHER INFORMATION: Synthetic

<400> SEQUENCE: 12

ctgccactga agcgatcagg gacccctgat tgcctagtgg atgcatagta gatcagtagt     60

ttaggaggct ggcctggttt ctgctgatac                                      90


<210> SEQ ID NO 13
<211> LENGTH: 82
<212> TYPE: DNA
<213> ORGANISM: Artificial
<220> FEATURE:
<223> OTHER INFORMATION: Synthetic

<400> SEQUENCE: 13

tctagagact cgagacttac gttttatttc caacttcgtc ccttggccga acgtgaatgg     60

atatctgtca tactgcaggc ag                                              82
```

-continued

<210> SEQ ID NO 14
<211> LENGTH: 62
<212> TYPE: DNA
<213> ORGANISM: Artificial
<220> FEATURE:
<223> OTHER INFORMATION: Synthetic

<400> SEQUENCE: 14
ggtttggtgc aacctggggg ttctctgcga ctctcttgtg cagcctcggg attcactttc 60
ag 62

<210> SEQ ID NO 15
<211> LENGTH: 66
<212> TYPE: DNA
<213> ORGANISM: Artificial
<220> FEATURE:
<223> OTHER INFORMATION: Synthetic

<400> SEQUENCE: 15
cagcagcaac aggtgcccac tccgaagtac aactggtgga gtctggagga ggtttggtgc 60
aacctg 66

<210> SEQ ID NO 16
<211> LENGTH: 60
<212> TYPE: DNA
<213> ORGANISM: Artificial
<220> FEATURE:
<223> OTHER INFORMATION: Synthetic

<400> SEQUENCE: 16
ctgagaggta ccatggactg gacctggagg atcctcttct tggtggcagc agcaacaggt 60

<210> SEQ ID NO 17
<211> LENGTH: 58
<212> TYPE: DNA
<213> ORGANISM: Artificial
<220> FEATURE:
<223> OTHER INFORMATION: Synthetic

<400> SEQUENCE: 17
atgatggcag ttacacaaac tatgcaccat ccctaacgaa tcgattcaca atctcaag 58

<210> SEQ ID NO 18
<211> LENGTH: 70
<212> TYPE: DNA
<213> ORGANISM: Artificial
<220> FEATURE:
<223> OTHER INFORMATION: Synthetic

<400> SEQUENCE: 18
gcatagtttg tgtaactgcc atcattttta atatctccaa tccactccat ggtctttcca 60
ggcgcctgac 70

<210> SEQ ID NO 19
<211> LENGTH: 80
<212> TYPE: DNA
<213> ORGANISM: Artificial
<220> FEATURE:
<223> OTHER INFORMATION: Synthetic

<400> SEQUENCE: 19
gttctctagt acagtaataa acggctgtgt cctcagctct cagagagttc atctgcaggt 60
acagggagtt cttggcattg 80

-continued

```
<210> SEQ ID NO 20
<211> LENGTH: 72
<212> TYPE: DNA
<213> ORGANISM: Artificial
<220> FEATURE:
<223> OTHER INFORMATION: Synthetic

<400> SEQUENCE: 20

ctcgaggcta gctgaggaga ctgtgaccat ggttccttgg ccccaagtcc cagttagttc      60

tctagtacag ta                                                          72
```